(12) United States Patent
Matta

(10) Patent No.: US 12,227,788 B2
(45) Date of Patent: *Feb. 18, 2025

(54) COMPOSITIONS, METHODS AND TREATMENTS FOR INHIBITING CELL ADHESION AND VIRUS BINDING AND PENETRATION

(71) Applicant: TUMOREND, LLC, Baton Rouge, LA (US)

(72) Inventor: Khushi L. Matta, Williamson, NY (US)

(73) Assignee: TumorEnd, LLC, Baton Rouge, LA (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/556,625

(22) Filed: Dec. 20, 2021

(65) Prior Publication Data

US 2022/0396823 A1 Dec. 15, 2022

Related U.S. Application Data

(63) Continuation of application No. 15/526,300, filed as application No. PCT/US2015/060350 on Nov. 12, 2015, now Pat. No. 11,203,776.

(60) Provisional application No. 62/078,811, filed on Nov. 12, 2014.

(51) Int. Cl.
*C12Q 1/48* (2006.01)
*A01N 43/04* (2006.01)
*C07H 15/04* (2006.01)

(52) U.S. Cl.
CPC ............... *C12Q 1/48* (2013.01); *A01N 43/04* (2013.01); *C07H 15/04* (2013.01); *G01N 2333/91091* (2013.01); *G01N 2400/12* (2013.01); *G01N 2400/38* (2013.01)

(58) Field of Classification Search
CPC .......... C12Q 1/48; A01N 43/04; C07H 15/04; G01N 2333/91091; G01N 2400/12; G01N 2400/38
USPC .......................................... 435/15
See application file for complete search history.

(56) References Cited

U.S. PATENT DOCUMENTS 11,203,776 B2 * 12/2021 Matta ..................... A01N 43/04
2006/0020127 A1 * 1/2006 Miura .................... A61Q 19/08
424/70.13

OTHER PUBLICATIONS

Brajeswar et al. S-, N-, and O-glycosyl derivatives of 2-acetamido-2-deoxy-D-glucose with hydrophobic aglycons as potential chemotherapeutic agents and N-acetyl-β-D-glucosaminidase inhibitors. Carbohydrate Research (1984), 126(1), 27-43. (Year: 1984).*
Knapp et al. Synthesis of α-GalNAc Thioconjugates from an α-GalNAc Mercaptan. J. Org. Chem. 2002, 67, 2995-2999. (Year: 2002 ).*

* cited by examiner

*Primary Examiner* — Yih-Horng Shiao
(74) *Attorney, Agent, or Firm* — FisherBroyles, LLP; Andrew K. Gonsalves

(57) ABSTRACT

Disclosed herein are glyco-decoy acceptor compositions that sidetrack or inhibit the activity of biosynthetic enzymes participating in synthesis of ligands binding at selectin, galectin and siglecs receptors; methods of their preparation and uses in drug discovery and in treatments of diseases.

1 Claim, 13 Drawing Sheets

Biantennary spacer-modified trisaccharide glycoside that mimics the biantennary Asn-linked core heptasaccharide acceptor.

| Structure | Name |
|---|---|
| 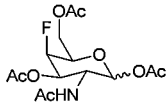 Molecular Weight: 349.31 | TE3030 1,3,6-Tri-O-acetyl 4-floro GalNAc |
| 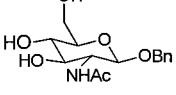 Molecular Weight: 311.33 | TE3033 GlcNac β-OBn |
| 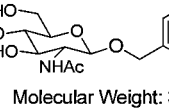 Molecular Weight: 355.43 | TE3034 GlcNAc β-O-Perillyl |
| 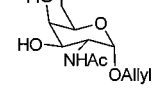 Molecular Weight: 261.27 | TE3035 GalNAc α-OAllyl |
| 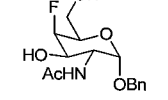 Molecular Weight: 313.32 | TE3037 4-floro GalNAc α-OBn |
| 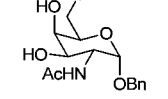 Molecular Weight: 311.33 | TE3039 GalNAc α-OBn |
| 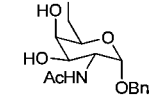 Molecular Weight: 313.32 | TE3040 6-floro GalNAc α-OBn |
| 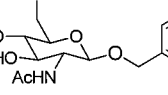 Molecular Weight: 375.42 | TE3041 6-O-Methyl GlcNAc β-ONAP |
| 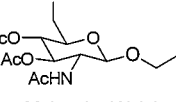 Molecular Weight: 487.50 | TE3042 3,4,6-Tri-O-acetyl GlcNAc β-ONAP |
| 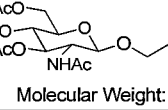 Molecular Weight: 481.54 | TE3043 3,4,6-Tri-O-acetyl GlcNAc β-O-perillyl |

FIG. 6

| Structure | Name |
|---|---|
| 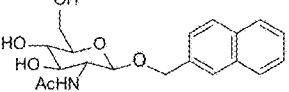 Molecular Weight: 361.39 | TE3044 GlcNAc β-ONAP |
| 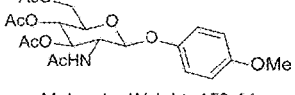 Molecular Weight: 453.44 | TE3045 3,4,6-Tri-O-acetyl GlcNAc β-O-*p*-methoxyphenyl |
| 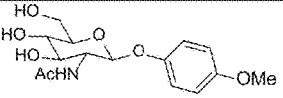 Molecular Weight: 327.33 | TE3046 GlcNAc β-O-*p*-methoxyphenyl |
| 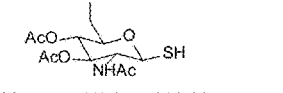 Molecular Weight: 363.38 | TE3047 3,4,6-Tri-O-acetyl GlcNAc β-thiol |
| 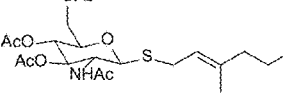 Molecular Weight: 499.62 | TE3048 3,4,6-Tri-O-acetyl GlcNAc β-thio-geranyl |
| 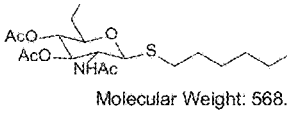 Molecular Weight: 568.52 | TE3049 3,4,6-Tri-O-acetyl GlcNAc β-thio-9-bromononane |
| 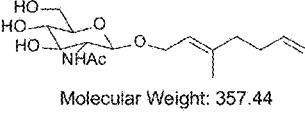 Molecular Weight: 357.44 | TE3050 GlcNAc β-O-geranyl |
| 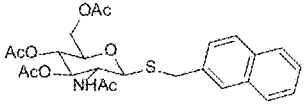 Molecular Weight: 503.56 | TE3051 3,4,6-Tri-O-acetyl GlcNAc β-thio-NAP |
| 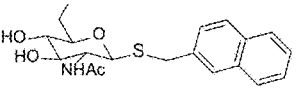 Molecular Weight: 377.45 | TE3052 GlcNAc β-thio-NAP |
| 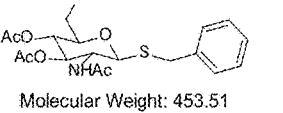 Molecular Weight: 453.51 | TE3053 3,4,6-Tri-O-acetyl GlcNAc β-thio-Bn |

FIG. 6 (cont'd)

| | |
|---|---|
| HO-, HO-, HO-, NHAc, S-geranyl<br>Molecular Weight: 373.51 | TE3054<br>GlcNAc β-thio-geranyl |
| OH, HO-, OH, NHAc, O-(CH2)6-N3<br>Molecular Weight: 346.38 | TE3055<br>GlcNAc β-O-6-azidohexane |
| NaO3SO, HO-, HO-, NHAc, OBn<br>Molecular Weight: 413.38 | TE3056<br>6-Sulfate GlcNAc β-OBn |
| OCH3, OH, OH, OH<br>Molecular Weight: 178.18 | TE4005<br>α-Methyl-L-fucoside |
| OBn, OH, OH, OH<br>Molecular Weight: 254.28 | TE4006<br>α-Benzyl-L-fucoside |
| OH, OH, HO-, NH, H3C-C(O)-, S-geranyl<br>Molecular Weight: 373.51 | TE-3503 |
| OH, OH, HO-, NH, H3C-C(O)-, S-cyclohexylmethyl<br>Molecular Weight: 333.44 | TE-3507 |
| AcO-, AcO-, AcO-, NHAc, S-, OH, OH, OH<br>Chemical Formula: $C_{20}H_{31}NO_{13}S$<br>Molecular Weight: 525.52 | TE5006<br>*33 mg* |
| AcO-, AcO-, AcO-, NHAc, S-, OAc, OAc, AcO, OAc<br>Chemical Formula: $C_{28}H_{39}NO_{17}S$<br>Molecular Weight: 693.67 | TE5007<br>*53 mg* |
| OAc, OAc, F, F, OAc<br>Chemical Formula: $C_{12}H_{16}F_2O_7$<br>Molecular Weight: 310.25 | TE5008<br>*19 mg* |

FIG. 6 (cont'd)

| Structure | Label |
|---|---|
| 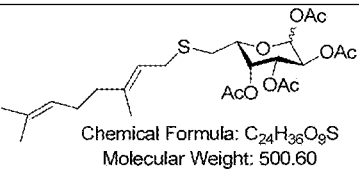<br>Chemical Formula: C₂₄H₃₆O₉S<br>Molecular Weight: 500.60 | TE5009<br>*31 mg* |
| 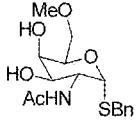<br>Molecular Weight: 341.4225 | TE3065 |
| 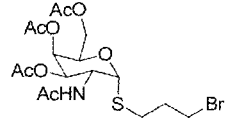<br>Molecular Weight: 484.3592 | TE3066 |
| 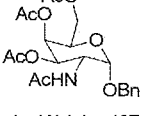<br>Molecular Weight: 437.4404 | TE3067 |
| 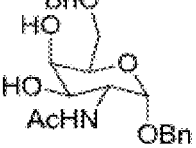<br>Molecular Weight: 401.4529 | TE3057<br>*23 mg* |
| 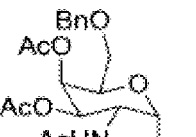<br>Molecular Weight: 485.5262 | TE3058<br>*27 mg* |
| 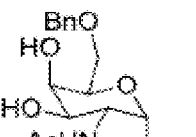<br>Molecular Weight: 351.3942 | TE3059<br>*19 mg* |
| 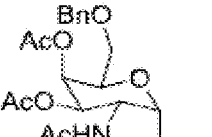<br>Molecular Weight: 435.4676 | TE3060<br>*23 mg* |
FIG. 6 (cont'd)

| | |
|---|---|
|  Molecular Weight: 361.3890 | TE3061<br>*21 mg* |
| 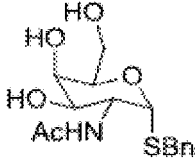 Molecular Weight: 327.3959 | TE3062<br>*18 mg* |
| 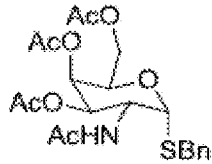 Molecular Weight: 453.5060 | TE3063<br>*23 mg* |
|  Molecular Weight: 377.4546 | TE3064<br>*18 mg* |
FIG. 6 (cont'd)

GalNAc Analogs

| ID | GalNAc α1- Thio Glycosides | Acetylated analogs (3,4,6 O acetyl) |
|---|---|---|
| TE3501 | GalNAc α-SH | TE3501Ac |
| TE3502 | GalNAc α-S-Ge | TE3502 Ac |
| TE3503 X=F<br>TE3504 X=OMe | X-6 GalNAc α-SH | TE3503 Ac<br>TE3504 Ac |
| TE3505 X=F<br>TE3506 X=OMe | X-6 GalNAc α-S-Ge | TE3505 Ac<br>TE3506 |
| TE3507 | GalNAc α→S(CH$_2$)$_3$S<br>GalNAc α↑ | TE3507 Ac |
| TE3509 X=F<br>TE3510 X=OMe | X-6GalNAc αS(CH$_2$)$_3$S<br>X-6GalNAc α↑ | TE3509 Ac<br><br>TE3510Ac |
| TE3511 X=OH<br>TE3511a X=F<br>TE3512 X=OMe | X-6GalNAc α →S(CH$_2$)$_6$S<br>X-6GalNAc α↑ | TE3511 Ac<br><br>TE3512 Ac |
| TE3516 X=F<br>TE3517 X=OMe<br>TE3518 X=OH | Galβ3 (X6-)GalNAc α-S-Ge | TE3516 Ac<br>TE3517 Ac<br>TE3518 Ac |
| TE3519 X=F<br>TE3520 X=OMe<br>TE3521 X=OH | Galβ3 (X-6)GalNAc α S(CH$_2$)$_3$S<br>Galβ3(X-6)GalNAc α↑ | TE3519 Ac<br>TE3520 Ac<br>TE3521 Ac |
| TE3522 X=F<br>TE3523 X=OMe<br>TE3524 X=OH | Galβ3 (X-6)GalNAc α →S(CH$_2$)$_6$S<br>Galβ3(X-6)GalNAc α↑ | TE3522 Ac<br>TE3523 Ac<br>TE3524 Ac |

FIG. 7A

GlcNAc Analogs

| ID | Table 1 Names of Decoys |
|---|---|
| TE3042 | 3,4,6-tri-O-Acetyl-GlcNAc-β-O-NAP |
| TE3043 | 3,4,6-Tri-O-acetyl GlcNAc β-O-Perillyl 5KP |
| TE3045 | 3,4,6-Tri-O-acetyl GlcNAc β-O-p-methoxyphenyl |
| TE3046 | GlcNAc β-O-p-methoxyphenyl |
| TE3047 | 3,4,6-tri-O-Acetyl-GlcNAc-β-S (Thio) |
| TE3048 | 3,4,6-tri-O-Acetyl-GlcNAc-β- S Ge (Geranyl) |
| TE3049 | 3,4,6-tri-O-Acetyl-GlcNAc-β- S-bromo-Oct |
| TE3050 Ac | 3,4,6-tri-O-Acetyl GlcNAc-β- O-Geranyl |
| TE3051 | 3,4,6-tri-O-Acetyl-GlcNAc-β-S-NAP |
| TE3052 | GlcNAc-β-S-NAP |
| TE3053 | GlcNAc-β- S- B (Benzyl) |
| TE3054 | GlcNAc-β- S Ge |
| TE3055 | GlcNAc β-O-6-azidohexane |

FIG. 8

COMPOSITIONS, METHODS AND TREATMENTS FOR INHIBITING CELL ADHESION AND VIRUS BINDING AND PENETRATION

CROSS-REFERENCE TO RELATED APPLICATIONS

This application is a continuation of U.S. patent application Ser. No. 15/526,300, filed May 11, 2017, which issued as U.S. Pat. No. 11,203,776 on Dec. 21, 2021, which is a U.S. National Phase filing under 35 U.S.C. § 371 of International Application No. PCT/US2015/060350, filed Nov. 12, 2015, and published as WO 2016/077567 A1 on May 19, 2016, which claims priority benefit of U.S. Provisional Patent Application Ser. No. 62/078,811, filed Nov. 12, 2014, the disclosures of which are hereby incorporated by reference herein in their entirety.

FIELD OF THE INVENTION

The present invention relates to the field of cell adhesion in cancer, inflammation immune dysfunction and infectious disease, including viruses; the receptor ligand molecular targets involved in those interactions; processes for identifying the most appropriate targets in a particular disease state; and compositions and methods for inhibiting those interactions to produce effective treatments. The later receptor ligand molecular interactions are causally involved in cell adhesion in inflammation and autoimmune diseases, as well as, in cancer cell metastasis and viral infections.

BACKGROUND OF THE INVENTION

Molecular biology, genetic engineering and monoclonal technologies have provided highly valuable molecular, therapeutic and clinical tools that have dramatically improved the understanding and treatment of diseases. Progress in genomics, epigenetics and proteomics at the DNA, RNA and protein levels has led to better understanding of disease processes. However, progress in glycomics has been excruciatingly slow.

The Glycome: Glycomics is the study of the fourth major cellular information source, i.e., the glycome which is the cellular carbohydrate constituents expressed on glycoproteins and glycolipids (the others being proteins, RNA and DNA). Slow to develop, because the biochemistry of glycosylation is extraordinarily complex with coordinately regulated linked enzyme systems that may involve ten to fifteen different individual enzymes.

Demonstrating the importance of the glycome, three separate reports in 1990 (22-24), followed by a fourth in 1991 (25), described the causal molecular processes involved in leukocyte adhesion to the endothelium in capillaries in inflammation. Those specific interactions were found to result from cell adhesive binding to blood vessel endothelial cells mediated by a single specific leukocyte selectin receptor known as leukocyte adhesion molecule ELAM-1. The interaction at the ELAM-1 receptor was found to be highly specific for sialyl-Lewis-X (sLe$^x$) polysaccharide, i.e., the natural endothelial ligand. As it is now understood, the latter most important selecting carbohydrate binding interaction serves as the molecular basis for mobilization of leukocytes into infected tissues in innate immunity, as well as, the aberrant inflammation in autoimmune disease states. (Citations appear below at the end of the Examples section.) Glycomics tools, while slow to emerge, have recently included elegant predictive mass spectrometry, NMR modeling and chemical synthesis of carbohydrate ligand libraries, including e.g. mimetics of sLe$^x$ and sialyl-Lewis-a (sLe$^a$). This has, for the first time, allowed more detailed structure-function studies and access to pharmacophore development using molecular pharmacology tools. The lead compounds, to date, have provided exciting new classes of anti-inflammatory small molecule drug compounds such as those identified by Magnani and coworkers (25), i.e., recently licensed by Pfizer for first uses in novel treatments of inflammatory sickle cell disease.

Cell Adhesins: Carbohydrates now known to be involved in important cell adhesion events include ligands binding at the following families of receptors: namely, selectins, siglecs, C-lectins, S-lectins, galectins and the like, (as disclosed further below in the accompanying disclosure). Importantly, the interactions of carbohydrates with these different receptors are intimately involved in a wide variety of natural physiologic processes including e.g. recognition of foreign invading pathogens by the innate immune system. As a result, effective candidate therapeutic antagonists acting at these receptors require an activity profile that is balanced to accommodate natural physiologic processes. Unfortunately, this balance can be difficult to achieve and failure can produce toxic side effects and adverse reactions limiting clinical uses. Thus, alternative therapeutic approaches are needed for interrupting key cell adhesive binding interactions.

Selectins: Selectins are a family of protein lectins related to ELAM-1, mentioned above, that mediate cell-cell adhesive interactions, e.g. leukocyte recruitment from the bloodstream into sites of tissue infection and disease. Now known to be involved in a variety of normal and pathological conditions, selectins have been grouped into three general molecular classes: namely, (1) L-selectin (e.g. CD62L), (2) E-selectin (e.g. CD62E) and (3) P-selectin (e.g. CD62P; 1-8).

Selectin Ligands: Natural ligands for selectins, decorated with carbohydrate ligand motifs, include the following: namely, Mucosal Addressin Cell Adhesion Molecule-1 (MAdCAM-1); Peripheral Node Addressin (PNAd); E-selectin ligand-1 (ESL-1 aka CD24); and intrinsic clotting factor von Willebrand factor (vWF). Other natural cellular selectin ligands include mucinous glycoproteins containing e.g. sulfate, fucose and/or sialic acid motifs. For example, sulfation is believed key to L-selectin bind of Glycosylation-dependent Cell Adhesion Molecule (GlyCAM-1), a proteoglycan involved in leukocyte-leukocyte binding interactions (1,9,10). Similarly, binding at P-selectin by its ligand mucin glycoprotein PDGL1 appears to involve sulfo-tyrosine residues, while binding at other selectins involves branched chain glycans O-linked at serine and threonine residues, i.e., Galβ3(GlcNAcβ6)GalNAcα-, which is referred to in the art as a Core-2 structure. N-linked glycans have also been implicated in selectin binding, e.g. E-selectin binding at CD44, a multifunctional glycoprotein often over-expressed in cancer cells (11-15).

Selectin-mediated adhesion: Selectin binding interactions play important roles in a broad range of normal and pathological conditions including e.g. innate and adaptive immune responses, cellular trafficking (e.g. leukocyte homing, lymphocyte trafficking), inflammation (neutrophil endothelial rolling, rolling arrest and trans-migration), ischemia-reperfusion injury (16), cell adhesion to extracellular matrix and cell metastasis in malignancy. Tumor cell adhesion to the vascular endothelium is mediated through selectin-carbohydrate interactions that likely play pivotal roles in metastatic spread of cancer and organ-specific predilections for certain tumor types, e.g. liver metastasis of colon carcinoma (17-21).

Antagonists capable of interrupting selectin-mediated binding interactions represent a most important new class of pharmaceuticals, particularly for uses in controlling inflammation and cancer metastasis. However, the complexities of cellular biosynthetic pathways and the difficulty synthesizing complex carbohydrate ligands have served to limit advances in this field. New alternative approaches are needed.

Biosynthesis of glycans: Glycoproteins are modified by addition of N-Acetyl-galactosamine (GalNAc) at serine and threonine hydroxyl residues (O-glycans) or N-Acetyl-glucosamine (GlcNAc) at asparagine (N-glycans). Subsequent addition of saccharide residues at the 2-, 3-, 4-, and 6-positions of GalNAc or GlcNAc can result in a wide variety of complex branched chain glycan structures. Modifications of different saccharide residues within the branched chain structures can result in extremely complex tree-like complex structures extending some distance from the cell surface. Further modifications with sulfo-residues can result in mucinous-like glycoproteins cross-linked by divalent salt bridges through their saccharide residues. There are various other families of glycans, e.g., glycolipids, Notch glycans and proteoglycans.

The present invention is directed to overcoming these and other deficiencies in the art.

SUMMARY OF THE INVENTION

Using detailed mapping of the biosynthetic enzyme-substrate specificities within tumor cells using "decoy" dead-end substrates, it has been possible for the first time to develop sophisticated predictive methods for the probable common biosynthetic pathways in cells leading to O- and N-glycan modifications e.g. of mucinous protein selectin ligands. At a basic level, this permits, for the first time, a more global approach to studying the contributions of different glycans to tumor cell binding interactions involved in growth, metastasis and immune evasion. The most fortunate byproduct of these studies is the discovery, disclosed herein, of small molecule cell-penetrable inhibitors of selectin ligand and other glycan biosynthesis. Unlike receptor-ligand antagonists, the instant compounds offer more global efficacy profile by targeted disruption of biosynthetic processes involved in multiple different tumor cell, inflammatory cell and viral adhesive interactions, e.g. E-, L- and P-selectins and others. By targeting biosysnthesis, and not receptor-ligand interactions, the disclosed methods offer a more balanced therapeutic profile of efficacy with lower expected toxicity and adverse reactions. Like anti-mitotic DNA-acting therapeutic compounds which have enjoyed 6 decades of clinical use, the platform technology provided by the instant invention now positions the field of glycobiology for a therapeutic renaissance.

Compositions and methods are provided for mapping and identifying the key cellular biosynthetic pathways, substrates, acceptors and intermediates involved in glycosylation of different cell adhesive ligands. Using panels of decoy dead-end substrates, the biosynthetic enzyme intermediates were predicted allowing rapid and detailed description of the enzyme-substrate relationships operative within individual populations of cells, including e.g. subsets of immune cells, cancer stem cells and metastatic cancer cells. Elucidation of the latter relationships provided the surprising discovery of small molecule cell-penetrable inhibitors of critical biosynthetic glycosylation pathways for selectin ligands, and virus glycoprotein coats. The instant compounds and methods find uses in controlling cell-cell adhesive binding interactions in a wide variety of disease processes including e.g. immune dysfunction, inflammation, cancer, and pathogen interactions.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 1A illustrates a partial biosynthetic from core 1 G1 and its modification by enzymes to give different glycan. The sites for Gal3Sulfo3 and Gal3Sulfo4 that modify core 2 G2Tetrascharide are also shown. Thus, biosynthetic pathways based on competition of enzymes for the same core substrates are shown in FIG. 1A, where cancer mutations have an ample set of opportunities to modify cell surfaces it can be said that relative expression of glycans α2fucosyl G1-f, sulfo3 G1-Su, G1-Sia, sialyl T antigen and naked T antigen Galβ3GalNAcα G1 in clinical specimens of patients may indicate the burden of disease, and the phase/grade of cancer.

FIG. 1B illustrates glycan analysis using hydrolases and peanut lectin in tandem.

determinants that are ligands on inflammatory immune cells and metastatic tumor cells for E-selectin receptors on vascular endothelial cells. Also shown is disruption of biosynthesis of a polylactosamine glycan chain by a decoy by diverting and disrupting the extension of biantennary N-glycans to tri- and tetra-antennary glycans. Polylactosamine glycans bind to galectins and such complex N-glycans constitute hallmarks of many cancer cells especially metastatic cells. Other analogs of decoys are shown in FIG. 8. As shown in FIG. 2, the underlying premise of the findings is that acceptor requirements for B4GalTs that incorporate Gal residues at GlcNAcβ chains in Trans Golgi are different. Our KP5 GlcNAcβO Perillyl and the thio decoys GlcNAcDSZ divert activity of β4GalT so that sialyl $Le^x$ like structures are formed on the decoy substrate (bottom scheme) rather than on the N-glycan in cells without decoys treatment (top schematic). MGAT5 is a key enzyme that forms the N-acetyl-lactosamine backbone on tri- and tetra-antennary N-glycans that bear the functional selectin-ligands and even ligand for galectins. Glycan analysis of the modified decoy products and native glycan treated with decoy should reveal the site of action of decoys. UDP-GlcNAc and Km values of GnTs enzymes are also indicated in the FIG. 2. MGAT5 requires more UDP-GlcNAc. As shown, our simple decoys (FIG. 8) block incorporation of Gal by B4GalT whose function is to extend the GlcNAcβ6Man chain generated by MGAT5 in tri and tetra antennary N-glycans. These decoys can block synthesis of the N-acetyl polylactosamine chain located on GlcNAc6Man, which functions as a ligand for galectins such as galectin1 and 3. Nomenclature: Glycans with x Mannose, y Galactose and z GlcNAc residues are called: MxGyGnz.

FIG. 6 is a table of chemical structures of illustrative decoy inhibitors of biosynthesis of O-glycans.

FIGS. 7A-7B is a table (FIG. 7A) and diagram (FIG. 7B) of GalNAcα 1-Thio analog acceptors and decoys. We took the advantage of easily accessible acetylated GalNAc-1-Thio [obtained by treatment of 2-acetamido 2 deoxy 1,3,4,6 tetra-O acetyl galactopyranoside (GalNAcβ acetate)] with Lawesson's reagent. This GalNAc-1-Thio was synthesized (as described in preparation of GlcNAcβSGe) (see FIG. 5) in 2 steps: (i) when reacted with geranyl bromide in presence of triethylamine in acetonitrile at room temperature followed by (ii) deacetylation gave TE3502. The GalNAcα thio derivative TE3501 was reacted with 1,3 dibromopropane and 1,6 dibromohexane separately under these conditions followed by deacetylation to give divalent derivatives TE3507 and TE3508, respectively, as shown in FIG. 7A.

FIG. 8 is a table of various GlcNAc analogs test in cell cultures of HL60. GlcNAcβ O analogs are in general written as GlcNAcβZ and GlcNAcDSZ. These compounds have been tested as decoys. The structures of some of these decoys are also displayed in FIG. 6. In certain tests, thioglycosides prove to be better than O-glycosides. For example, TE3054 with a S-geranyl gp blocks E-selectin binding function to HL-60 cells by 80% whereas the E-selectin binding of cells treated with the O-geranyl analog (TE3050Ac) is reduced by ~20%.

FIG. 9A: TE3030, 50 ug/mL; FIG. 9B: TE3048, 0.5 mg/mL; FIG. 9C: TE3054, 0.5 mg/mL; FIG. 9D: TE3065, 0.5 mg/mL; FIG. 9E: TE3066, 50 ug/mL; and FIG. 9F: TE3067, 0.5 mg/mL.

DEFINITION OF TERMS

Figure 1A:
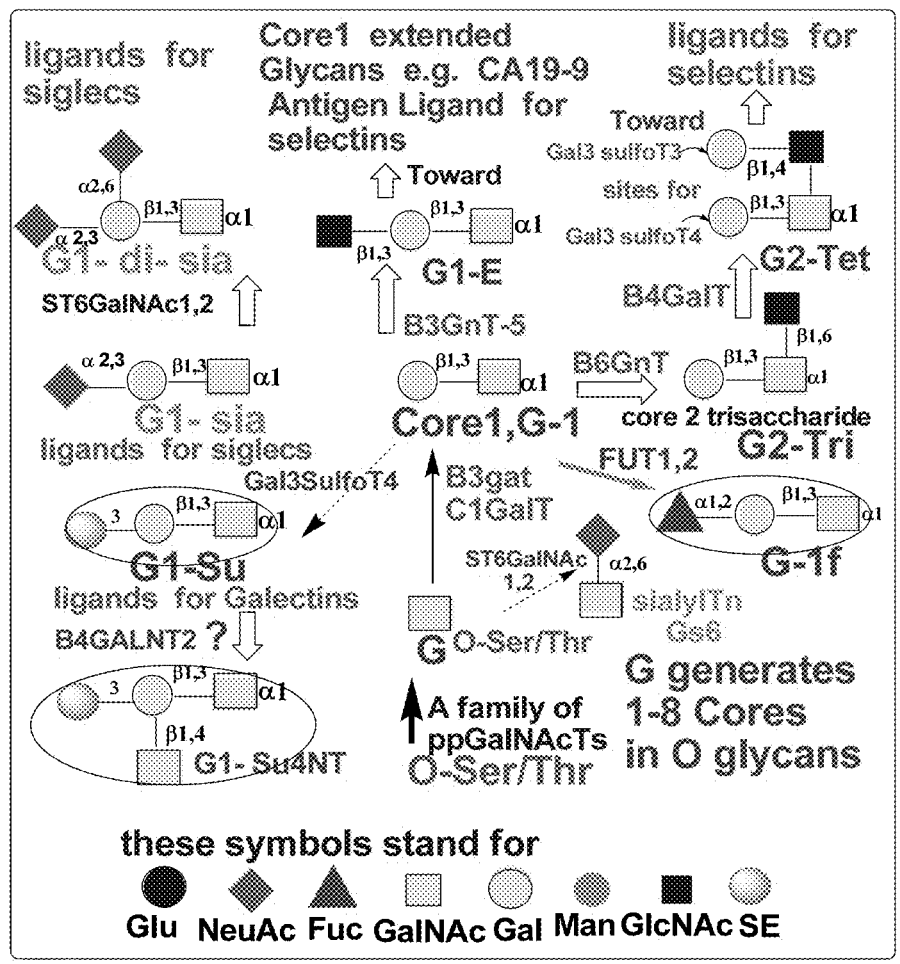
FIG. 1A is a diagram that illustrates carbohydrate structures for G1 core-1 decoy acceptor enzyme inhibitors, circled, and the enzymes and mucin synthetic pathways which they inhibit. Included are examples of the following decoy inhibitors of selectin ligand biosynthesis, as follows: (a) disaccharide inhibitor G6 (GlcNAc-β1,6-GalNAc) which is assembled by the B6GNT enzyme; (b) disaccharide G1-Sul (SulfoEster-Gal-β1,3-GalNAc) which is assembled by the Gal3SulfoT4 enzyme; (c) trisaccharide G1-f (Fuc-α1,2-Gal-β1,3-GalNAc) which produced by the FUT1,2 enzyme; and (d) trisaccharides G1-Sul4NT (GalNAc-β1,4-(SulfoEster)-Gal-β1,3-GalNAc) is acceptor for B4GALNT2 enzyme. Carbohydrate residues are as follows: namely, green ellipse (mannose, Man); blue rectangle (NAcetyl-glucosamine; GlcNAc); mustard ellipse (galactose, Gal); red diamond (sialic acid; NAc-neuraminic acid; NeuAc); green triangle (fucose; Fuc); empty rectangle (NAcetyl-galactosamine; GalNAc). More particularly.

Unless defined otherwise, all scientific and technical terms are understood to have the same meaning as commonly used in the art to which they pertain. For the purpose of the present invention, the following terms are defined below. Citations follow the EXAMPLES section, below.

Abbreviations

For sugar residues: Fuc, fucose; Gal, galactose; GalNAc, N-acetylgalactosamine; Glc, glucose; GlcNAc, N-acetylglucosamine; Man, mannose; NeuAc, N-acetyl neuraminic acid, Sia, sialic acid;

For substituents: A, allyl; F, fluoro; B, benzyl; Ge, geranyl; Me, methyl; NAP, 2-naphthylmethyl; P, perillyl; RE, Resveratrol; SE, sulfate ester;

For enzymes (for nomenclature of sialyl-transferases see, e.g. citations 57 and 0.58):
  (i) Ts, transferase; GTs and GlycoTs, glycosyl-transferases;
  (ii) FT and FUT, fucosyl-transferase aka fucosylTs;
  (iii) GalT and GalTs, galactosyl-transferase;
  (iv) GalNAcT and GalNAcTs, N-acetyl-galactosaminyl-transferase;
  (v) α-L-fucosylTs, α-L-fucosyl-transferase;
  (vi) GnT, N-acetyl-glucosaminyltransferase;
  (vii) SulfoT and SulfoTs, sulfo-transferase;
  (viii) SialylTs, sialyl-transferase;
  (ix) β3GalNAcTs and β3GALNT2, β3-NAc-galactosyl-transferase;
  (x) β4GalNAcTs and β3GALNT3&4, β4-NAc-galactosyl-transferase;
  (xi) βGalNAcTs, β-NAc-galactosaminyl transferase;
  (xii) GA3ST4, Gal-β1,3 sulfotransferase 4;

(xiii) GnTV (MGAT5), N-acetylglucosamyltransferase V;
(xiv) GNTIII (MGAT4), bisecting β1,4-NAcetyl-glucosaminyl-transferase-III;
(xv) Core-3 synthetase also known as β3Gn6, β1,3-NAcetyl glucosaminyltransferase-6;
(xvi) β3-Gn-T1, β1,3-NAcetylglucosaminyltransferase-1.

For Analytical Methods and reagents: mAbs, monoclonal antibodies; LC-MS, liquid chromatography mass spectrometry; MS, mass spectroscopy;

For selectins and ligands: CS, chondroitin sulfate; DS, dermatan sulfate; GAG, glycosaminoglycan; GLYCAM1, HS, heparin sulfate; L selectin ligand; PSGL-1, P-selectin glycoprotein ligand-1; sLe$^a$, sialyl-Lewis-A; sLe$^x$, sialyl-Lewis-X; Galectins for galactose binding lectins, and For glycan core structures: Core 1, Gal-β1,3-GalNAc-; Core 2, Gal-β1,3-(GlcNAc-β1,6)-GalNAcα-; Core 3, GlcNAc-β1,3-GalNAc-; Core 4, GlcNAc-β1,3-(GlcNAc-β1,6-)-GalNAc-; Core 5, GalNAc-β1,3-GalNAc-; Core 6, GlcNAc-β1,6-GalNAc-; and Core 7, GalNAc-α1,6-GalNAc-.

Definitions

Immune Dysfunction, used interchangeably with Autoimmune Disorder: is intended to mean a disease state in which a patient's immune system recognizes a self-antigen as foreign and mounts an immune response against that self-antigen with resulting tissue and/or organ damage. In certain cases, the disorder may result from a dysregulation of the immune system, e.g. a loss of tolerance to self-antigens, rather than recognition of the self-antigen as foreign. Dysregulated immune cells can secrete inflammatory cytokines which, in turn, promote systemic or local inflammatory reactions. Representative examples of autoimmune diseases include: Autoimmune hepatitis, Multiple Sclerosis, Myasthenia Gravis, Type I diabetes, Rheumatoid Arthritis, Psoriasis, Systemic Lupus Erythematosis, Hashimoto's Thyroiditis, Grave's disease, Ankylosing Spondylitis Sjogrens Disease, CREST syndrome, Scleroderma, inflammatory bowel disease, Crohn's disease, Ulcerative Colitis, Polyarteritis nodosa, Whipple's Disease, Primary Sclerosing Cholangitis and the like.

Cell: As used in reference to the instant glyco-decoy acceptor compositions and methods is intended to mean a mammalian cell having its standard scientific meaning, e.g. a nucleus containing genetic material enclosed within a cell membrane and containing cytoplasm and cellular organelles, mitochondria and the like. Representative cells according to the instant methods include cells in vitro tissue culture, as well as, cells in tissues and organs.

Cell surface marker: As used herein, means that the subject cell has on its cellular plasma membrane a specific protein or a carbohydrate expressed on, and identifying for, that subject cell, cell type or cellular population subtype. Representative cell surface markers include proteins and carbohydrates capable of binding to antibodies such as Cellular Determinant (CD)-specific antibodies, tissue-specific antigenic determinants, tumor-cell specific antigens, selectins and the like. Cell surface markers are recognized in the art to serve as identifying characteristics for particular types of cells and cell populations, and as such, find a wide variety of uses including cancer cell detection and immune cell characterization.

Compatible: The capability of operating with other components of a system. A decoy dead-end substrate which is compatible with a host cell is one which is capable of operating within the biosynthetic system operative in that host cell.

Di-saccharide: when used in regard to the instant glyco-decoy acceptor, is intended to mean an oligomeric assemblage of 2 sugar residues. Representative examples of disaccharides include homo-polymeric (e.g., maltose and cellobiose) and hetero-polymeric (e.g., lactose and sucrose) assemblages of sugars.

Disease: as used herein, is intended to have meaning as commonly recognized in the art, e.g. to designate the presence of signs and/or symptoms in an individual or patient that are generally recognized as abnormal. Representative diseases or conditions may be diagnosed and categorized based on pathological changes. Signs may include any objective evidence of a disease such as changes that are evident by physical examination of a patient or the results of diagnostic tests which may include, among others, laboratory tests to determine the presence of DNA sequence variances or variant forms of certain genes in a patient. Symptoms are subjective evidence of disease or a patient's condition, i.e. the patient's perception of an abnormal condition that differs from normal function, sensation, or appearance, which may include, without limitations, physical disabilities, morbidity, pain, and other changes from the normal condition experienced by an individual. Various diseases or conditions include, but are not limited to; those categorized in standard textbooks of medicine including, without limitation, textbooks of nutrition, allopathic, homeopathic, and osteopathic medicine. In certain aspects of this invention, the disease or condition is selected from the group consisting of the types of diseases listed in standard texts such as Harrison's Principles of Internal Medicine (14th Ed) by Anthony S. Fauci, Eugene Braunwald, Kurt J. Isselbacher, et al. (Editors), McGraw Hill, 1997, or Robbins Pathologic Basis of Disease (6th edition) by Ramzi S. Cotran, Vinay Kumar, Tucker Collins & Stanley L. Robbins, W B Saunders Co., 1998, or other texts described below. This application is directed particularly to diseases in which abnormal function of the immune system or the inflammatory response is part of the disease process, or in which modulation of immune or inflammatory function is being tested as a therapeutic intervention.

Disease Specific Target Oligonucleotide Sequence: is a gene or other oligonucleotide that encodes a polypeptide, most typically a protein, or a subunit of a multi-subunit protein that is a therapeutic target for a disease, or group of diseases. Representative examples include genes encoding polysaccharide synthesis enzymes cooperatively acting to produce selectin ligands.

Disease Criteria: is used herein to designate an indicator of a disease, such as a diagnostic factor, a prognostic factor, a factor indicated by a medical or family history, a genetic factor, or a symptom, as well as an overt or confirmed diagnosis of a disease associated with several indicators such as those selected from the above list. Representative disease criteria includes data describing a patient's health status, including retrospective or prospective health data, e.g. in the form of the patient's medical history, laboratory test results, diagnostic test result, clinical events, medications, lists, response(s) to treatment and risk factors, etc.

Galectin: are a family of cell membrane adhesion proteins defined by their binding specificity for β-galactoside sugars, such as N-acetyllactosamine (Galβ1-3GlcNAc or Galβ1-4GlcNAc), which can be bound to ligand proteins as either N-linked or O-linked glycosyl residues. They are also termed S-type lectins due to their dependency on disulphide bonds for stability and carbohydrate binding. 15 galectins have been identified in mammals encoded by LGALS genes, which have been numbered in a consecutive manner. Only galectin-1, -2, -3, -4, -7, -8, -9, -10, -12 and -13 have been identified in humans. Galectin-5 and -6 have been identified in rodents, whereas galectin-11, -14 and -15 are uniquely found in sheep and goats.

Glyco-decoy acceptor: when used herein in reference to the instant compositions and methods is intended to mean a modified substrate for a glycosyl transferase enzyme that i) acts as a substrate for the subject enzyme; ii) accepts a monosaccharide transferred by the subject enzyme; and iii) acts to inhibit biosynthesis of a protein-bound selectin, galectin or siglecs ligand in a cell. The instant glyco-decoy acceptor compounds are inhibitors of selectin, galectin and/or siglecs ligand synthesis in a cell, (defined supra), and thus represent compounds finding uses in vitro, e.g., in tissue culture, as well as, in vivo in treating a subject in need thereof.

Glycosyl transferase: when used herein in relation to the instant compositions and methods is intended to mean an enzyme functioning in a biosynthetic pathway of a selectin ligand, a galectin ligand or a siglecs ligand. Representative glycosyl transferases include e.g. B4GNT2; B3GNT-5; FUT1,2; B6GNT; B3GALT; B4GalT; Gal3SulfoT4; ST3; ST4; ST6; α-L-fucosyTs, α-L-fucosyl-transferase; β3GalNAcTs; β3GALNT2; β3-NAc-galactosyl-transferase; β4GalNAcTs; β3GALNT3&4; β4-NAc-galactosyl-transferase; βGalNAcTs, β-NAc-galactosaninyl transferase; GA3ST4; GnTV (MGAT5), N-acetylglucosamyltransferase V; FT, fucosyl-transferase aka fucosylTs; GalT and GalTs, galactosyl-transferase; GalNAcT and GalNAcTs, N-acetyl-galactosaminyltransferase; GTs and GlycoTs, glycosyl-transferases; GNTIII (MGAT3), β1,4-NAcetyl-glucosaminyl-transferase-III; core 3 synthetase also known as β3Gn6, β1,3-NAcetyl glucosaminyltransferase-6; β3-Gn-T1, β1,3-NAcetylglucosaminyltransferase-1; GnT, N-acetyl-glucosaminyltransferase; SulfoT and SulfoTs, sulfo-transferase; SialylTs, sialyl-transferase; and the like.

Healthy Individual: when used herein in relationship to a specified disease or disease criterion, is intended to mean that the subject individual does not exhibit the specified disease criterion or is not diagnosed with the specified disease.

Host: A cell, tissue or organism capable of accepting a decoy dead-end substrate without toxicity. Representative host cells include prokaryotic and eukaryotic cells, as well as cells within organs, tissues or organisms.

Monitoring: is when used herein to describe a process for collecting diagnostic information relevant to the health or disease status of a patient, is intended to mean the process of conducting one or more tests and compiling the data in a manner effective to provide useful information to a physician treating the patient. Representative examples of Monitoring include, determination of prognosis, risk-stratification, selection of drug therapy, assessment of ongoing drug therapy, prediction of outcomes, determining response to therapy, diagnosis of a disease or disease complication, following progression of a disease or providing any information relating to a patient's health status.

Selectin: Selectins (cluster of differentiation 62 or CD62) are a family of cell adhesion molecules (or CAMs) including L-, E-, and P-selectin. Selectins share a similar cassette structure: an N-terminal, calcium-dependent lectin domain, an epidermal growth factor (EGF)-like domain, a variable number of consensus repeat units (2, 6, and 9 for L-, E-, and P-selectin, respectively), a transmembrane domain (TM) and an intracellular cytoplasmic tail (cyto).

Siglecs: Siglecs (Sialic acid-binding immunoglobulin-type lectins) are cell surface adhesion proteins that bind sialic acid. Found on the surface of immune cells, they are a subset of the I-type (Ig type) lectins. 14 different mammalian Siglecs have been identified including e.g. Sialoadhesin (Siglec-1/CD169), a lectin-like adhesion protein on macrophages; CD22 (Siglec-2; a B cell surface protein involved in adhesion and activation); CD33 (Siglec-3) myelin-associated glycoprotein (MAG/Siglec-4); and Siglecs 5-12 (collectively referred to as "CD33-related Siglecs). Others such as Siglec-5 and Siglec-9 have homologues in mice and rats (Siglec-F and Siglec-E respectively in both). Humans have a higher number of Siglecs than mice and so the numbering system was based on the human proteins.

Oligosaccharide: when used in relation to the instant glyco-decoy acceptor, is intended to mean a polymeric assemblage of about 3 to about 10 constituent homo-monosaccharide sugars (i.e., all the same constituent) or hetero-monosaccharide (i.e., different constituent) sugars.

Subject in need thereof when used in reference to the instant therapeutic methods is intended to mean that a subject diagnosed, based on symptoms and/or laboratory tests, having a cellular, tissue and/or organ defect manifest as a disease symptom, criterion or condition, i.e. a subject having a disease. Representative diseases include genetic and autoimmune diseases, cancer, traumatic injury and the like as disclosed in greater detail below.

Substantially Purified: As used herein with regard to a composition of RPSC, "substantially purified" means that, with regard to the cells in the composition, fewer than 25% are of a type other than RPSC; preferably, fewer than 15% are of a type other than RPSC; more preferably, fewer than 10% are of a type other than RPSC; and, most preferably, fewer than 5% are of a type other than RPSC.

Sugar: is intended to mean a substituted or unsubstituted sugar residue having 3 carbon atoms (triose), 4 carbons (tetraose), 5 carbons (pentose), 6 carbons (hexose), 7 carbons (heptose), 8 carbons (octose) or 9 carbon atoms (nonose), as well as, interrelated straight chain, hemiacetal and acetal forms of a hexose sugar and aldosyl, furanosyl and pyranosyl forms. Representative examples of sugar residues include the following: namely, polyhydroxy $C_1$.aldehydes (e.g. aldoses polyhydroxy $C_2$ ketones: ketoses); polyols resulting from e.g., reduction of the $C_1$ aldehyde carbonyl to a hydroxyl (e.g., alditols) and reduction of the $C_2$ ketone of ketosesd; polyhdyroxy acids resulting e.g., from oxidation of the $C_1$ aldehyde and/or the chain terminal hydroxyl (e.g., aldonic, ketoaldonic, aldaric and ketoaldaric); amino-sugars resulting from replacement of any hydroxyl in the chain with an amino (e.g., aldosamines and ketosamines); aldehydo-acids resulting e.g. from oxidation of only the chain terminal hydroxyl in an aldehydo-sugar (e.g., uronic acids and keto-uronic acids); and their various lactones, i.e., cyclic esters of hydroxy carboxylic acids containing one 1-oxacycloalkan-2-one structure. The subject sugars may be straight chains and/or cyclic 3-, 4-, 5-, 6-, 7-, 8- and 9-membered sugar residues (e.g., hemiacetals and acetals) optionally substituted and linked with R-moieties. Representative triosyl residues include the aldoses D- and L-glyceraldehyde and derivatives thereof e.g., glyceraldehyde and glyceric acid phosphates; the keto-sugars meso-dihydroxyacetone and derivatives thereof. Representative tetraosyl residues include the aldoses D- and L-erythrose, threose, streptose and apiose; the keto-sugars D- and L-erythrulose; and derivatives thereof. Representative pentosyl residues include the D- and L-aldoses ribose, arabinose, xylose and lyxose; the D- and L-ketoses ribulose and xylulose; and, derivatives thereof. Representative hexosyl residues include aldosyl, furanosyl and pyranosyl sugars, e.g., cyclic and acyclic D- and L-aldoses such as allose, altrose, glucose, mannose, gulose, idose, galactose, talose, fructose, glucono-1,4-lactone, glucaro-1,4:6,3-dilactone, gluconofuranono-6,3-lactone; the ketoses ribo-hexulose, arabino-hexulolose, xylo-hexulose and lyxo-hexulose; and derivatives thereof. Representative 7-membered residues (i.e., heptosyl residues) include e.g., sedoheptulose and derivatives thereof; and, representative 9-membered residues (i.e., nonosyl residues) include N-acetylneuraminic acid and derivatives thereof. Also representative are, 2-deoxy-ribose, 6-deoxy-glucose and 2-deoxyglucose, xyloascorbyllactone, digitoxose (2-deoxyaltromethylose), fucose (6-deoxy-L-galactose), gluconolactone, galaconolactone, rhamnose (6-deoxy-mannose), fructose (2-keto-arabohexose), aldaric acids, alditols, aldonic acids, ketoaldonic acids, and amino sugars. Representative alditols include e.g., erythritol, threitol, ribitol, arabinitol, xylitol, lyxitol, glucitol, allositol, altrositol, mannositol, gulositol, idositol, galactositol, talositol and their derivatives. Representative aldonic acids include erythronic acid, threonic acid, ribonic acid, arabinonic acid, xylonic acid, lyxonic acid, gluconic acid, allonic acid, altronic acid, mannonic acid, gulonic acid, idonic acid, galactonic acid, tolonic acid and their derivatives. Representative ketoaldonic acids include erythro-tetraulosonic acid, threo-tetraulosonic acid, ribo-pentulosonic acid, arabino-pentulosonic acid, xylo-pentulosonic acid, lyxo-pentulosonic acid, gluco-hexulosonic acid, allo-hexulosonic acid, altro-hexulosonic acid, manno-hexulosonic acid, gulo-hexulosonic acid, ido-hexulosonic acid, galacto-hexulosonic acid, talo-hexulosonic acid and their derivatives. Representative aldaric acids include erythraric acid, threaric acid, ribaric acid, arabinaric acid, xylaric acid, lyxaric acid, allaric acid, altraric acid, glucaric acid, mannaric acid, gularic acid, idaric acid, galactaric acid, talaric acid and their derivatives. Representative of amino sugar include erythrosamine, threosamine, ribosamine, arabinosamine, xylosamine, lyxosamine, allosamine, altrosamine, glucosamine, N-acetylglucosamine, N-methlglucosamine mannosamine, gulosamine, idosamine, galactosamine, talosamine and their derivatives. Representative uronic acids include erythrosuronic acid, threosuronic acid, ribosuronic acid, arabinosuronic acid, xylosuronic acid, lyxosuronic acid, allosuronic acid, altrosuronic acid, glucuronic acid, mannosuronic acid, gulosuronic acid, idosuronic acid, galactosuronic acid, talosuronic acid and their derivatives. Representative keto-uronic acids include keto-erythrosuronic acid, keto-threosuronic acid, keto-ribosuronic acid, keto-arabinosuronic acid, keto-xylosuronic acid, keto-lyxosuronic acid, keto-allosuronic acid, keto-altrosuronic acid, keto-glucuronic acid, keto-mannosuronic acid, keto-gulosuronic acid, keto-idosuronic acid, keto-galactosuronic acid, keto-talosuronic acid and their derivatives. Representative lactones include erythrolactone, threolactone, ribolactone, arabinolactone, xyloslactone, lyxoslactone, allolactone, altrolacone, glucolactone, mannolactone, gulolactone, idolactone, galactolactone, talolactone and their derivatives. Preferably, the subject sugar comprises an aldose or ketose pentose or hexose sugar selected from the group consisting of D- and L-enantiomers of ribose, glucose, galactose, mannose, arabinose, allose, altrose, gulose, idose, talose and their substituted derivatives. Most preferably, the subject sugar comprises an aldose pentosyl or hexosyl sugar selected from ribose, glucose, galactose, glucosamine, galactosamine, N-acetylglucosamine, N-acetylgalactosamine, N-acetyl ribosamine, xylose, mannose and arabinose.

Tri-saccharide: when used in regard to the instant glyco-decoy acceptor, is intended to mean a polymeric assemblage of 3 sugar residues in accord with any of Formulas I-VIII.

DETAILED DESCRIPTION OF THE INVENTION

Embodiments of the invention provide qualitative and quantitative methods for mapping the critical polysaccharide biosynthetic enzymes involved in production of cell adhesive ligands including e.g. selectin, galectin and siglecs ligands engaged in cells of interest. Information obtained in this manner is useful for profiling gene expression (RNA or protein) in a variety of different cell types to identify the glycosylation pathways operative under different physiologic conditions e.g. of stress, low oxygen, high free radicals and/or in the presence of a pathogen. Representative cells useful for profiling include tumor cell clones, tumor stem cells, immune cells, endothelial cells and tissue and organ cells such as cardiac muscle, liver, kidney and lung cells. Representative methods for expression profiling, i.e., RNA or protein, are known in the art. The profile obtained in this manner is useful in patient diagnosis, e.g. to identify the most useful therapeutic biosynthesis inhibitor, as well as, in drug development, e.g. to identify a target compound pharmacophore for pharmaceutical development.

Pharmacophore Development: Embodiments of the invention provide methods and compositions useful for mapping and identifying the most critical polysaccharide synthesis enzymes, substrates, acceptors and intermediates acting cooperatively to produce cell adhesion ligands including e.g. selectin, galectin and/or siglecs glycosyl ligands operative in cell-cell adhesive binding interactions. The instant methods for mapping a plurality of polysaccharide synthesis enzymes acting cooperatively to produce a cell adhesion ligand, comprise the steps of:
(i) determining a polysaccharide structure of the subject ligand glycan;
(ii) selecting from within the subject polysaccharide structure a candidate enzyme acceptor and a candidate enzyme substrate residue;
(iii) testing a candidate cellular glycosyl transferase enzyme to determine whether the candidate enzyme substrate residue is added to the candidate enzyme acceptor through a catalytic activity of the enzyme;
(iv) determining that the candidate glycosyl transferase adds the candidate enzyme substrate residue to the candidate enzyme acceptor, thereby determining that the candidate glycosyl transferase is the cell adhesion ligand glycan glycosyl transferase;
(v) synthesizing a candidate glyco-decoy acceptor comprising a modified candidate enzyme acceptor;
(vi) testing the candidate glyco-decoy acceptor to determine whether it inhibits the addition of the candidate enzyme substrate residue to the candidate enzyme acceptor;
(vii) determining that the candidate glyco-decoy acceptor inhibits the addition of the candidate enzyme substrate residue to the candidate enzyme acceptor, thereby
(viii) determining that the candidate glyco-decoy acceptor is the cell adhesion ligand glyco-decoy acceptor;
wherein the glyco-decoy comprises a structure of Formulas I-VI, as set forth below. Representative candidate enzyme substrate residues include enzyme substrate terminal residues, e.g. fucose, galactose, glucose, GlcNAc, GalNAc residues; and enzyme substrate branch chain residues include e.g. fucose, sialic acid and sulfo-ester residues. Representative modified candidate enzyme acceptors, include those modified with a group such as an acetyl group, a perillyl alcohol group, a fluoro group, an allyl alcohol group, a sulfate ester; a benzyl alcohol group, a benzyl group, a methyl group, a naphthyl group, a limonene group, a farnesol group, a geraniol group, a perillyl group, a resveratrol group, a thio-glycoside group and a mono-terpene, a sesquiterpene group, a terpene-derived group and the like. Representative glycosyl transferases are defined above, e.g., sialyl transferases, fucosyl transferases, galactosyl transferases, glucosyl transferases, N-acetylglucosaminyl transferases, N-acetylgalactosaminyl transferases, sulfo-transferases, α-L-fucosyl transferases, β3GalNAc transferases, β4GalNAc transferases, GNTIII, β3Gn6, β3GNT1, GA3ST4, GNTV and the like.

Targeted Glycosylation Inhibitors: In other embodiments, the invention provides methods for predictive derivation of a cell adhesion ligand inhibitor, wherein the cell adhesion ligand comprises e.g. a selectin, galectin or siglecs ligand glycan that is a biosynthetic product of a cell produced by a plurality of glycosyl transferases and wherein the method comprises the steps of:

(i) determining a cell adhesion ligand glycan oligosaccharide sequence of a protein produced by the cell, wherein the protein is not the cell adhesion ligand;
(ii) selecting from within the glycan oligosaccharide sequence a terminal sugar residue selected from the group comprising a terminal fucose, a terminal sialic acid, a terminal sulfo-ester sugar, a terminal galactose, a terminal glucose, a terminal NAcetyl-glucosamine and a terminal NAcetyl-galactosamine;
(iii) synthesizing a profiling reagent comprising the terminal sugar residue chemically modified with a modifying agent selected from the group comprising an acetyl group, a perillyl alcohol group, a fluoro atom, an allyl alcohol group, a sulfate ester; a benzyl alcohol group, a benzyl group, a methyl group, a naphthyl group, a naphthylene group, a naphthyl-methyl group, a retinoic acid group, a retinol group, a resveratrol group, a limonene group, a farnesol group, a geraniol group, a thio-glycoside group and a mono-terpene, a sesquiterpene, an isoprenoid group and a terpene-derived group;
(iv) testing the profiling reagent and determining that it acts as a decoy acceptor to alter a first functional enzyme activity of a first glycosyl transferase enzyme, wherein the decoy acceptor is selected from a substrate effect and an inhibitor effect;
(v) testing a second functional enzyme activity of a second glycosyl transferase enzyme by adding the profiling reagent;
(vi) determining that the profiling reagent inhibits the second functional enzyme activity thereby establishing a functional relationship between the first glycosyl transferase and a second glycosyl transferase;
(vii) testing a selectin functional activity of the selectin ligand produced by the cell by adding the profiling reagent to the cell; and
(viii) determining that the profiling reagent inhibits the selectin functional activity in the cell thereby establishing that the first and the second glycosyl transferases participate in the biosynthesis of the selectin ligand in the cell and that the profiling reagent is the selectin ligand inhibitor.

Glyco-decoy Acceptor Compositions: Embodiments of the invention provide glyco-decoy acceptors which represent dead-end substrates inhibiting biosynthesis of cell adhesion ligands in a cell, e.g. selectin, galectin and siglecs ligands. The instant glyco-decoy acceptors are compatible with a variety of different cell types and find therapeutic uses, as well as, drug development uses, e.g. as pharmacophores. The instant compounds are useful in the methods of the invention for identifying the critical polysaccharide synthesis enzymes acting cooperatively to synthesize adhesive ligands in the cell. Representative cell adhesion ligands including those involved in mutant and dysfunctional cells and clones of cells having functional defects producing disease symptoms, criteria and conditions. The instant glyco-decoy acceptors comprise e.g. the instant compounds of Formulas I-VI as set forth in the organic structural formulas below.

The compound of Formula I is as follows:

Formula I

Biantennary spaceer-modified trisaccharide glycoside that mimics the biantennary Asn-linked core heptasaccharide acceptor.

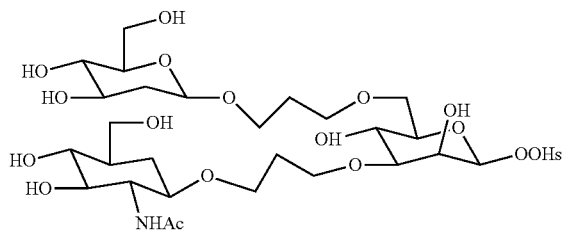

The compound of Formula II is as follows:

Formula II

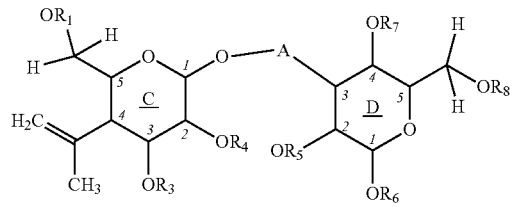

wherein $R_1$-$R_8$ are each independently selected from —H, —$CH_3$, —CHCH=$CH_2$, —CH($CH_3$)=$CH_2$, —$SO_3$; and A is $(CH_2)_x$, wherein x is an integer selected from 1, 2, 3 and 4, or A is absent and —O— is bonded with the $C_1$ position of ring C and the $C_3$ position of ring D.

The compound of Formula III is as follows:

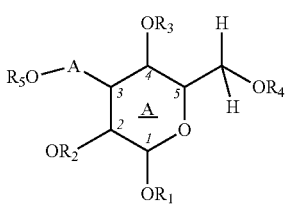

Formula III wherein, A̲ is a 6-membered glycosyl ring; A is $(CH_2)_n$, where n is an integer selected from 1, 2, 3, 4, 5 and 6; and $R_1$-$R_5$ are selected from —H, —F, -benzyl, -allyl, -allyl-alcohol, —$CH_3$, -acetyl, -perillyl, -naphthyl, -naphthylene-naphthyl-methyl, F, —$SO_3$, —$SO_2$, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group.

The compound of Formula IV is as follows:

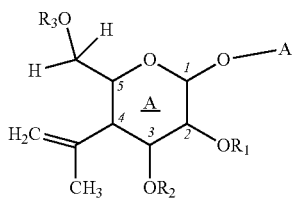

Formula IV wherein, A̲ is a 6 membered modified perillyl alcohol ring; A is selected from a monosaccharide, a disaccharide and a trisaccharide; and $R_1$-$R_5$ are selected from —H, —F, -benzyl, -allyl, -allyl-alcohol, —$CH_3$, -acetyl, -perillyl, -naphthyl, -naphthylene-naphthyl-methyl, F, —$SO_3$, —$SO_2$, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group.

The compound of Formula V is as follows:

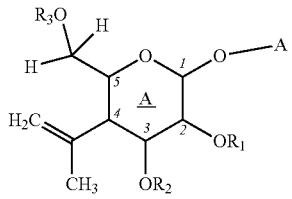

Formula V wherein, A̲ is a 6 member modified perillyl alcohol ring; A is selected from a monosaccharide, a disaccharide and a trisaccharide; and $R_1$-$R_3$ are selected from wherein $R_1$-$R_5$ are selected from —H, —F, -benzyl, -allyl, -allyl-alcohol, —$CH_3$, -acetyl, -perillyl, -naphthyl, -naphthylene-naphthyl-methyl, F, —$SO_3$, —$SO_2$, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group.

The compound of Formula VI is as follows:

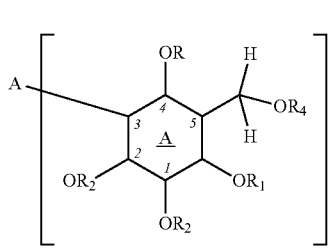

Formula VI wherein, A̲ is a 6 member glycosyl ring; A is selected from a monosaccharide, a disaccharide and a trisaccharide; and $R_1$-$R_4$ are selected from —H, —F, -benzyl, -allyl, -allyl-alcohol, —$CH_3$, -acetyl, -perillyl, -naphthyl, -naphthylene-naphthyl-methyl, F, —$SO_3$, —$SO_2$, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group.

Representative examples of the compounds of Formulas I-VI include the following: namely, (i) GlcNAcβ3-O, a GlcNAcβ4-O, a Gal-β3-GalNAc, a Gal-β4-GalNAc, a GalNAcβ3GlcNAcβ-O, a GalNAcβ4GlcNAcβ-O, a GalNAcβ6GlcNAcβ-O, a sulfo-ester-α3-Galβ3GalNAc, a sulfo-ester-α3-Galβ4GalNAc, a sulfo-ester-α3-Galβ3GlcNAc, a sulfo-ester-β3-Galβ4GlcNAc, a Galβ3 GlcNAcβ3Gal β3GalNAcα, a sulfo-ester-Galβ3(sulfo-ester-6-GlcNAc)βGalβ3GalNAcα-O, a sulfo-ester-Galβ4 (sulfo-ester-6-GlcNAc)βGalβ3GalNAcα-O, a sulfo-ester-Galβ3(Galβ4(SEGlcNAcβ)3GalNAcα-O, a sulfo-ester-Galβ3(GalNAcβ4GlcNAcβ)3GalNAc, a GlcNAcβ3(SE6Gal)β3SE6GalGalβXylo-O, a chondroitin sulfate and a dermatan sulfate;

(ii) GlcNAcβ-O—R; GlcNAcβ-R; GlcNAcβ3Galβ-O—R; GlcNAcβ3Gal-R; GlcNAcβ4Galβ-O—R; GlcNAcβ4Gal-R; GalNAcβ-O—R; GalNAcβ-R; Galβ3GalNAc—O—R; Galβ3GalNAc-R; Galβ3GlcNAc—O—R; Galβ3GlcNAc-R; Galβ4GlcNAc—O—R; Galβ4GlcNAc-R; Galβ4GalNAc—O—R; Galβ4GalNAc-R; Galβ4GlcNAc—O—R; Galβ4GlcNAc-R; GalNAcβ3GalNAc—O—R; GalNAcβ3GalNAc—O—R; GalNAcβ4GalNAc-R; Galβ3GalNAcβ3Gal-O—R; Galβ3GalNAcβ3Gal-R; Galβ3GalNAcβ4Gal-O—R; Galβ3GalNAcβ4Gal-R; Galβ4GalNAcβ3Gal-O—R; Galβ4GalNAcβ3Gal-R; GlcNAcβ2Manα-3Man0-O—R; GlcNAcβ2Manα3Man0-R; GlcNAc-β3-(GlcNAc-β6-Gal)β-O—R; GlcNAc-β3-(GlcNAc-β6-Gal)β-R; Galβ4(SE6-GlcNAc-6(Galβ3)GalNAcα-O—R, Galβ4(SE6-GlcNAc-6(Galβ3)GalNAcα-R; (GlcNAcβ2Manα6)(GlcNAcβ2Manα3)Manβ4Glc-NAcβ4GlcNAcβ-O—R (M3G0Gn4); (GlcNAcβ2Manα6)(GlcNAcβ2Manα3)Manβ4GlcNAcβ4GlcNAcβ-R; (GlcNAcβ2Manα6)(Gal4GlcNAcβ2Man3)Manβ-4GlcNAcβ4GlcNAcβ-O—R (M3G1Gn4); (GlcNAcβ-2Manα6)(Gal4GlcNAcβ2Man3)Manβ4GlcNAcβ4G-lcNAcβ-R; (Gal4GlcNAcβ2Manα6)(Gal4GlcNAcβ2Manα3)Manβ4GlcNAcβ4GlcNAcβ-O—R (M3G2Gn4); (Gal4GlcNAcβ2Manα6)(Gal4GlcNAcβ2Manα3) Manβ4GlcNAcβ4GlcNAcβ-R; (Gal4GlcNAcβ2 (GlcNAcβ6)Manα6)(Gal4GlcNAcβ2Manα3)

Manβ4GlcNAcβ4GlcNAcβ-O—R (M3G2Gn5); (Galβ4GlcNAcβ2(GlcNAcβ6)Manα6)(Gal4GlcNAcβ2Manα3)Manβ4GlcNAcβ4GlcNAcβ-R; (Gal4-GlcNAcβ2(Gal4GlcNAcβ6)Manα6)(Gal4GlcNAcβ2Manα3)Manβ4GlcNAcβ4GlcNAcβ-O—R (M3G3Gn5); (Gal4GlcNAcβ2(Gal4GlcNAcβ6)Manα6)(Gal4GlcNAcβ2Manα3)Manβ4GlcNAcβ-4GlcNAcβ-R;

wherein R is selected from —H, —F, -benzyl, -allyl, -allyl-alcohol, —CH₃, -acetyl, -perillyl, -naphthyl, -naphthylene-naphthyl-methyl, F, —SO₃, —SO₂, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group;

(iii) the selectin ligand glyco-decoys such as Galβ1,4GlcNAcβ1,6(Galβ1,3)GalNAcα1-O—R; Galβ1,3GlcNAcβ1,6(Galβ1,4)GalNAcα1-O—R; Galβ1,3GlcNAcβ1,6(Galβ1,3)GalNAcα1-O—R; Galβ1,4GlcNAcβ1,6(Galβ1,4)GalNAcα1-O—R; GlcNAcβ1,6(Galβ1,3)GalNAcα1-O—R; GlcNAcβ1,6(Galβ1,4)GalNAcα1-O—R; GlcNAcβ1,3Galβ1,3GalNAcα1-O—R; Galβ1,3GalNAcα1-O—R; Galβ1,4GalNAcα1-O—R; GlcNAcα-O—R; and GalNAcα1-O—R, i.e., where R is selected from —H, —F, -benzyl, -allyl, -allyl-alcohol, —CH₃, -acetyl, -perillyl, -naphthyl, -naphthylene-naphthyl-methyl, F, —SO₃, —SO₂, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group;

(iv) the galectin ligand glyco-decoys such as GalNAcβ1,4(SE3)Galβ1,3GalNAcα1-O—R; (SE3) Galβ1,3GalNAcα1-O—R; Galβ1,3GalNAcα1-O—R; GlcNAcα-O—R; and GalNAcα1-O—R, i.e., where R is selected from —H, —F, -benzyl, -allyl, -allyl-alcohol, —CH₃, -acetyl, -perillyl, -naphthyl, -naphthylene-naphthyl-methyl, F, —SO₃, —SO₂, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group; and, (v) the siglecs ligand glyco-decoys such as NeuAcα2,3Galβ1,3(NeuAcα2,6)GalNAcα1-O—R; NeuAcα2,3Galβ1,3GalNAcα1-O—R; Galβ1,3GalNAcα1-O—R; GlcNAcα-O—R; and GalNAcα1-O—R; i.e., where R is selected from —H, —F, -benzyl, -allyl, -allyl-alcohol, —CH₃, -acetyl, -perillyl, -naphthyl, -naphthylene-naphthyl-methyl, F, —SO₃, —SO₂, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group.

Cell Penetrability: Compounds according to the invention are provided with cell penetrability for effective inhibition of intracellular glycosylation biosynthetic enzymes. Cell penetrability is advantageously conferred by one or more of the following R-group radicals: namely, —F, -benzyl, -allyl, -allyl-alcohol, —CH₃, -acetyl, -perillyl, -naphthyl, -naphthylene-naphthyl-methyl, F, —SO₃, —SO₂, —SH, -resveratrol, -limonene, -perillyl alcohol, -benzyl alcohol, -benzyl, -farnesol, geraniol, -thio-glycoside, -mono-terpene, -sesquiterpene, -isoprenoid-derived group and -terpene-derived group.

Use in Therapy or Drug Development: The choice of glyco-decoy acceptor of the instant invention is of course at the discretion of the physician, scientist and/or patient and will vary depending upon at least the cell type, medical condition, age, location where the treatment is to be administered. Representative examples of therapies, and targeted drug development, using the instant methods include treatments for at least the following: namely, inflammatory and autoimmune diseases, include treatments for e.g. age-related macular degeneration, (both the wet and dry forms); type-1 insulin-dependent diabetes mellitus (IDDM); Crohn's and inflammatory bowel disease; systemic lupus erythematosus (SLE); Sjogren's disease; multiple sclerosis; myasthenia gravis; cystic fibrosis and the like. Representative examples of therapies using the instant methods for treating cancers and metastatic disease, include treatments for e.g. carcinomas, sarcomas, neuro-endocrine tumors and the like. Common medical practice (at present) is chemotherapy, radiation and possible surgical intervention. In this context, uses of the instant glyco-decoy acceptor therapeutic compositions include therapies designed to limit metastatic spread, as well as, those designed to promote the efficacy of chemotherapy and radiation.

Those familiar with drug use in medical practice will recognize that regulatory approval for drug use is commonly restricted to clinical indications for which beneficial effects were demonstrated in controlled clinical trials. Unfortunately, it has generally not been possible with current knowledge to predict which patients will have a beneficial response, with the exception of certain diseases where suitable laboratory methods have been developed. Likewise, it has generally not been possible to determine in advance whether a drug will be safe in a given patient. Recently it has become apparent that certain test results may be used to determine the efficacy of drugs in particular patients. In these settings the diagnostic test is referred to in the art as a Companion Diagnostic Product. Regulatory approval for the use of most drugs is limited to the treatment of selected diseases and conditions. The descriptions of approved drug usage, including the suggested diagnostic studies or monitoring studies, and the allowable parameters of such studies, are commonly described in the "label" or "package insert" which is distributed with the drug. Such labels or package inserts are preferably required by government agencies as a condition for marketing the drug and are listed in common references such as the Physician's Desk Reference (PDR).

Embodiments of the invention provide Companion Diagnostic Product methods for determining which patients may benefit from therapy with inhibitors of the interaction between sialyl-Lewis$^a$ ligand and E-selectin receptors in inflammatory and autoimmune diseases and in cancers.

In reference to response to a treatment, the term "tolerance" refers to the ability of a patient to accept a treatment, based, e.g., on deleterious effects and/or effects on lifestyle. Frequently, the term principally concerns the patient's perceived magnitude of deleterious effects such as nausea, weakness, dizziness, and diarrhea, among others. Such experienced effects can, for example, be due to general or cell-specific toxicity, activity on non-target cells, cross-reactivity on non-target cellular constituents (non-mechanism based), and/or side effects of activity on the target cellular substituents (mechanism based), or the cause of toxicity may relate to immune activation.

Embodiments of the invention provide methods for determining the tolerance of patients to accept a treatment with an instant glyco-acceptor compound that inhibits the cellular synthesis of a cellular ligand bound by a cell adhesion receptor on the surface of a target cell, e.g. a selectin, a galectin or a siglecs receptor on an immune or a cancer cell; and, without exerting a negative physiological toxic or apoptotic effect on the target cell in the patient. Adverse toxic and apoptotic cellular responses to drugs constitute a major medical problem. The instant glyco-decoy acceptor compounds and embodiments of the invention overcome these obstacles in the clinical arts. Rather than targeting extracellular receptor-ligand interactions the instant compounds act at an intracellular level, like traditional chemotherapeutic agents, to disrupt synthesis of disease promoting cellular ligand proteins.

Embodiments of the invention provide methods for profiling cellular glycosyl transferases to provide diagnostic methods for predicting which of the instant compounds is most useful as a therapeutic in a particular patient, i.e., personalized medicine. The exercise of the latter methods provides basis for improved efficacy at lower doses with resultant lower toxicity and increased drug safety.

The route of delivery according to the instant methods for the instant glyco-decoy acceptor drug therapy is determined by the disease and the site where treatment is required. For topical application, it may prove desirable to apply the instant compositions of Formulas I-VI (supra) at the local site, e.g., by placing a needle into the tissue at that site or by placing a timed-release implant or patch, and/or by administering the drug in an ointment, cream, lotion, aerosol spray or skin-penetrating formulation; while in a more acute disease clinical setting it may prove desirable to administer the instant compositions systemically. For other indications the instant compositions may be delivered by intravenous, intraperitoneal, intramuscular, subcutaneous and intradermal injection, as well as, by intranasal and intrabronchial instillation (e.g., with a nebulizer), transdermal delivery (e.g., with a lipid-soluble carrier in a skin patch), or gastrointestinal delivery (e.g., with a capsule or tablet). The preferred therapeutic compositions for inocula and dosage will vary with the clinical indication. The inocula may typically be prepared from a frozen solution or a lyophilized powder resuspended in a physiologically acceptable diluent such as saline, phosphate-buffered saline or water for injection. Some variation in dosage will necessarily occur depending upon the condition of the patient being treated, and the physician will, in any event, determine the appropriate dose for the individual patient. Since the pharmacokinetics and pharmacodynamics of the instant compositions will vary somewhat in different patients, the most preferred method for achieving a therapeutic concentration in a tissue is to gradually escalate the dosage and monitor the clinical effects. The initial dose, for such an escalating dosage regimen of therapy, will depend upon the route of administration.

The instant compositions of Formulas I-VI, supra, may be administered alone or in combination with one or more pharmaceutically acceptable carriers, e.g. in either single or multiple doses. Suitable pharmaceutical carriers may include inert biodelivery gels or biodegradable semi-solid matrices, as well as, diluents or fillers, sterile aqueous solutions and various nontoxic solvents. The subject pharmaceutically acceptable carriers generally perform three functions: namely, (1) to maintain and preserve the active ingredient in the instant composition; (2) to retain the active ingredient at a tissue site; and, (3) to improve the ease of handling of the instant composition by a practitioner, e.g., to improve the properties of an injectable composition or the handling of a surgical implant. The pharmaceutical compositions formed by combining an instant composition with a pharmaceutically acceptable carrier may be administered according to the instant methods in a variety of dosage forms such as syrups, injectable solutions, and the like. The subject pharmaceutical carriers can, if desired, contain additional ingredients such as flavorings, binders, excipients, and the like. For certain gastrointestinal procedures it may be desirable to encapsulate the instant cellular composition to protect the active ingredient during passage through the stomach, e.g., in hard-filled gelatin capsules. For this purpose capsules might additionally include additives such as lactose or milk sugar and/or polyethylene glycols as cellular preservatives. For parenteral administration according to the instant methods, solutions may be prepared in sesame or peanut oil or in aqueous polypropylene glycol, as well as sterile aqueous isotonic saline solutions. The subject aqueous solution is preferably suitably buffered if necessary and the liquid diluent first rendered isotonic with sufficient saline or glucose. Such aqueous solutions of instant composition may be particularly suitable for intravenous, intramuscular, subcutaneous, and intraperitoneal injection.

The subject sterile aqueous media employed are obtainable by standard techniques well known to those skilled in the art. For use in one or more of the instant methods, it may prove desirable to stabilize an instant composition, e.g. to increase shelf life and/or half-life. Methods for preserving, storing, shipping and preserving solutions are known in the art. Improving the shelf-life stability of compositions, e.g., at room temperature or 4° C., may be accomplished by adding excipients such as: a) hydrophilic agents (e.g., glycerol); b) non-linked sugars (e.g., sucrose, mannose, sorbitol, rhamnose, xylose); c) complex carbohydrates (e.g., lactose); and/or d) bacteriostatic agents or antibiotics.

The preferred pharmaceutical compositions of Formulas I-VI, supra, for inoculum and dosage will vary with the clinical indication. The inoculum may typically be prepared from a concentrated solution by the practicing physician at the time of treatment, e.g., by thawing and then diluting a concentrated frozen suspension in a storage solution into a physiologically acceptable diluent such as phosphate-buffered saline or water for injection. Some variation in dosage will necessarily occur depending upon the condition of the patient being treated, and the physician will, in any event, determine the appropriate dose for the individual patient.

The effective amount of the instant composition per unit dose depends, among other things, on the body weight, physiology, and chosen inoculation regimen. A unit dose of the instant composition refers to the micrograms or milligrams of compound in the subject suspension. Single unit dosage forms and multi-use dosage forms are considered within the scope of the invention, as disclosed further below.

For treatments of local dermal and cosmetic clinical indications designed e.g. to limit post-surgical inflammation and scarring, the instant composition of Formulas I-VI, (supra), may be provided in an emollient cream or gel. Representative examples of non-toxic cell-preservative emollient pharmaceutically acceptable carriers include oil-in-water and water-in-oil emulsions, i.e., as are known to those skilled in the pharmaceutical arts.

In alternative embodiments, the invention provides different routes for delivery of the instant compositions, of Formulas I-VI (supra), as may be suitable for use in the different disease states and sites where treatment is required. For topical, intrathecal, intramuscular or intra-rectal application it may prove desirable to apply the subject active pharmaceutical ingredients in a preservative salve, ointment or emollient pharmaceutical composition at the local site, or to place an impregnated bandage or a dermal timed-release lipid-soluble patch. For intra-rectal application it may prove desirable to apply the instant compositions, e.g. in a suppository. In other embodiments, for pulmonary airway restoration, regeneration and rejuvenation it may prove desirable to administer the instant compositions by intranasal or intrabronchial instillation (e.g., as pharmaceutical compositions suitable for use in a nebulizer). For gastrointestinal regenerative medicine it may prove desirable to administer the instant compositions by gastrointestinal delivery (e.g., with a capsule, gel, trouch or suppository). Also contemplated are suppositories for urethral and vaginal use in regenerative medical treatments of infertility and the like. In one preferred embodiment, the instant pharmaceutical compositions are administered via suppository taking advantage of lectin-mediated, e.g. adhesin and selectin-mediated, uptake and transport into the blood stream in a timed-release type manner. The instant methods, i.e., employing the instant compositions of Formulas I-VI, supra, make it feasible to administer therapy in a multi-dosage form, e.g. via an implantable mini-pump (such as used for delivery of insulin in patients with Type 1 insulin-dependent diabetes mellitus). Alternatively, in other cases it may desirable to deliver the instant compositions over a longer period of time, e.g., by infusion.

In certain alternative embodiments, the method may involve administration of an intravenous bolus injection or perfusion of the instant compositions of Formula I-VI, supra, or may involve administration during (or after) surgery e.g. to remove a tumor, or a prophylactic administration after surgery to minimize metastatic spread. In certain other embodiments, the instant administration may involve a combination therapy, e.g., the instant composition and a second drug, e.g., an anti-coagulant, anti-infective or radiation sensitizing agent. Alternatively, the instant combination therapy may involve administration of the instant composition with cells, e.g. in conjunction with a dendritic cell tumor vaccine.

The route of delivery of the subject preparations, according to the instant methods, determined by the particular disease. For topical application it may be useful to apply the instant compositions at the local site (e.g., by injection, while for other indications the preparations may be delivered by intravenous, intraperitoneal, intramuscular, subcutaneous, intranasal, and intradermal injection, as well as, by transdermal delivery (e.g., with a lipid-soluble carrier in a skin patch placed on the skin), or even by oral and/or gastrointestinal delivery (e.g., with a capsule, tablet or suppository). Acetylated derivatives of the sugars are membrane-penetrating and intracellular esterases will remove the acetyl groups, to provide the free sugar as a decoy.

In certain embodiments, this invention claims the use of analogs of GlcNAc, GlcNAcβ-O—R, GlcNAcβSR, GlcNAcβ-R(C—C linkage), and GlcNAcβ-R(NH, NHCOX, where X can be any extension alkyl, benzoate, $CF_3$, alkenyl or other arm). R can be any natural product, e.g., retinyl, resveratrol moiety, curcumin moiety, taxtol moiety and others) or synthetic unit. The claim is that a GlcNAc analog that acts as acceptor for GalT's, the compound and its acetylated compounds are decoys.

Similarly, in GalNAc analogs, GalNAcα-O—R, GalNAcα-R(C—C linkage) and GalNAcα-R(NH, NHCOX, where X can be any extension alkyl, benzoate, $CF_3$, alkenyl or other arm). $NHCOCH_3$ could be replaced by azide if the compound acts as acceptor for Galtransferase. R can be any natural product, e.g., retinyl, resveratrol moiety, curcumin moiety, taxtol moiety and others) or synthetic unit. The claim is that a GalNAc analog that acts as acceptor for enzymes that extend different core structures, 8 so far known, the compound and it acetylated compounds are decoys. This invention especially claims that combines use of decoys from the following list can arrest the virus. It can provide N glycans glycoprotein mostly free of O glycans, such as GP120 or other natural recombinant glycoproteins.

EXAMPLES

The following examples are intended to illustrate particular embodiments of the present invention, but are by no means intended to limit the scope of the present invention. While illustrated in the Examples section, below, those of ordinary skill in the art will recognize that the instant disclosure enables similar compositions to be developed from alternative starting materials and intermediates.

Example 1

Glycan Signatures: Development of Predictive Methods

An innovative approach toward identifying glycan signatures for diagnosis and treatment efficacy: Much effort has been directed toward studies of genomics and proteomics with resultant improvements in cancer diagnosis and treatment. The fourth cellular molecular source of selectivity and specificity, besides DNA, RNA and protein, is the glycome. Poised at the outer most portions of the cellular architecture, glycoproteins and proteoglycans in the extracellular matrix are largely responsible for the adhesive characteristics of cells, particularly in tissues, as well as, critical cell sorting and movement in development. Since pioneering studies identified fundamental changes in tumor cell glycans and glycolipids, investigators have struggled to understand the functional consequences. The complexity of glycosylation is now well appreciated. Coordinately-regulated linked cooperative enzyme systems form the basic synthesis pathways which often comprise ten to fifteen different enzymes. These multiple enzymes act stepwise in the biosynthesis of complex and branched chain polysaccharides that post-translationally modify cell surface glycoproteins. Other enzymes participate further modify the resultant glycans. While core O- and N-glycan structures have now been identified, the extensive anomeric complexity of branched chain glycan structures is also appreciated. Unfortunately for those involved in drug discovery and development, it is also now well appreciated that even relatively minor changes in oligosaccharide species can contribute significantly to altered cell function, most particularly as those structural alterations affect functional processes of adhesion, intercellular recognition and signaling.

Determining carbohydrate structures for minor highly variable membrane species is vastly more difficult than protein or DNA sequencing. As a result, progress in elucidating the glycome has moved more slowly. Tools to evaluate cellular expression patterns have included the frequent use of selective probes, such as lectins and antibodies. Unfortunately, results with probes have often proven misleading and even incorrect.

Glycome recognition: Mammalian cells recognize one another and foreign invaders by virtue of carbohydrate recognition proteins, e.g. by endogenous lectins and receptor proteins referred to also as pattern recognition receptors (PRR). Natural mammalian lectins have exquisite specificity for both the composition and anomeric structure of mammalian, bacterial, fungal and parasitic glycans. Involved in both embryonic development and immune protection, evolutionary advantage is obviously compelling and mammalian genomes are now known to contain large numbers of such protein lectins. The selectins, one such lectin class, act as important neutrophil adhesion receptors. Advances in understanding the role of selectins have been hampered by both the biosynthetic complexity and variability of their carbohydrate ligands. Achieving a better understanding of the cellular biosynthetic mechanisms is key to achieving improved diagnostics and therapeutics.

The Glycome in Cancer: Many important questions remain unanswered, including, for example, the following: (1) Are cell surface structural changes in glycans in tumor cells related in any way to invasive and/or metastatic properties of the cells? (2) Alternatively, are structural changes in glycans in tumor cells adventitious, e.g, resulting from a mutation or epigenetic change that results in an altered Golgi function which, in turn, results in a change in glycosylation?; (3) Is the cancer functional phenotype related to cell surface glycans, and if so, how?; (4) For clones of cancer stem cells, are glycan changes clonal or can glycosylation changes occur within the cell population making up the clone?; (5) Are there glycosylation traits in cancer stem cells that can be selected-for or -against by the immune system and the tumor microenvironment?; (6) Do changes in individual members of a cancer stem cell clone confer any advantageous effects that might favor metastatic spread?; and (7) What changes relate structure to particular cellular functions that might be useful in designing new generations of diagnostics, therapeutics or targeted drug delivery agents?

Answers to these most important questions require accuracy in mapping tumor cell glycans and their interactions with host lectins.

Predictive Glycomics: Because of complex inter-related synthetic pathways and variability in substrate utilization, it has, often not been possible to predict the pattern of oligosaccharide cell adhesion ligands expressed on any cell surface with any degree of certainty. Disclosed below are comprehensive integrated methods, constituting an overall "predictive strategy", that can be systematically used to profile patterns of oligosaccharide cell adhesion ligands in cells. The instant methods involve novel approaches to profiling glycosyl enzymes, (a shift from other present day strategies), resulting in derivation of cellular "glycan signatures", also referred to herein interchangeably as "glycan maps". The latter signatures or maps can, in turn, be used to diagnose the malignant phenotype of a cancer stem cell; the trafficking pattern for an autoimmune T- or B-cell lymphocyte clone; or to predict the best therapeutic agent to disrupt the adhesion of those cells to vascular endothelial cells.

Functional Predictive Glycomics: To illustrate the inherent complexity of cellular oligosaccharide structures, O-glycans can be built on a Core-1 backbone comprising Gal-β3-GalNAc-α-Ser/Thr (designated hereinafter "G1"), as represented in FIG. 1A. In the biosynthesis of G1 O-glycans, the first sugar sequence GalNAc-α-O-Ser/Thr, (G), (also known as Tn antigen), can form the core of at least eight different known derivative structures; where each of the different structure results from the biosynthetic activity of a different panel of enzymes; and where each different structure has its own unique endogenous lectin receptor and its own functional role in cell physiology. As set forth further below, changes in cellular glycan profiles can be used to predict health, disease, severity of disease, response to therapy and/or progression or regression of malignancy. For example, mucin is one of the resultant G1 glycan signatures, (described in further detail below) and it's with expression on the cell surface of a tumor cell significantly alters cell adhesion and immune recognition by macrophages and dendritic cells, as well as, killing by cytotoxic T-lymphocytes (CTL) and antibodies.

Predictive Strategies: A general overview is provided first, followed in the following Examples (below) with specific compositions and methods.

Unifying principles, disclosed and claimed herein, can be applied to the solution of a cellular glycan profile. For instance, all of the different diverse biosynthetic pathways involved in mucin synthesis from G1 core structures must compete: i) for Core-1 substrate; and ii) for a limited selection of key enzymes (FIG. 1A). Thus, as a first predictive principle, involves understanding the competitive landscape operative in a cell.

As a second predictive principle, biosynthetic options for core-extension must be understood in different tissues, i.e., key among which is substrate specificity and tissue-specific expression profiles for key biosynthestic enzymes. For instance, continuing with the G1 core example (supra), the G1 core structure can be extended in different cells with: i) sialic acid addition to produce G1-s, (NeuAc-α2,3-Gal-$R_3$-GalNAc-α-) and/or ii) disialo-G1 (G1-di-s); or iii) in certain tissues G1 can be extended with N-Acetyl-glucosamine to produce GlcNAc-β3-Gal-β3-GalNAc-α-(G1-e); and/or iii) core G1 can be modified in other tissues by Gal-3-Sulfo-T4 to give SE-3-Gal-β3-GalNAc-α-(G1-Su). Such core extended carbohydrate epitopes are found in advanced stages of cancer where loss of B4GALNT enzyme activity leads to the product SE-3-Gal-β-GalNAc-α-(G1Sul) rather than G1Sul-4NT glycan, which is found in aged healthy normal tissues.

As a third predictive principle, ligand binding at lectins must be understood. Continuing the core G1 example (supra) still further, both G1-s and G1-di-s are ligands binding at Siglecs, a family of sialic acid binding lectins; and in certain tissues the extension of the G1-e structure can result in complex higher glycans such as CA19-9, a tumor associated antigen expressed in ovarian and other cancers. CA19-9 and its relatives are ligands binding at Selectins. However, the G1 core can also be modified by Gal-3-Sulfo-T4 to give SE-3-Gal-β3-GalNAc-α-(G1-Su; 25,26), i.e., a ligand binding at certain Galectins. Thus, depending upon the biosynthetic G1 core extension in different cells, or clones of cells, different cell adhesion ligands can be expressed as components of the cell surface glycan profile.

To summarize the G1 core example (supra), G1 can be extended to yield a variety of different related, but structurally diverse, glycan signatures, that constitute a glycan expression profile on a cell, or group of cells, that, in turn, determines its ability to participate in cell adhesive interactions required for maintaining tissue pattern and structure, as well as, function. The requisite glycan pattern of a group of cells in a tissue is, in turn, determined by biosynthetic enzymes, each having unique substrate specificity and different product, and each competing with other cellular enzymes for substrates and acceptor glycan chains. Cooperatively, these enzymes play vital roles in determining the cellular glycan profile and, considering the complexity, it is not hard to see how gene mutations, epigenetic changes in gene expression, oxidants, toxins and poor cellular physiology could result in a disease condition.

As a fourth predictive principle, it is necessary to study core extension and expression profiles of biosynthetic enzymes in clinical isolates, i.e., not cell lines. For instance, using biopsy and autopsy tissues the inventors found that there is: i) a switch in the Core-1 extension profiles in gastric cancer tissue that is linked to up-regulation of sulfo-Ts and down-regulation of α-1,2-FT activity; ii) the change in enzyme expression results in increased cell surface Fuc-α2-Gal-β3-GalNAc-α-(G1-f) and SE-3Gal-β3-GalNAc-α-(G1-

Su); and iii) the change is correlated with disease burden, prognosis and/or phase/grade of the gastric cancer. Such observations are not possible using cell lines.

As a fifth predictive principle, it is necessary to understand the basis for observed changes in expressed glycan patterns in particular clones of cells. To continue the example from above, epigenetic changes in gastric cancers with large islands of methylation may account for the observed G1-f and G1-Su in certain gastric tumors.

As a sixth predictive principle, seeming small changes in cellular glycan profiles can have significant functional effects. For instance, changes in sulfation of proteoglycans can result in signal through cell adhesion lectin receptors with resultant tumor-promoting or tumor-suppressing effects. Sulfo-Ts are responsible for cellular "sulfate codes", i.e., signature sulfation patterns on glycans that promote binding of glycoproteins at specific receptors. During cancer progression mutations and epigenetic changes in enzyme expression can result in different patterns of sulfated glycans on different cellular glycosaminoglycans (GAGs) and sulfotransferases (sulfo-Ts), in particular, may be related to metastasis and angiogenesis. For instance, chondroitin sulfate (CS) and dermatan sulfate (DS), are both products of sulfo-Ts. Both are also known to interact with CD44 as well as L- and P-selectins expressed on endothelial cells and involved in adhesive interactions. Inappropriate over-sulfation of CS and DS in tumors can result in 4,6-di-O-sulfated-GalNAc which, bind strongly at the L- and P-selectins and can, in turn, play a role in tumor angiogenesis. Thus, proper biosynthesis and patterning of "sulfate glycan codes" on the cell surface and in the glycosaminoglycan (GAGP) extracellular matrix may be required for maintenance of a normal, not neoplastic, cellular phenotype; and, inappropriate sulfate glycan codes may participate in metastatic spread of tumor cells. As a result, identifying inappropriate sulfate glycan codes can be used to assess cell and tissue health, disease, and prognosis in cancer.

These examples provide significant support for the importance of each of the individual six predictive principles, as well as, the overall utility of the six predictive principles as an overarching strategy for identification and characterization of cellular glycan profiles and their functional significance in health and disease. Understanding enzyme specificities and using biochemistry to predict cellular and tissue glycan profiles, in turn, serves to identify functional features of cells in health and disease. The latter predictive diagnostic tools find a variety of uses, e.g. in cancer prognosis; predicting relapse after chemotherapy and radiation; assessing the likelihood for metastatic spread; and/or predicting the responsiveness to particular cancer stem cells to different classes of therapeutic agents, i.e., a "predictive strategy" based on the six predictive principles set forth above.

As a most fortunate consequence of application of this predictive strategy, the instant small molecule glyco-decoy acceptor compounds (Examples, below) were identified which inhibit the synthesis of cell adhesion ligands by virtue of targeted disruption of cellular glycosylation.

Tools

Synthetic acceptors: Enzymes involved in glycan synthesis make stepwise additions to a growing glycan chain. Acceptors require mimicry at two structural levels to be functional: namely, (i) mimicry of Ser, Asp, Thr and Asn peptide O- and N-glycosylation acceptor site(s); and (ii) mimicry of terminal glycan sugar acceptor residues. As detailed in EXAMPLE 3, below, artificial acceptors with O-methyl and O-fluoro adducts constitute dead-end acceptors, inhibitors and "bait" for trapping, profiling and/or inhibiting cellular enzymes.

Designer substrates: Designer substrates were also used distinguish between different possible competing glycosyltransferase activities in cells. The specificity of a family of 2,3-sialyltransferases, as well as, cloned Galβ-sulfotransferases was determined using designer substrates and this, in turn, led to the identification of the Core-2 biosynthetic products CD43, PSGL-1 and GlyCAM-1.

Example 2

Predictive Assay Methods

Prostate and Breast Cancer: The "predictive strategy" was applied first to elucidate glycan signatures in prostate and breast cancer cells. The enzyme activity profiles of prostate cancer LNCaP cells were determined by the inventors. Predictions based on these family enzyme activity profiles agreed with glycan structures of PSA produced by LNCaP cells as reported by others. Next, the enzyme activity profiles were determined for four breast cancer cell lines, ZR-75-1, MDA-MB-231, MCF-7 and T47D70. The expression profiles of chain-terminating enzymes in the latter studies predicted glycan structures which were also reported previously by others (71). Follow-on studies identified two distinct Gal:3-O-sulfotransferase activities in breast and colon cancer cell lines and tumor tissues, one specific for T-hapten Galβ3GalNAcα and another with preference for the Galβ4GlcNAc terminal in the Core-2 tetra-saccharide Galβ4GlcNAcα□(Galβ1□)GalNAcα.

Ovarian Cancer: Next, glycosyltransferases of ovarian cancer tissues were investigated using sulfated saccharides to examine the specificity of α-L-fucosyl-transferases (α-L-fucosyTs) from ovarian tumor tissues and other sources. These findings showed that 3-O-sulfated Galβ4GlcNAc and Galβ3GlcNAc act as natural substrate acceptors to give, respectively, 3-O-sulfated Le$^x$ (Lewis-x) and Le$^a$ (Lewis$^a$) structures. However, SE-3Galβ3GlcNAcβ□ was found to be a better acceptor for the enzyme in ovarian cancer yielding SE-3Galβ3(Fucα4)GlcNAcβ□(sulfo-Lewis$^a$). Based upon specificity studies of α3/4-L-fucosyltransferase from ovarian tumor tissues and cell lines, the inventors believe it highly likely that sulfated glycoproteins in these cells contain sulfated Le$^a$ structures. Interestingly, Feizi et al. previously reported the tangential finding of 3-O-sulfated Le$^x$ and Le$^a$ structures in ovarian adenocarcinoma glycoproteins. Similarly, as a first confirmation checkpoint, the inventor's findings, supra, were found consistent with previous reports by other groups who also suggested the presence of certain 3-O-sulfo-Le$^x$ modifications on glycoproteins in certain colon cancer cell lines. In addition, the presence of β3-NAc-galactosyl-transferase (β3GalNAcTs; β3GALNT2) and β4-NAc-galactosyl-transferase (β4GalNAcTs; β3GALNT3/4) had been suggested previously by others, i.e., also consistent with the inventor's observations.

To further the confirmation process, since GlcNAcβ-OB can act as a biosynthetic acceptor for both the β3- and β4-GalNAc transferases, for use as structural reference compounds, the inventors synthesized all of the possible expected anomeric products: namely, GalNAcβ3GlcNAcβ-OB, GalNAcβ4GlcNAcβ-OB and GalNAcβ6GlcNAcβ-OB. Using the MSn capability of an ion trap mass spectrometer, the three isomers of these disaccharides were distinguished. In addition, the MS2- and MS3-molecular mass ions of the B2-ion of these reference compounds were distinguishable, i.e., GalNAcβ4GlcNAc-OB and GalNAcβ6GlcNAcβ→OB. When applied to the colon cancer cell line synthetic products, the B2-ion of GalNAcβ3GlcNAcβ-OB was not observed in the MS2 spectrum suggesting just the GalNAcβ4GlcNAc-OB as a natural synthetic product in this particular colon cancer cell type.

To further the confirmation, the discriminatory power of a triple quadrapole mass spectrometer was used with the three synthetic reference substrates, to characterize the enzymatic activity of the respective different βGalNAcTs. The biosynthetic products were identified and quantified based on their characteristic retention times and product ions. Using tandem MS, the structures of these compounds were established the product ions were characterized for transitions that could be used in the MRM mode. Interestingly, the ovarian cell line SW626 showed both β3GalNAcTs and β4GalNAcTs functional activities, at almost an identical ratio, while the PA-1 ovarian cell line had primarily β4GalNAcTs functional enzyme activity. Since the β3-GalNAcTs activity has not been reported previously, the discovery of β3GalNAcT indicates the existence of GalNAcβ3GlcNAc glycan structures on glycoproteins and in glycolipids in ovarian cancer, i.e., certain of which represent cancer specific diagnostic antigens and therapeutic targets.

Additional Changes in Ovarian Cancer: Specificity of sulfo-transferase was investigated in ovarian cancer tissues, i.e., producing a sulfo-ester (SE) in the acceptor carbohydrate. The results reveal prominent expression of Galβ3-sulfo-transferase-4 (GA3ST4) producing as a product SE3Galβ3GalNAc, e.g. in mucins. Some tumor tissues also contained GAL3ST3, which produced SE3Galβ4GlcNAc. The overall results suggested a biosynthetic switch in tumor cells, i.e., from a normal tissue pattern of enzyme expression to a tumor SE3Galβ3GalNAc pattern. Studies of the tissue sulfo-transferases (sulfoTs) and fucosyl-transferases (FucTs) in normal ovarian tissues, predicted 4 main backbone glycosyl structures, namely:

(i) Core 1 (Galβ3GalNAcα) (in Structure 1K; TABLE1);
(ii) Core-1-extended-type-1 (terminal Galβ3GlcNAc-; (Galβ3GlcNAcβ3Galβ3GalNAcα), in our target antigen 2K;
(iii) Target antigen 3K contains Core-1-extended type-2 with a terminal Galβ4GlcNAc-; and
(iv) 4K is built on core 2 branched tetrasaccharide (common in mucin).

In ovarian cancer cells these four core structures, supra, were found to be modified by sulfo-transferases, sialyl-transferases and fucosyl-transferases, i.e., FUT1,2, sulfoTs, sialylTs and α3/4 fucosyl-transferase. The latter enzymes were specifically expressed only in advanced-stage ovarian cancer, i.e., providing prognostic markers of disease activity. The resultant sulfated ovarian tumor glycan profile structures 1T to 6T are listed in TABLE 1.

TABLE 1

| | |
|---|---|
| 1K | SEGalβGalNAcαOZ |
| 2K | SEGaiβ3(SE6GlcNAc)βGaipβGalNAcαOZ |
| 3K | SEGaiβ4(SE6GlcNAc)βGaipβGalNAcαOZ |
| 4K | SEGaiβ3[Gaip4(SEGlcNAcβ)3GalNAcαOZ |
| 5K | SEGaiβ3[GalNAcβ4GlcNAcβ)3GalNAc |
| 6K | GlcNAcβ3(SE6Gal)β3SE6GalGaiβXyiβOZ |

O-glycan backbones are modified by Fut1,2, sulfoTs, SialylTs and α3/4 fucosylTs during progression of cancer. We consider FUT1,2 as the blocking enzyme[130] for other enzymes that construct glycans as receptors for galectins, siglecs and selectins, cell adhesion proteins. Since ovarian cancer cells are likely to express SE6GlcNAcTs and different sulfoTs GAL-ST2, -ST3 or -ST4, one example of predicted structure is given from each core. It is apparent that our profiling of enzymes can influence the priority for synthesis for mAbs. Target antigen 5K has β3GalNAc at the outer end based on βGalNAcTs, sulfoT, GALST4. Target epitope 6K is predicted due to the multi-substrate properties of CS CHSTs. Z=Allyl.

Tumor Tissues: To extend the studies with cancer cell lines (supra) to tumor tissues, expression of the core βGalNAc-modifying enzymes was studied in tumor tissues. Using synthetic acceptors and RT-PCR analysis techniques, the presence of β3GalNAcTs and β4GalNAcTs was demonstrated in individual ovarian cancer tissues. Since similar GalNAcβ4GlcNAc structures were previously reported by others as glycosylation of prostate proteins, i.e., PSA, LNCaP, RNase-1104 and glycodelin, the enzyme profiling study was extended to include prostate, pancreatic cancer and breast cancer tissues. Positive results were recorded for these latter tumor types as well as ovarian cancer.

Functional Enzyme Activity Profiling: An extensive array of acceptor compounds was assembled for examining and confirming the functional enzyme activities of different families of glycosyltransferases, as well as, specific enzymes within those families. Synthetic reference compounds were also prepared to confirm synthetic intermediates and final products. Monoclonal antibodies to synthetic intermediates and products are additionally useful for screening tumor tissues to identify putative enzyme activities, products and diagnostic and therapeutic targets. These reagents, methods and tools were used, according to the overall predictive strategy (supra), to generate a composite picture of the glycosylation biosynthetic enzyme systems available for the synthesis of glycan profiles in malignant and normal tissues.

The initial focus was directed to assemble reagents for the following enzyme families: namely, i) the β-NAc-galactosaminyl-transferases (OGalNAcTs) and sulfo-transferases (sulfoTs); ii) the β-NAc-glucosaminyl-transferases (OGlcNAcTs) involved in O- and N-glycan synthesis; and iii) the enzymes that modify the outer chains of polysaccharides in glycolipids and glycoproteins, i.e., sulfo-Ts, fucosyl-Ts and sialyl-Ts. Results of profiling studies with these enzyme families was used to select substrates and acceptors which were, in turn, used to induce specific monoclonal antibodies.

Rationale for Targeting Sulfo-transferases and Fucosyl-Transferases: Biosynthetic profiling of enzymes, substrates and functional intermediates in tumor tissues, supra, was used to predict patterns of glycan on proteins and glycolipids in and on the cell membranes of tumor cells and compare that pattern with that expressed in normal tissue. Sulfated and fucosylated glycans and glycolipids represent highly attractive molecular targets for diagnostic and therapeutic development because the functional consequences of this altered glycosylation includes possible roles in tumor cell immune escape, adhesion, migration and metastasis.

For example, three glycosyltransferases (GTs) have recently been implicated by the inventors, and others, in tumor evasion and immune suppressive functions: namely, (i) the bisecting enzyme β1,4-NAcetyl-glucosaminyltransferase-III (GNTIII; M3GnT3) involved in production of N-glycans, (ii) the core β1,3-NAcetyl glucosaminyltransferase-6 (core 3 synthetase; β3Gn6) active in production of O-glycans and (iii) the β3-GlcNAc-Ts family member β1,3-NAcetylglucosaminyltransferase-1 (β3-Gn-T1). Reduced expression of glycosylation enzymes involved in the post-translational modification of proteins results in tumor cells with increase ability to evade immune clearance and metastasize. Alternatively, increased expression of glycosylation enzymes can also resulted in altered glycan signatures that are associated with enhancing tumorigenicity of proteins. Both categories of the latter changed glycans are markers for tumor burden, progression and prognosis of disease.

Using the instant predictive strategies it was possible to establish profiles for low abundance rare glycan that were not detectable by other physical techniques such as MS and LC-MS. In addition, unlike other physical techniques, the instant predictive methods simultaneously predicted global alterations in families of O- and N-glycans, proteoglycans, dermatans, chondroitins, glycolipids and the like. For instance, sulfotransferase CHST1 (chondroitin-4-sulfotransferase) is a multi-substrate enzyme that modifies both O- and N-glycans and has been implicated in synthesis of an ovarian 6-O-sulfate tumor marker, (SE3Galβ4GlcNAcβ3 (SE6)αGalβ4GlcNAcβ), recognized by monoclonal antibody HMOCC-1.

Tumor Tissue Screening Assays: A screening assay was developed to identify possible tumor tissues with altered sulfo-transferase and/or fucosyl-transferase activity for subsequent more detailed expression profiling. As background, O-glycans with a Galβ3 core structure constitute an important class of tumor antigen core structures, e.g. represented in CA19-9 (sialylated Lewis$^a$ antigen) which is used in the clinical management of pancreatic cancer. In place of sialyl modification, in ovarian and colon cancer tumor cells this Galβ core structure can be modified during biosynthesis by fucosylation, e.g. by α3/4-fucosyl transferase, and by sulfation, e.g. by sulfo-transferases like SulfoTs GalST2.3.4, i.e., resulting in highly antigenic ovarian and colon cancer tumor markers particularly for cancer stem cells. Since the biosynthetic fucosyl- and sulfo-transferases prefer the Galβ core structure, its detection in tissues was predictive. For example, FIG. 1A shows biosynthetic pathways to the CA19-9 antigen NeuAcα2,3Gal3 (Fucα4GlcNAc)β3-Galβ3GalNAcα, i.e., from GlcNAcβ3Galβ3GalNAcα (G1-e; FIG. 1A). Seeking a rapid screening assay for identifying the Galβ3/4 core structure in malignant tissues so that those enzyme expression could be profiled, a peanut agglutinin lectin (PNA) assay was developed for testing tumor tissue expression of a modified Galβ3/4 core.

Figure 1B:
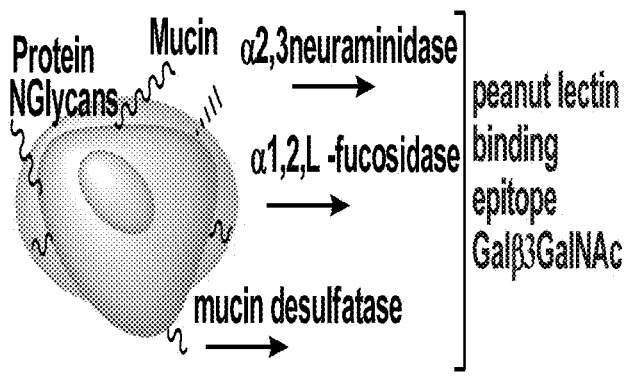
FIG. 1B is a diagram that illustrates detection of specific cell surface glycans, as described further in the EXAMPLES section, below, by: (i) treating cells first with α2,3 neuraminidase, to remove sialic acid residues; α1,2 L-fucosidase, to remove fucose residues; or mucin desulfatase, to remove sulfate-modified residues; and (ii) detecting specific binding of peanut lectin (PNA) at Galβ3GalNAc epitopes using fluorescent labeled PNA and cytofluorimetry. More specifically.

PNA Screening Assay for Galβ Core Structures in Tumor Tissues: The peanut agglutinin lectin PNA has specificity for Galβ3/4. PNA-assays have been reported in the past for evaluation of mucin chains capped with NeuAc2, (G1s in FIG. 1A) e.g. in von Willebrand Factor (VWF) protein which contains both O-glycans and N-glycans with Galβ mucin structures. In these assays the VWF was bound by antibodies coated in microtiter plates. Following binding of the VWF-mucin, the Galβ3/4 core structure was revealed by removing the cap NeuAc residues with neuraminidase. In a derivation of this assay format, PNA was used to detect Galβ3/4 core residues in breast and colon cancer tumor tissues that were un-capped using neuraminidase and α1,2-L fucosidase. Using this assay, ovarian tumor tissues were identified that contained Galβ3GalNAcα, i.e., derived from Fucα2-Galβ3GalNAcα (G1f, FIG. 1A). Similarly, sulfo-modified Galβ3/4 core structures were uncapped using bacterial sulfatases, e.g. remove sulfate ester (SE) from SE-Galβ3GalNAcα (G1sulfated, FIG. 1A) to expose Galβ3GalNAcα for PNA lectin binding. Treating sequentially with sialidase, fucosidase and sulfatase enzymes exposed Galβ3/4 core structures as depicted in FIG. 1B. This analytic strategy allowed relatively rapid screening of tumor tissue samples to determine those with altered patterns of NeuAcα2,3Gal13GalNAcα, SE-Galβ3GalNAcα and Fucα2Galβ3GalNAcα. The assay was useful to identify those samples that warranted additional enzyme profiling and/or probing with epitope specific monoclonal antibodies.

Example 3

Proof of Predictive Methods Concept: Prediction of L-Selectin Ligand Structure

Approach: Priority was given to three critical enzymes: α-L-fucosyltranferase, sialylTs, and sulfoTs, i.e., all three enzymes are involved in glycosylation of natural selectin ligands.

Overview: The findings, above, showed that Galβ4 (SE-6GlcNAc) can act as an acceptor in tumor tissues for α2,3-sialyl-Ts to yield NeuAcα2,3Galβ4(SE-6GlcNAc), EXAMPLE 2, (above). Further, the latter product was found to act as an acceptor for sulfo-transferase yielding a2,3-O-sialyl-6-O-sulfo-Le$^x$ (sulfate at the GlcNAc C-6 position of Le$^x$), i.e., a predicted tumor specific antigen. Also observed, was formation of 3-O-sialyl-6-O-sulfo-Le$^a$, i.e., from NeuAcα2,3Galβ3(SE6-GlcNAc) which is another predicted tumor specific antigen. Similarly, biosynthesis of the carbohydrate moiety of L-selectin ligand GlyCAM is as follows, namely: i.e., Galβ4(SE-6GlcNAc)D6(Galβ3)GalNAcα1-O-Benzyl (B) acts as an acceptor for α(2,3)sialyltransferase and also for α(1,3/4)fucosyltransferase to form the GlyCAM L-selectin proteoglycan ligand expressed on high endothelial venules in lymph nodes. Based on the later enzyme-based findings, it was predicted that a Core-2 branched tetrasaccharide sulfated at C-6 of GlcNAc should be part of the ligand for L-selectins, this was subsequently confirmed by others.

Synthesis of Artificial L-selectin Ligands: The preceding results encouraged synthesis of a series of Core-2 structures as possible better cell adhesion inhibitors than sLe$^x$ ligands, i.e., ligands based on the structure K3 (TABLE 1). Binding studies of L-selectins with the latter synthetic compounds confirmed their receptor binding activity.

Interested in extending these observations, a variety of different test ligands were synthesized including natural glycans expressed a glycosylation on PSGL-1 and Gly-CAM-1. The quest led to neutral molecule K2 (no charged residues), that inhibited L-selectin binding with high efficiency, i.e., at ~1/7th to 1/60th the effective concentration of sLe$^x$-OMe.

During these studies the disaccharide, GalNAc-β3-GalNAc-α-OMe [K3, shown inside the dotted line, TABLE 2, below] was synthesized and tested and, unexpectedly, showed to specifically blocked P- but not L-selectin binding. (The latter finding challenged current thinking that a negative charge in the form of a sialic acid or a sulfate are requisite for selectin binding.)

TABLE 2

Selected Examples of Ligands for Selectins.

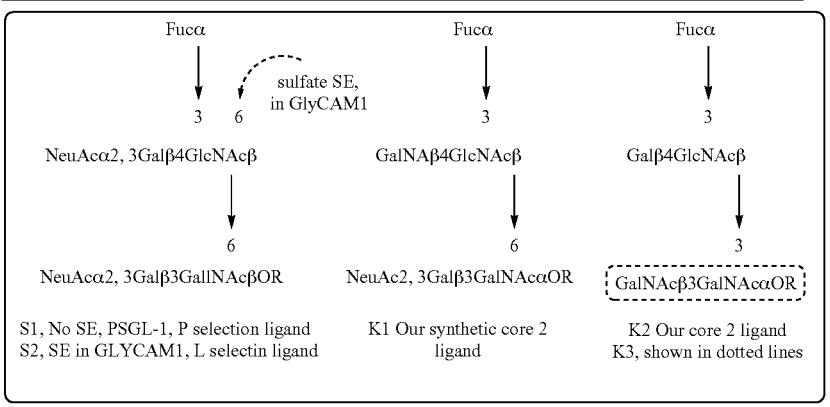

S1, No SE, PSGL-1, P selection ligand
S2, SE in GLYCAM1, L selectin ligand
K1 Our synthetic core 2 ligand
K2 Our core 2 ligand
K3, shown in dotted lines

Example 4

Synthesis of Decoy Acceptors for Key Biosynthetic Enzymes

Figure 3:
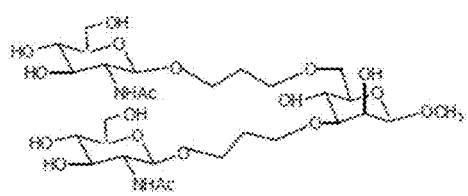
FIG. 3 is a diagram that sets forth the chemical structure of a biantennary spacer-modified trisaccharide glycoside that, according to aspects of the invention set forth in the accompanying disclosure and EXAMPLES section below, mimics the substrate acceptor functional activity of the natural biantennary core glycan heptasaccharide linked to asparagine (Asn) of glycoproteins, for example in ovarian cancer cells.

Background: Although there had been impetus for synthesis of inhibitors of glycosyltransferases related to native ligands for selectins, the synthesized acceptor-analogs, donor analogs and transition state mimetics, bi-substrates and ti-substrates had limited success. As an alternative, the instant methods use glycoside-based decoys ("glyco-decoys") of glycosyltransferases showed promise (FIG. 3). Glyco-decoys resemble biosynthetic intermediates and act as substrates to side-track the normal oligosaccharide assembly on proteins and lipids. Competing with the natural substrates, decoys divert the synthesis of glycan chains from endogenous proteins and lipids to soluble forms.

Overview: Proof of Principle Studies: A proof of principle for this glyco-decoy approach was demonstrated by (i) synthesizing test compounds K4a (FIG. 1A; GlcNAcβ3Gal☐NAP) (acetylated to facilitate membrane perfusion) and K4b (FIG. 1A) Galβ4GlcNAc☐NAP-acetylated and (ii) testing their effects on the biosynthesis of a clustered sialyl-Lewis' (sLe$^x$) glycan profile, i.e., as expressed on tumor cell mucins. sLe$^x$ clustered glycan profiles facilitate metastasis through binding interactions with selectin adhesion receptors on endothelial cells. These studies resulted in the fortuitous discovery, (detailed below), of a small molecule disaccharide glyco-decoy acceptor compound, referred to below as 5KP, which has extraordinary unexpected cell penetrability and inhibitory activity for enzymes involved in the synthesis of sLe$^x$ ligands.

Strategy: The strategy for synthesis of glyco-decoys for glycosyltransferases was driven by the following considerations: namely, i) the intended use in the identification of key enzymes responsible for generating glycan ligands for selectins. e.g., α-L-fucosyl-Ts, Sialyl-Ts, sulfo-Ts and GlcNAc-Ts; and, ii) the requirement that for an effective competitor, the acceptor/decoy needs to have better functionality than the natural acceptor(s).

Using empirical methods, it was found that modified analogs of acceptors with fluoro- or methyl-groups are better and more specific decoys for enzymes than their natural substrates. Synthetic approaches, in the EXAMPLES, below, provide improved modified, specific acceptors for determining the functional activities of the α-L-fucosyl-Ts, Sialyl-Ts, sulfo-Ts and GlcNAc-Ts enzymes. The inventors found that specific acceptors, when acetylated, functioned as cell-penetrating decoys. Test systems are provided for assessing the functionality of donor/acceptors and for determining that they are better than natural substrates involved in biosynthesis of natural ligands, i.e., using cloned enzymes ST3-Gal-I, ST3-Gal-2 and ST3-Gal-453. Detailed studies of the acceptor specificity of the latter cloned Gal-3-O-sulfo-Ts (Gal3STs) ST-2, ST-3 and ST-456, in a combined study of sialyl-Ts and sulfo-Ts enzyme activities, provided, for the first time, elucidation of the biosynthetic pathways for the Core-2 glycan selectin ligands CD43, PSGL-1, GlyCAM-1 and Core-2 sulfated glycans.

Perillyl Small Molecule Inhibitors: 5KP (GlcNAcβ-OP), a Perillyl (P) analog of GlcNAc, was synthesized for use as a decoy acceptor to reduce biosynthesis of E-selectin ligands, thereby inhibiting the interactions of E-selectin receptors with their carbohydrate ligands, i.e., with the rationale deriving from enzyme profiling studies as follows: namely, Enzyme Profiling: Since some N-linked E-selectin glycoprotein ligands, such as CD44, are endowed with sialyl-Le$^x$ on the outer glycosyl chains, the inventors investigated the order of glycosylation and location of sialyl-Le$^x$ in the branched N-glycans of CD44. Recognizing that sialyl-Le$^x$ is often located in tri- and tetra-saccharide chains in glycans, and that branching enzyme N-acetylglucosamyltransferase V (GnTV) should be a key enzyme involved in generation of these complex glycan structures.

TABLE 3

Synthetic Test Compounds: 5KP Decoy Compounds Disrupting Selectin Ligand Synthesis, i.e., M3G3GnT5 From M3G2Gn5 Which is, in turn, Assembled From M3G0Gn4.

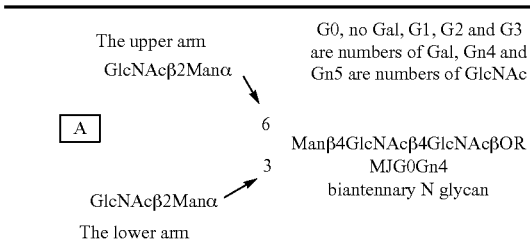

TABLE 3-continued

Synthetic Test Compounds: 5KP Decoy Compounds Disrupting
Selectin Ligand Synthesis, i.e., M3G3GnT5 From M3G2Gn5
Which is, in turn, Assembled From M3G0Gn4.

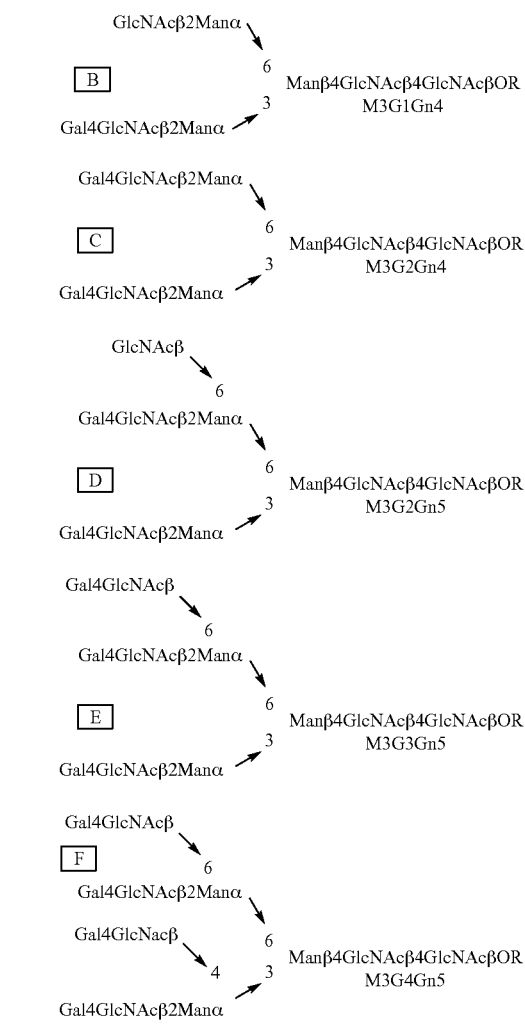

Investigating the order of carbohydrate addition with the aid of compounds shown in Table 3, it can be discovered that β1,4-galatosyltransferase (B4GALT) acts on the M3G0Gn4 substrate to add a Gal residue. The selectin lower arm terminal GlcNAc residue, i.e., GlcNAc-β2-Man-α3-Man-β-, was the preferred acceptor site for B4GALT galactose addition, i.e., followed by galactosyl-addition at the upper arm in M3G0Gn4, but stereochemically, apparently only in the absence of a bisecting GlcNAc; a residue linked C-4 at Manβ in M3 (not shown).

Figure 2:
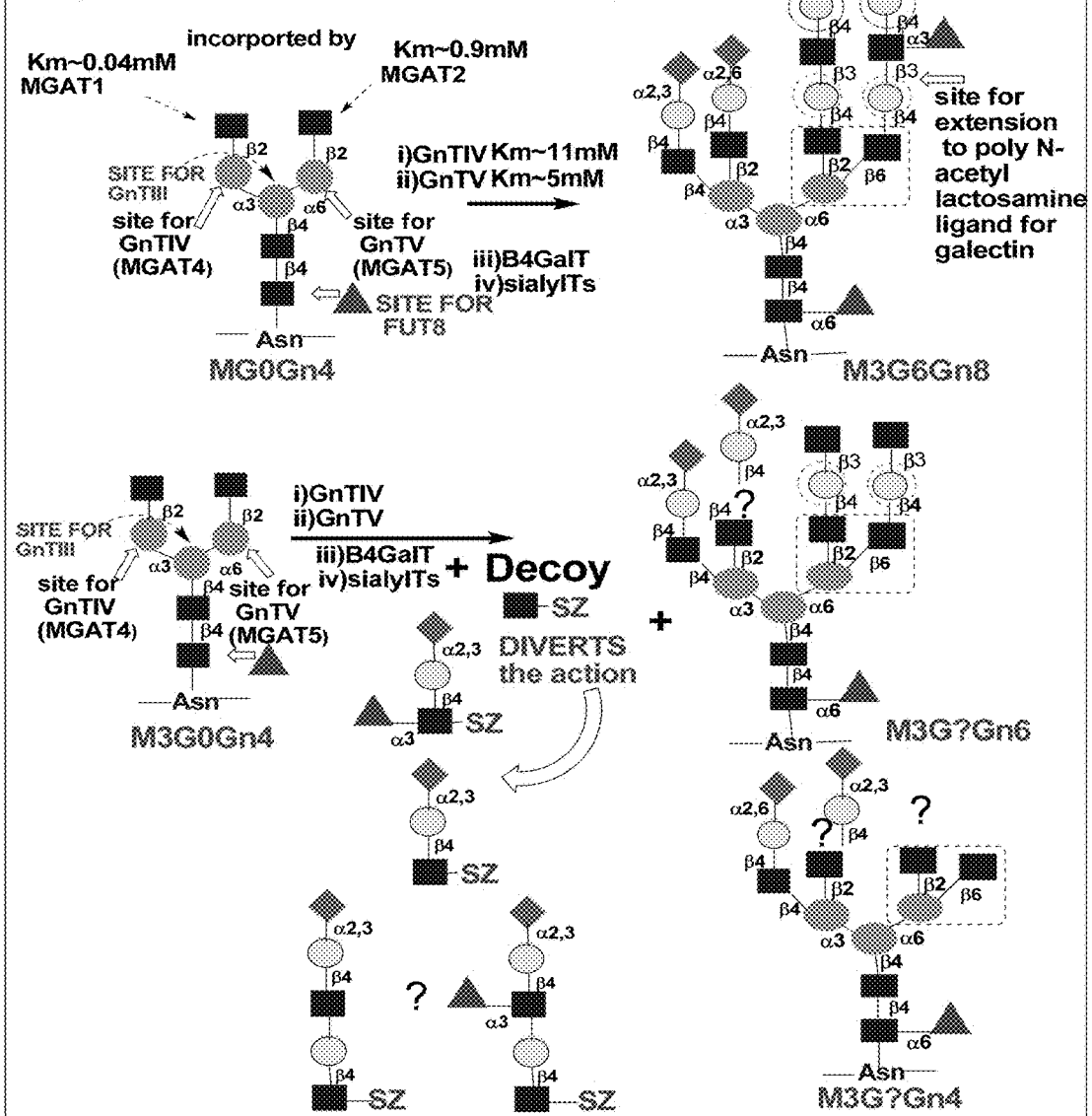
FIG. 2 is a diagram that illustrates a biosynthetic pathway for synthesis of an N-glycan, i.e., as illustrated in the EXAMPLES section further below. The 5KP, GlcNAc-P, acceptor substrate according to the invention is its acetylated analog a decoy for the B4GALT enzyme (in the red rectangle) which disrupts the biosynthesis of M3G3Gn5 and M3G3Gn, i.e., both of which have sialyl-Lewis-X (sLe$^x$)

A synthetic spacer-modified disaccharide GlcNAc-Man-like glycoside, methyl-3,6-di-0-(2-acetamido-2-deoxyglucopyranosyloxyethyl)-α-o-mannopyranoside with an apparent Km=0.18, was found to be functionally equivalent to the natural Asn-linked oligosaccharide acceptor M3G0Gn4 (Km=0.13), i.e., simple GlcNAc was an 80-fold worse acceptor (Km=8.3 mM). Since, very little was known about the structural requirements for galactosyl-addition followed by GnTV, i.e., at the GlcNAc residue of M3G2Gn5 (shown in the red circle, FIG. 2), these findings were significant for elucidating the mechanisms of synthesis of selectin ligand(s). Importantly, since synthetic, short di- and tri-saccharide substrates GlcNAc-β2-Man-α-Man-β-OR; GlcNAc-β2-Man-Glc-β-OR are acceptors for GnV embodiments of the invention provide small molecules capable of acting as competitive inhibitors of biosynthetic enzymes to decoy β4Gal, (shown in the red circle), resulting in disruption of E-selectin ligand synthesis, i.e., inhibition by GlcNAc having just one other residue (e.g. K5P). Derivative therefrom, the instant methods identify GlcNAc-β2-Man-α-Man-β-OR and GlcNAc-β2-Man-Glc-β-OR as decoy competitive inhibitors, with the proviso that both compounds achieve increased biosynthesis inhibitory activity when acetylated. Importantly, the findings also showed that small, cell-penetrable saccharide molecules could mimic the native Asn structure within the M3G2Gn4 native acceptor that is endogenously required for chain extension of tri- and tetra-antennary N-glycans (FIG. 2). Based on these findings, additional inhibitors were synthesized with the aim of increasing cell-penetrability and inhibition of enzyme activities in cells. The results of these studies identified K5P, above, as an unexpected highly significant cell-permeable small molecule inhibitor of E-selectin ligand synthesis and expression on tumor cell surfaces. (Bioactivity of 5KP in test systems is disclosed in EXAMPLE 8, below.)

Glyco-Decoy Inhibitor Design. Based on the enzyme profiling studies, above, the inventors predicted that simple GlcNAc-β-linked compounds would act as glyco-decoy competitive inhibitors for galactose addition at M3G2Gn5 (FIG. 2) in E-selectin ligands. The latter small molecules were predicted to inhibit the M3G2Gn5 core extension to yield M3G3Gn5, with further extension to give M3G3Gn5F1Sia1 displaying sLe$^x$, i.e., the functional glycan structures in E-selectin ligands. Data, below, confirms that the instant 5KP (GlcNAcβ-OP), a Perillyl (P) analog, small molecule inhibits the synthesis of ligands binding at E-selectin, and, in an E-select specific manner that does not affect binding at P- or L-selectins. Reduced toxicity and side effects are also achieved by virtue of the specificity of the 5KP decoy, which does not inhibit the key β4GalT enzyme involved in assembly of core-2 cellular glycans, (G2-tet structures; FIG. 1), that are backbone structures for homeostatic L- and P-selectin ligands. Thus, embodiments of the invention provide decoy inhibitors that inhibit the M3G2Gn5 core extension to yield M3G3Gn5, with further extension to give M3G3Gn5F1Sia1; without inhibiting the β4GalT enzyme involved in assembly of core-2 cellular glycans.

FIG. 2 illustrates a biosynthetic pathway for synthesis of an N-glycan. The 5KP, GlcNAc-P, acceptor substrate according to the invention is a decoy for the B4GALT enzyme (in the red rectangle) which disrupts the biosynthesis of M3G3Gn5, M3G3Gn5F1Sia, which produce sialyl-Lewis-X (sLe$^x$) determinants that are ligands on inflammatory immune cells and metastatic tumor cells for E-selectin receptors on vascular endothelial cells. FIG. 2 also illustrate that KP5 and the instant analogs and derivatives thereof act as decoy biosynthetic inhibitors to disrupt the assembly of glycan chains for ligands binding at galectins. The instant compounds are decoys that side-track the assembly of bi-antennary N-glycans to inhibit synthesis of higher tri- and tetra-antennary glycans.

FIG. 2 also Illustrates disruption of biosynthesis of a polylactosamine glycan chain by a decoy by diverting and disrupting the extension of biantennary N-glycans to tri- and tetra-antennary glycans. Polylactosamine glycans bind to galectins and such complex N-glycans constitute hallmarks of many cancer cells especially metastatic cells.

These findings confirm the instant predictive methods, and their utility in designing the instant small molecule compounds for synthesis as glyco-decoy. Since E-selectin ligands are involved in inflammatory and autoimmune diseases, the instant approaches provide novel methods for identifying candidate pharmaceutical compounds, as well as, new treatments for afflicted patients.

Summary: In addition to 5KOP (GlcNAcβ-OP), a Perillyl (P) analog above, glyco-decoys 5KNAP (GlcNAcβNAP), 5KP (GlcNAcβP), 5KRE (GlcNAcβRE), and GlcNAc-β-Benzyl are, according to the instant methods, also identified as active inhibitors of E-selectin ligand synthesis. The present studies, below (EXAMPLES 6-8), confirm 5KP as a small molecule cell-penetrable specific inhibitor of galactose incorporation into E-selectin ligands thereby disrupting their synthesis, i.e., shown in FIG. 2; enclosed by the dotted circle in the upper arm of M3G2Gn4. Showing selective specificity, designed-in by knowing their molecular target enzyme and its substrate specificity, 5KP does not inhibit biosynthesis of PSGL-1 and L-selectin ligands built on Core-2 Glycans (S1 and S2 in FIG. 2). With 5KP treatment, there was no change in expression of 2,6-sialyl glycans as evaluated using SNA-lectin which is specific for these sialyl sequences. 5KP does not act as a decoy for the biosynthetic pathway of M32SG2Gn4 having 2,6-sialyl residues. (Bioactivity of 5KP in test systems is disclosed in EXAMPLE 8, below.)

The discovery of the 5KP glyco-pharmacophore in the preceding studies validated the instant predictive strategy. Overall the predictive strategy was highly useful for interfacing glycol-chemistry and glycobiology to predict and synthesize novel generations of candidate pharmaceutical and diagnostic compounds, i.e., not predicted by other approaches. The instant methods are thus predictive for glyco-decoy biosynthetic inhibitors of many different types and classes of cell adhesion ligands, including e.g. siglecs, selectins, galectins, C- and S-lectins and other cellular pattern recognition receptors (PRR). The present discoveries are based in the fundamental instant six predictive principles, the resultant predictive strategy and detailed studies directed to application of the predictive principles to elucidate the substrate specificities of biosynthetic enzymes that coordinately, and stepwise, establish the global glycan patterns of carbohydrate ligands located on glycoprotein as O- and N-glycans on tumor cell surfaces. Data shows drastically lowered expression of E-selectin ligand in HL60 cells treated with a decoy and a 90% reduction in neutrophil invasion in an ex-vivo (neutrophils treated outside the mouse and then reintroduced) thioglycollate-induced inflammatory peritoneal mouse model.

Example 5

Small Molecule Synthetic Inhibitors: Carbohydrate Glyco-Analogs and Decoy Acceptors With the aim of developing a transferase-specific acceptor, small molecule synthetic molecules and modified analogs used as acceptors for glycosyltransferases. Using these compounds with enzyme and expression profiling (EXAMPLE 1, above) the studies identified several novel β-GlcNAc-transferases involved in assembly of unique O-glycans with varying different core structures The different product structures were confirmed using reference compounds, i.e., synthesized as described in EXAMPLE 1 (above). The results with reference standards also showed definitively that sLe$^x$ glycans act as ligands for selectins but NeuAc-α2,6-Gal-β4-(Fucα3)-GlcNAc-β- did not. NeuAc-α2,6-Gal-β4-GlcNAc also did not act as an acceptor for α3/4-fucosyltransferase. Thus, viewing the biochemistry, the inventors concluded that for synthesis of novel selectin ligands a sialylated- or corresponding sulfated-core structure was required to act as an acceptor for the α1,3/4-L-fucosyltransferase enzyme (Table 4). Based on this prediction, the fucosyl selectin ligand products were predicted.

TABLE 4

R Glyco-Acceptor + 1,3/4Fuc-T → R [(Fuc 3/4)-Glyco-Acceptor] ligand for selectins, R = SE or NeuAc In preparation for synthesis of specific inhibitors, the specificity of the α3/4-L-fucosyltransferase was profiled using a series of sulfated synthetic saccharide acceptors. Interpreting the results, the inventors synthesized 3-sulfo-Lewis$^x$ for characterization of the enzymatic product, i.e., when using 3-sulfo-N-acetyl-lactosamine as an acceptor. 3-sulfo-Lewis$^x$ was subsequently subject by the inventor in an issued US patent (U.S. Pat. No. 5,9732,907). Building on this understanding, the natural ligand for GLYCAM was predicted and synthesized, i.e., core-2 (Gal-β4-(SE-6-GlcNAc)-β6-(Galβ3)-GalNAc-α-).

Example 6

Modified Small Molecule Cell Penetrable Glyco Decoy Analog Compounds

Summary observations, EXAMPLE 5 above, show that low molecular weight carbohydrate inhibitors can act as decoy substrate acceptors to disrupt biosynthetic pathways for native glycan ligands for E-, L- and P selectin receptors.

Acetyl-Modification: To profile anti-tumor activity, acetylated 4-fluoro-GlcNAc (F-4-GlcNAc) was synthesized as a cell-penetrable inhibitor of selectin-mediated ovarian and colon carcinoma tumor cell adhesion.

Since tumor cell mucins with clusters of sialyl-Le$^x$ have been implicated in metastasis mediated through selectin receptors, cell-penetrating acetylated derivatives of GlcNAc-β3-Gal-β-O-NAP and Gal-β4-GlcNAc-β1-O-NAP were also synthesized as decoys. The instant acetylated disaccharide precursors were cell permeable, and upon de-esterification in a cell, inhibited biosynthesis of selectin ligands, thereby inhibiting selectin-mediated cell adhesion.

Bioactivity of acetylated analogs: The effects of acetylated GlcNAc-β3-Gal-β-NAP and trisaccharide GlcNAc-β3-(GlcNAc-β6-Gal)β-NAP were examined on the expression of sialyl-Lewis$^x$ biosynthesis in U937 human lymphoma cells, with the finding that acetylated trisaccharides are membrane permeable and that the intracellular, esterase-released, trisaccharide acts as a glyco-decoy for transferase enzymes. These findings showed that modified analogs of saccharides with acetyl-groups were better acceptors for transferase enzymes in gastric cell lines than those modified with fluoro- or methyl-groups, e.g., MeO-3-Gal-β4-GlcNAc-β4-(Galβ3)-GalNAc-α-OMe, i.e., the latter fluoro- and methyl-compounds have been reported by others to both reduce binding of tumor cells to mouse momentum and reduce tumor growth rates. In addition, the inventors recent studies showed that fluorinated GalNAc metabolically alters glycan structures on leukocyte PSGL-1, i.e., reducing cell binding to selectins and also inhibiting biosynthesis of chondroitin sulfate.

5KP globo-analogs: Synthesis of analogs of 5KP (GlcNAc-β-P), and related glyco-pharmacophore compounds expressed in HL60 and LS174T colon carcinoma cells, were synthesized including the globo-backbone decoy 6K (Gal-β3-GalNAc-β3-Gal-OR), which was designed to inhibit synthesis of ligands binding at both L- and P-selectins. The underlying hypothesis was that the globo-backbone would act as an efficient acceptor for both ST3Gal,1,2 and ST3Gal4 and the construct Core-2 ligands, e.g. S1 and S2, shown in TABLE 1, above. Thus, acetylated 6K analogs were predicted to be selectin ligand decoys which would inhibit biosynthesis of L- and P-selectin ligands.

Decoys having NAP residues: Carbohydrate decoys are most commonly synthesized with anomeric aryl, benzyl residues. As a novel potentially toxic acceptor alternative, specific decoy acceptors of target enzymes were synthesized with 2-methyl-naphthalenes (NAP) as the aglycone instead of benzyl, e.g. 6K where R=NAP, i.e., 2-naphthyl-methyl.

Decoy acceptors having natural product residues: Since natural product (NP) nutraceutical carbohydrate compounds have been reported to exhibit anti-tumor activity, decoys having a novel bioactive natural product residues were also constructed. Recognizing that numerous natural products have been reported to prevent and/or treatment cancer and that in many cases the mechanism of their action is either poorly understood, or not understood at all. However, recognizing that taxol was one such natural product and believing that certain other of these compounds, or their metabolites, might constitute natural inhibitors of glycan biosynthesis, to explore this possibility resveratrol (RE) and perillyl alcohol (POH) were chosen for inclusion in glycol-decoy synthesis.

The rationale for resveratrol (RE) was as follows: namely, as a natural polyphenol from grapes and other plants this compound, or its metabolic product(s), reduces cytokine expression in the tumor microenvironment. Recent findings suggested to the inventors that over-expression of cytokines in the tumor microenvironment might, in-turn, trigger over-expression of glycosyl-Ts. Believing it highly likely that an unmodified RE residue would retain its original/inherent function, a search was initiated to identify promising poly-phenolic RE residues suitable for use in construction of decoy acceptors. A few naturally occurring glycosylated derivatives of trans-resveratrol have been reported. Resveratrol-3-O-β-D-glucopyranoside is most abundant naturally, i.e., relative to the 4-O substituted analog. Glycosylation of resveratrol apparently serves to protect it from oxidation and 3-Oβ-Dglucopyranoside-resveratrol apparently retains certain of its biological functions. Thus, the strategy was to introduce glycosylation at C-3 position of resveratrol so that the poly-phenolic product could be tested as acceptor/inhibitor of selectin ligand biosynthesis. The synthesis scheme considered the need to protect the 4'-hydroxy as a potentially important functional group for resveratrol anti-oxidant activity.

The rationale for perillyl alcohol (POH) was as follows, namely: perillyl alcohol is a hydroxylated Limonene terpene analog somewhat structurally similar to 5KP (GlcNAcβOP) and 7KP* (GalNAcαOP), above. Limonene reportedly has anti-inflammatory properties and proposed anticancer activity. The inventor's recognition that POH very likely inhibits transferases involved in synthesis of selectin ligands, provides basis for the construction of the instant POH-acceptor compounds and their instant uses to inhibit inflammation and tumor metastasis, as well as, novel cytokine bioassays for assessing the activity of glyco-decoys (EXAMPLE 7, below).

Example 7

Cytokine Bioassays for Small Molecule Cell Penetrable Glyco-Decoy Compounds

Assessing the biological activity of novel glyco-acceptor decoys on enzyme activities in tumor and immune cell cultures and in tumor- and inflammation-animal model studies, is disclosed in the Examples above. Here, recognizing that natural products (NP; Example 6) likely inhibit biosynthesis of selectin ligands, and that cytokines in the tumor microenvironment likely up-regulate synthesis of those selectin ligands, the inventors recognized a new pathway to rapidly assay synthetic acceptor compounds for bioactivity, i.e., by cytokine bioassays.

Rationale: In the few cases where anti-tumor or anti-inflammatory activity has been noted, the mechanism of action is not understood, perhaps due to the complexity of the interactions. For example, studies reveal that resveratrol can modify signaling through multiple cellular pathways including NFκB, Akt, MAPK, Wnt, Notch, p53, AR, ER and others. Since resveratrol appears to decrease cytokine expression (for example TNFα) and/or cytokine-induced biological functions, expression of selected cytokines in the experiments with NP-glyco-decoys can be monitored in vitro. It is believed highly likely that over-expression of cytokines in the tumor microenvironment enhances expression of glycosyl-Ts including Sulfo-Ts. Therefore, appropriate controls in in vitro cytokine experiments with NP-glyco-decoys include e.g. resveratrol, perillyl alcohol (POH, as well as, its analog limonene which has no —OH residue) and NAP. As disclosed in Example 6, above, NP glyco-decoys include RE- and POH-glyco-decoys.

Cytokine Assays: Levels of selected cytokine proteins such as TGFβ, bFGF, HGF, TNFα, IL4, IL6, IL7, IL8 and IL10 are determined using specific ELISA tests, e.g. according to the manufacturer's protocol; or alternatively, by more sensitive ELISpot or cytoflorimetric analysis of cytokine producing cells. Alternatively, cytokine expression is assayed by RT-PCR. Recognizing the production of TGFβ by many types of carcinomas; its negative-regulatory effects of TGFβ on gene expression in antigen presenting cells (APC); its up-regulatory effects on collagen and heparin sulfate proteoglycan synthesis by mesenchymal cells (unpublished observations); and its growth promoting effects on tissue-derived stem cells (unpublished observations), it is believed highly likely that TGFβ is responsible for up-regulated selectin ligand synthesis in metastatic clones of cancer stem cells.

Mono- and di-saccharides reduce cytokine expression: In the West Punjab of Pakistan, mother's milk is used for treatment of ear pain in infants as a folk medicine. Since human and goat milk reportedly can have anti-inflammatory properties, the inventors tested whether small saccharides in milk could reduce cytokine expression in CaCo-2 tumor cells. Caco2 cells treated with synthetic disaccharide Fuc-α2-Gal, (a disaccharide), and fucosyl-lactoside, both found in human milk, reduced expression of TNFα by ~40% and IL10 by 75%. As a stereo-specificity control, Fuc-α-O-methyl-Gal reduced levels of IL10, by 75% and IL8, by 45%, but had no effect on TNFα.

Example 8

Bioactivity of Small Molecule Cell-Penetrable Glyco-Decoy Compounds

Model System Rationale: CD44 contains an E-selectin ligand; it is a multifunctional class-I trans-membrane glycoprotein; and it is also a specific acceptor for hyaluronic acid, thereby potentially promoting migration of both normal cells and certain cancer cells. CD44 is also a recognized surface marker in certain cancer stem cells, i.e., as reviewed and incorporated herein by reference in its entirety. In addition, CD44 may act as a cell membrane co-receptor in promoting and/or coordinating presentation of certain cytokines and chemokines at their receptors. Synthesis of the instant transferase acceptor decoy compounds that suppress cytokine co-receptor activity, especially at CD44, comprises a novel alternative approach for drug development.

Test methods: HL60 tumor cells express CD44. CD44 is also expressed by LS174T colon carcinoma cells. F4 GalNAc-acetate, above, was synthesized as a metabolic inhibitor of selectin ligand biosynthesis. For testing, doses of GalNAc-acetate in the range of 0-100 µM were added to HL60 or LS174T cells in culture, i.e., plated at a density of $0.2 \times 10^6$ cells/mL in IMDM medium containing 20% FCS, Penicillin and Streptomycin; and while in the cells were experiencing exponential log phase growth. Experiments were performed in triplicate.

The effect of 5KP on E-selectin Ig binding. Neuraminidase was obtained from Sigma (*Clostridium perfringens* (*C. welchii*). To remove any potential E-selectin receptor blocking sialic acid residues, 100 µl of 0.05 U/ml neuraminidase was added to $1 \times 10^6$ HL60 cells in 900 µl of PBS and the mixture was incubated at 37° C. for 30 mins. Neuraminidase-treated HL60 cells were washed twice with PBS and returned to culture medium. 5KP (GlcNAcβ-O—P; EXAMPLE 4) was dissolved in DMSO at a concentration of 50 mM and an aliquot was diluted in medium IMDM and added to the neuraminidase treated cells at a final concentration of 200 µM. DMSO was added to parallel neuraminidase-treated HL60 cell cultures as a vehicle control. HL60 cells treated with 5KP to inhibit, E-selectin ligand synthesis, were incubated for 24 hrs. in IMDM medium and then analyzed for fluorescent selectin binding by flow cytometry, i.e., E-selectin, P-selectin and, as a positive control, lectin SNA.

Figure 4:
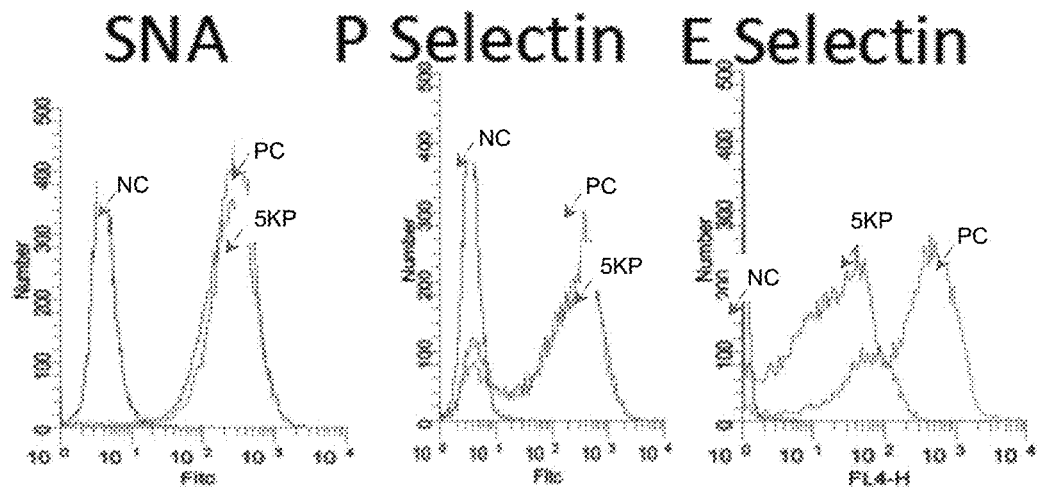
FIG. 4 are graphs that illustrate inhibition of cellular binding at E- and P-selectin receptors affected by the instant acetylated 5-KP dead-end decoy. Briefly, HL60 cells were treated with neuraminidase at day 0 to remove any endogenous ligands bound at cellular E- and P-selectin receptors; then, after washing the cells, acetylated 5KP, GlcNAc-P (5KP) decoy was added; 24 hrs later selectin receptor binding was measured by adding specific test ligands. Binding of test ligands at P- and E-selectins was determined using specific antibodies and SNA lectin. SNA and P-Selectin binding activity were reduced to background levels by addition of the instant 5KP dead-end substrate decoy. E-Selectin binding was reduced by 2-logs in the presence of 5KP. Red line 5KP at 200 M; Green line positive control without addition of 5KP; Black line, negative control.

Data presented in FIG. 4 plots fluorescent intensity (x-axis) against the number of cells having that intensity (y-axis). Incubating HL60 cells with 5KP effectively reduced the ligand available for E-selectin binding on the cells, as evidenced by the shift in the fluorescence intensity in the right hand panel of FIG. 4 labeled "E-selectin". 5KP specifically inhibited HL60 cell synthesis of E-selectin ligands, but not P-selectin ligands (middle panel, "P selectin", FIG. 4) and did not affect overall cellular biosynthesis or expression of glycans, i.e., as evidenced by binding of SNA lectin (left panel, "SNA", FIG. 4). After 24 hrs. of treatment with 5KP, HL60 cells were >90% viable (assessed by Trypan blue) and cell proliferation was comparable in control and 5KP-treated cultures.

To examine additional possible changes in 5KP-treated cells, flow cytometry was used to detect antibody or lectin binding at leukocyte cell surface determinants including the following ligands and binding pairs, namely: $Le^X$/CD15/$sLe^X$/CD15s/CSLEX-1; CLA/HECA-452, PSGL-1/CD162; Gal1,4GlcNAc-/LacNAc/DS [Daturastramonium] lectin; and 1,3/4/6-linked fucose/AAL [*Aleuria aurantia*] lectin.

Example 9

Discussion

Small molecules that inhibit biosynthesis of N-glycans in selectin ligands such as CD44 offer a novel approach to both drug discovery and development, i.e., glyco-drugs and glyco-conjugates for uses in therapy. The inventors have developed novel predictive methods for identification of glyco-decoys that inhibit specific types of carbohydrate chain extension in tumor cells and thereby inhibit tumor cellular functions such as anchorage dependent growth, migration and metastasis. The glyco-decoys in-turn provide valuable information about biosynthesis pathways that can be used to construct yet other small molecule inhibitors. Advantageously, glyco-decoys are synthesized using simple chemistry.

The instant 5K-OR and 5KP glycol-decoys identified above constitute extremely useful candidate drugs with novel modes of action, i.e., inhibiting specific steps in selectin-ligand synthesis to thereby inhibit critical cellular interactions involved in inflammation and cardiovascular diseases and cancer metastasis. The present illustrative disclosure (e.g. FIG. 2, FIG. 3, FIG. 4) also provides 5KP uses for reducing immune cytokine levels, i.e., alternative approaches for treatment.

The present results validate methods for profiling glyco-synthetic enzymes and predicting inhibitory compounds based on understanding of enzyme specificities combined with knowledge of the cooperative linked enzyme systems utilized by cells in constructing native ligands for cell adhesion proteins. Glyco-decoys such as Gal-β3-GalNAc-β3-Galα- are designed to be acceptors for both 2,3-sialyl-transferases ST3Gal1,2 and ST3Gal4 which are used by cells to assemble ligands for both L- and P-selectins such as GLYCAM1 and PSGL1, respectively. Compound 6K (Gal-β3-GalNAc-β3-Galα-OR) and its acetylated form are, according to the instant methods, identified as decoy inhibitors that reduce the cellular levels of GLYCAM1 and PSGL1 ligands. Glyco-decoys are also disclosed for inhibiting synthesis of ligands for all three different members of the selectin family, i.e., E-, L- and P-Selectins. For example, above find disclosed the synthesis of a disaccharide compound 3K that inhibits P-selectin. Glyco-decoys are newly discovered to be suppressors of cytokines and may be used in combination to produce synergistic inhibitory results.

Example 10

Analogs of 5KP

Design of specific 5KP analog acceptors and inhibitors included:

(a) introduction of fluoro, deoxy or bulky groups such MeO in the enzyme acceptor moiety at the specific OH group, (the site of action by enzyme position) or OH group/s adjacent to the site of action can be enzyme inhibitors;

(b) anomeric modifications at the position of acceptor/inhibitor moiety.

TABLE 5

| | |
|---|---|
| 5KP* | GlcNAcβ O-P |
| S-KP | GlcNAcβS-P |
| 6KGe* | GlcNAcβO-Ge |
| S6KGe* | GlcNAcβS-Ge |
| 7K Fa | GlcNAcβO-Fa |
| S7K Fa | GlcNAcβS-Fa |
| 8K Nap* | GlcNAcβO-Nap |
| S8K Nap | GlcNAcβS-Nap |
| 9KRE | GlcNAcβO-RE |
| 10K | F6 GlcNAcβOZ |
| S10K | F6 GlcNAcβSZ |

The target decoys,
Farnesol = Fa,
Ge = Geraniol
P = perillyl,
Re = Resveratrol.
NaP = 2-Naphthylmethyl.
S = thio,
Z = Fa, P, Ge or R.
F = Fluorine
*already prepared Specific activities of C1GalT, a Core-1 enzyme that B3GalT utilizes to generate core-1 Galβ3GalNAcα-glycans; and the C3GnT6 enzyme, a Core-3 enzyme that constructs GlcNAcβ3GalNAcα in mucin, have revealed that the aglycone at the anomeric position can affect enzyme activity. Both enzymes act on the first sugar at C-3 of GalNAcα in O-glycans to give their respective cores. Since both enzymes have anomeric specificity, analogs of 5KP with different aglycones were constructed as set forth in Table 5.

Preferably, the decoys of Table 5 are synthesized having an aryl or benzyl radical at anomeric position. As indicated about, interest in testing the decoys with different aglycones occasioned testing the use of natural products and resulted in the synthesis of GalNAcα-perillyl as a decoy for diverting biosynthesis of Mucin O-glycans; and 5KP GlcNAcβO—P (above). Glyco-decoys that incorporate natural products (NP) offer improved therapeutic functionalities such as reduced toxicology, improved pharmacologic half-life or bioavailability, as well as, potentially acting as long-lived pro-drugs. For instance, pro-drugs where endogenous enzymes exist that release NP from the decoy inhibitors and allow mobilization of the decoy inhibitor for cellular uptake. Reduced toxicity is also possible as NP may incorporate potentially toxic radicals into non-toxic aglycones, e.g. nitrophenyl, hexyl, thio and octyl radicals. Table 6 lists illustrative glycosides having NP. Illustrative NP include: i) resveratrol (Re), where glucosylation of resveratrol protects it from oxidation and Glcβ-3Re retains its antioxidant properties; ii) perillyl alcohol and hydroxylated limonene analog, where both perillyl alcohol and limonene have endogenous anti-cancer activity; and iii) geraniol (Ge) and iv) farnesol (Fa), both of which have known anti-tumor activities:

TABLE 6

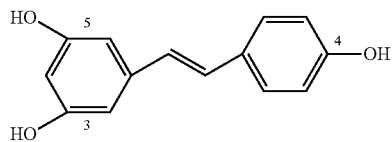

(E)-Resveratrol

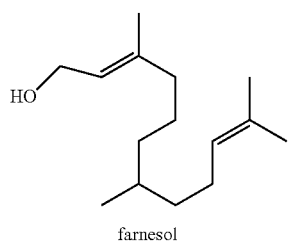 [SMILES: CC(C)=CCCC(C)CCC/C(C)=C/CO]

farnesol

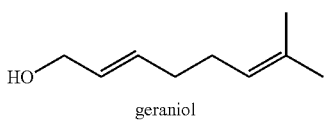

geraniol

TABLE 6-continued

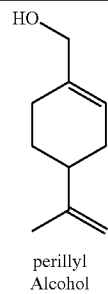

perillyl
Alcohol

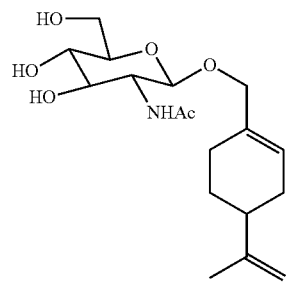

perillyl
Glycoside
5KP

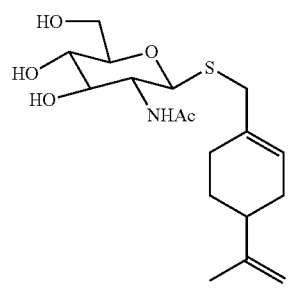

Thio
Glycoside
S-5KP

Selected NaturalProduct and Synthesis of Thio Analog S6Ge.
Reaction conditions: (i) triethylamine in CH₃CN; (ii) sodium methoxide CH₃OH.

Figure 5:
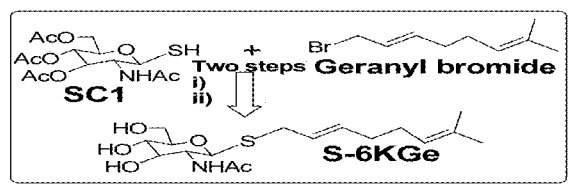
FIG. 5 is a diagram that illustrates synthesis of thioglycoside geranyl decoy inhibitors for N-acetyl hexosaminidases by: (i) condensation reaction of geranyl bromide with Ac-O-protected NAc-sugars in acetonitrile containing triethylamine; (ii) deacetylation; as described in the EXAMPLES section, below.
Figure 7B:
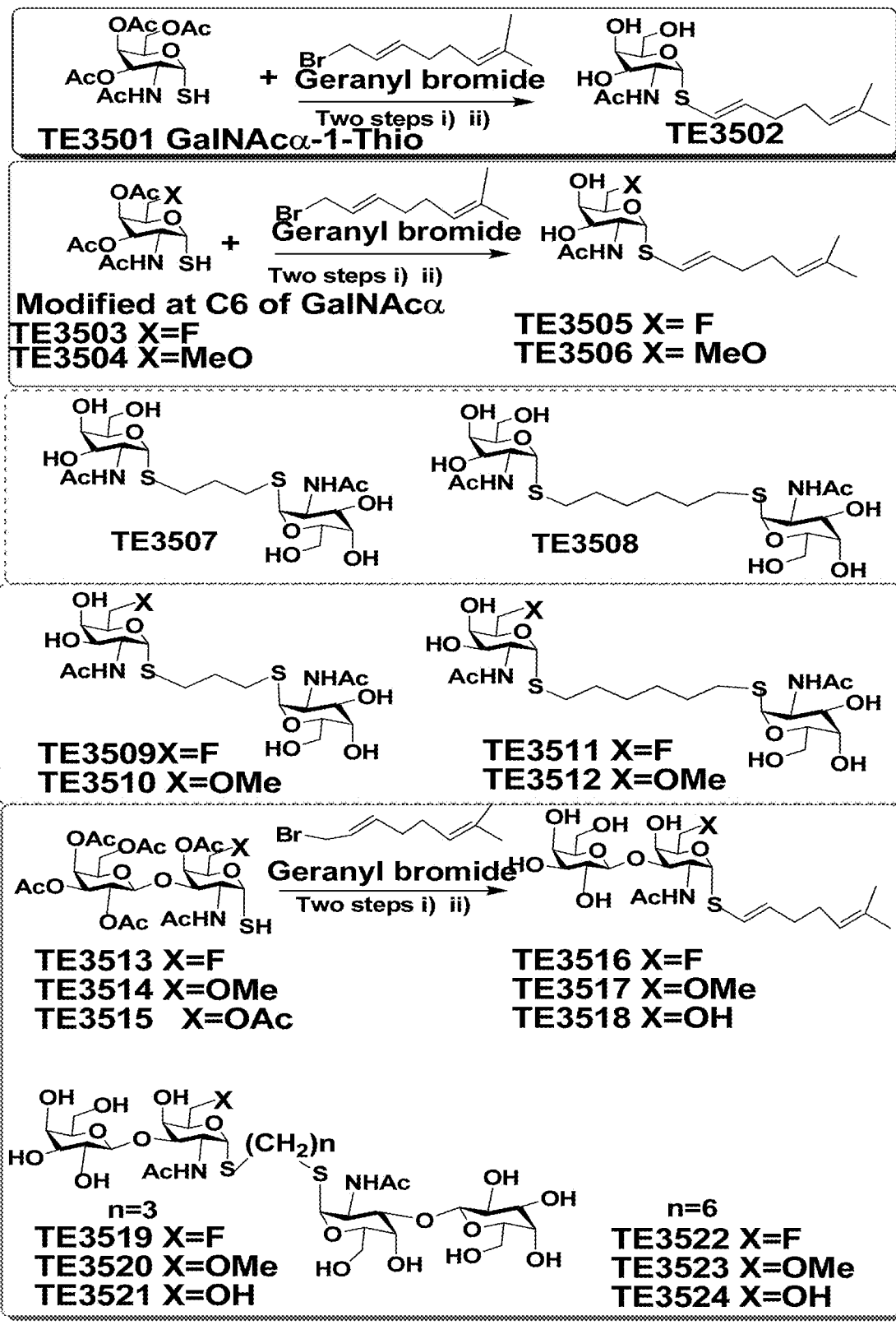
Figure 9:
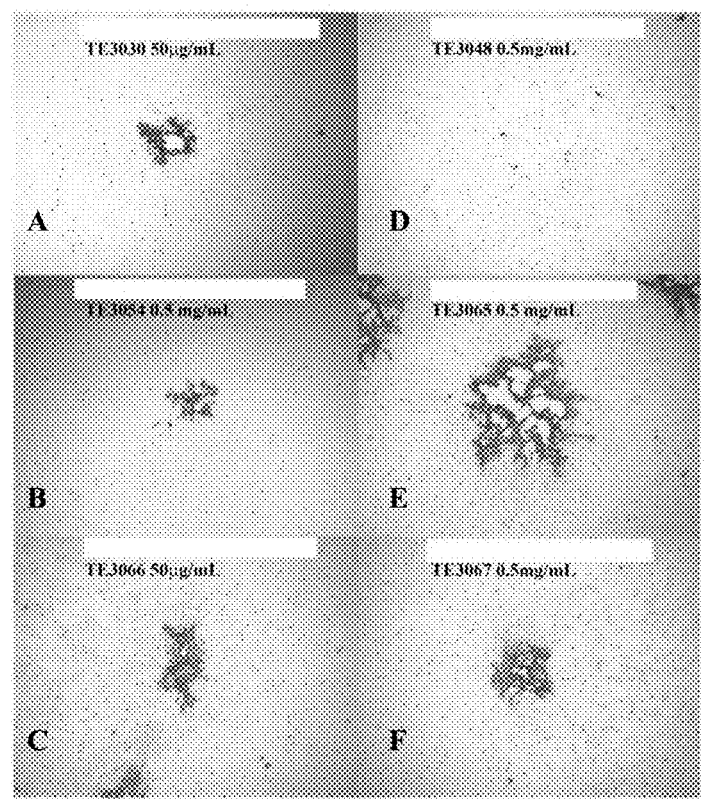
FIGS. 9A-9F are results of HIV-1 reinfectivity assays applied to monolayer cells for a plaque assay of various compounds, as follows.

Thio glycoside analogs as decoy inhibitors: Thio glycosides are not useful substrates for N-acetyl hexosaminidases and can thus affect the synthesis of O-glycan glycosides. Synthesis of thio glycoside decoys is illustrated in FIG. 5, where thio GlcNAc SC1 was prepared as solid material. SC1 was prepared in 2 steps: i) where geranyl bromide reacted in the presence of triethylamine in acetonitrile at room temperature also yielded a solid material, the acetylated derivative of S-6KGe (98% yield); from which, ii) on deacetylation S-6KGe was obtained in a synthesis that did not require chromatographic purification. The instant synthesis is applicable to synthesis of additional thio-glycoside decoy inhibitors.

Example 11

Molecular Tools

The disclosure in EXAMPLES 1-9, above, are used to construct oligonucleotide probes and arrays for profiling gene expression of glycosyl transferase enzymes involved in L-, E- and P-selectin ligand synthesis, as well as, galectin and siglecs ligand synthesis.

Example 12

O-Glycan Decoys

An additional class of compounds (FIG. 6) was synthesized to act as decoys in biosynthetic pathways for mucin O-glycans and globo glycans. The construction of these compounds (FIG. 6) utilized knowledge gained in detailed studies of the specificity of four enzymes: namely, B3 GalT 1 (Cosmo); core3 Gnt1; core 2 Gnt6; and ST6 GalNAcTs. Illustrative compounds according to the invention are set forth in FIG. 6, where:

"1", "2", "3", "4", "5" and "6" are constituent R-modified or unmodified N-acetyl sugars;

B is an R-modified or unmodified radical selected from a sulfo-alkyl $—S—(CH_2)_nR$; a saturated or unsaturated sulfo-alkene $—S—(CH_2)_n—(CH_2)_n=(CH_2)_n—(CH_2)_n—R$; an R-modified cycloalkyl having n carbon atoms; and an R-modified benzyl ring;

R is —H, —OH, —Br, —F, —Cl, $—SO_3$, $—CH_3$ or $—OCH_3$; and wherein n is an integer selected from 1 to 8.

Compounds in FIG. 7A or FIG. 7B also contain divalent analogs.

The divalent branched chain compounds, utilizing component R-modified NAc-sugar structures "1"-"6" (FIG. 7A or 7B) are expected to be better inhibitory decoy activity for B3 GalT 1 (Cosmo); core3 Gnt1; core 2 Gnt6; and ST6 GalNAcTs enzymes, and especially for B3 GalT 1 and for the core 2 enzymes. In this embodiment of the invention, inhibitors with millimolar-micromolar activity, when introduced as substrates into an O-mucin or globo-glycan biosynthetic cascade progressively acquire greater activity as they are modified by each respective enzyme in the cascade; to e.g. produce biosynthetic products having nanomolar to low picomolar inhibitory activity, as a result of the progressive modifications by down-stream enzymes in the cascade.

The class of compounds represented in FIG. 6 and FIGS. 7A-7B, and their derivatives, find a variety of uses as inhibitors of cellular processes involved in bacterial, parasitic and viral infectious diseases; cardiovascular diseases; autoimmune diseases; and cancer. For instance, these compounds find uses as tumor metastasis inhibitors, tumor angiogenesis inhibitors, tumor growth inhibitors; and inhibitors of essential processes required for propagation of viruses, bacteria, fungi and parasites. Decoy-modified glycans produced by infected cells constitute effective vaccine antigens; decoy-modified viruses produced by virus-infected cells constitute effective attenuated viral vaccines; decoy-modified cancer cells, e.g. in situ in a patient, constitute effective oncology vaccines. The instant decoy-modified glycans contain broader ranges of glycan epitopes binding at multiple different dendritic cell lectin receptors (e.g. C-lectin; S-lectin and Galectin) and thus insuring more effective immune Th1/Th2 cross-presentation through both MHC class-1 and -2 processing pathways to effectively induce both Th1 and Th2 immune responses. i.e., both antibodies (Ab) and CDS+ CTL responses. Decoy-treatments of virus-infected and recombinant engineered cell lines result in production of attenuated viruses and viral proteins that are both noninfectious and highly antigenic mf vaccines. As such, the instant decoy-treatments of virus-infected cells constitute processes for safer engineered vaccine production.

Example 13

HIV-1 & Ebola Infectivity Assays

HIV-1: Evidence from HIV-1 reinfectivity assays show that certain compounds described herein significantly reduce viral transmission. Antiviral compounds which completely block HSV replication and reinfection have been determined. These compounds interfere with the glycosylation of Viral Coat Proteins and can be developed as a topical, cell penetrating formulation for Herpes Simplex 1 (HSV-1) and Herpes Simplex 2 therapeutics or for Ocular HSV-1 infections.

In the assays shown in FIGS. 9A-9F, HSV-1 is applied to monolayer of Vero cells (primate monkey kidney cells) for a plaque assay. In this case, 2 TE compounds were combined, one of which was the same in FIGS. 9A-9F and the second compound is indicated by its separate number. As evident in FIG. 9E, TE3065 had little or no plaque reduction activity, while all other compounds reduced the plaque size.

As shown in FIG. 9D, the virus was stopped by a most active compound combination TE3048 at the single cell level. No plaques were formed.

HERPES SIMPLEX VIRUS 1 and 2: The inhibition from the current TE Compounds is due to altering the processing of viral glycoprotein coat of HSV-1, resulting in the glycoprotein having few sugars attached, and causing impaired viral assembly or impaired fusion in the next infection cycle.

A plan is in place to test for a hairless mouse back scratch HSV1 and HSV2 in vivo animal model of infection where local infection can be treated with TE3048 and other compounds. In addition, plans have been made to perform systemic administration of the lead compounds through i.v. tail vein, and by mouth gavage to test systemic effects. However, the topical application of an antiviral will have much more rapid progress through the FDA system.

OCULAR HSV-1: Plans to develop these compounds for an Eye Drop therapeutic using a mouse HSV-1 Ocular Infection model are being made.

EBOLA: This viral therapeutic TE3048 and others may be universal for all viruses with a coat glycoprotein. The GP coat surface glycoprotein of Ebola appears key to its infectivity, and, the glycans on the mucin domain may mask the protein from the immune system. We believe that Ebola virus may be slowed or stopped by the same class of compounds, which we are investigating. We have contacted Dr Thomas Geisbert in Galveston, Texas who has agreed to perform Ebola reinfectivity assays with our TE Compounds. He has an NIAID Center of Excellence Program for testing anti-Ebola drug candidates. Importantly, the Ebola virus plaque assay is performed in the same Vero cells as the HSV-1, therefore it is very likely the effect will be very pronounced.

Thus, it is contemplated that Ebola viruses could be inhibited by such compounds as a new form of therapy. Further, it is contemplated that any virus with a coat glycoprotein, such as influenza, HIV, hepatitis, Marburg, dengue, chikungunya, and other viruses may be inhibited by this class of compound.

It is contemplated that alpha-benzyl galNAC (2-deoxy-2-acetamido-galactose) and its acetylated derivatives are antiviral by acting as a decoy, derailing or side-tracking glycan synthesis to the decoys instead of to the viral coat glycoproteins.

VIRUS COAT GLYCOPROTEIN GLYCOSYLATION DECOYS: We also found that the combination of Benzyl GalNAc with the TE3054 previously showed to be the most effective inhibitor of virus spread. Thus, we attempted other combinations with the Benzyl GalNAc. These results show the TE3048 as more effective at controlling HSV-1 spread than the TE3054 limiting the virus to single infected cells. All the compounds had the effect of limiting some infection to single infected cells. When Benzyl GalNAc was combined with TE3048, no plaque formation was observed. These combinations also may reduce infectious virus production by growth curve focusing on combination treatments of Benzyl GalNAc with TE3054 or TE3048.

Plans are to test the antiviral compounds in an Ebola reinfectivity assay analogous to the HSV-1 assay shown above, since Ebola is propagated in the same Monkey Vero Cells. It is believed that our novel approach will be effective in treating the Ebola virus in an initiated infection.

It is asserted that all viruses with coat glycoproteins may be inhibited from infectivity by derailing their glycan synthesis with decoys that are composed of sugar derivative acceptors, or compounds resembling or functioning as sugar derivative acceptors for initiating or extending O-linked and N-linked glycans on viral coat proteins. The coat proteins can help the virus evade the immune system by host-specified glycans on their surfaces, which protection would be erased by inhibition of glycan synthesis. The actual production of the coat proteins and their assembly may be inhibited by lack of glycans, and their infectivity may be inhibited by lack of glycans on the coat glycoproteins.

Example 14

Additional Analogs of GlcNAcβ Compounds as Decoys

Figure 10:
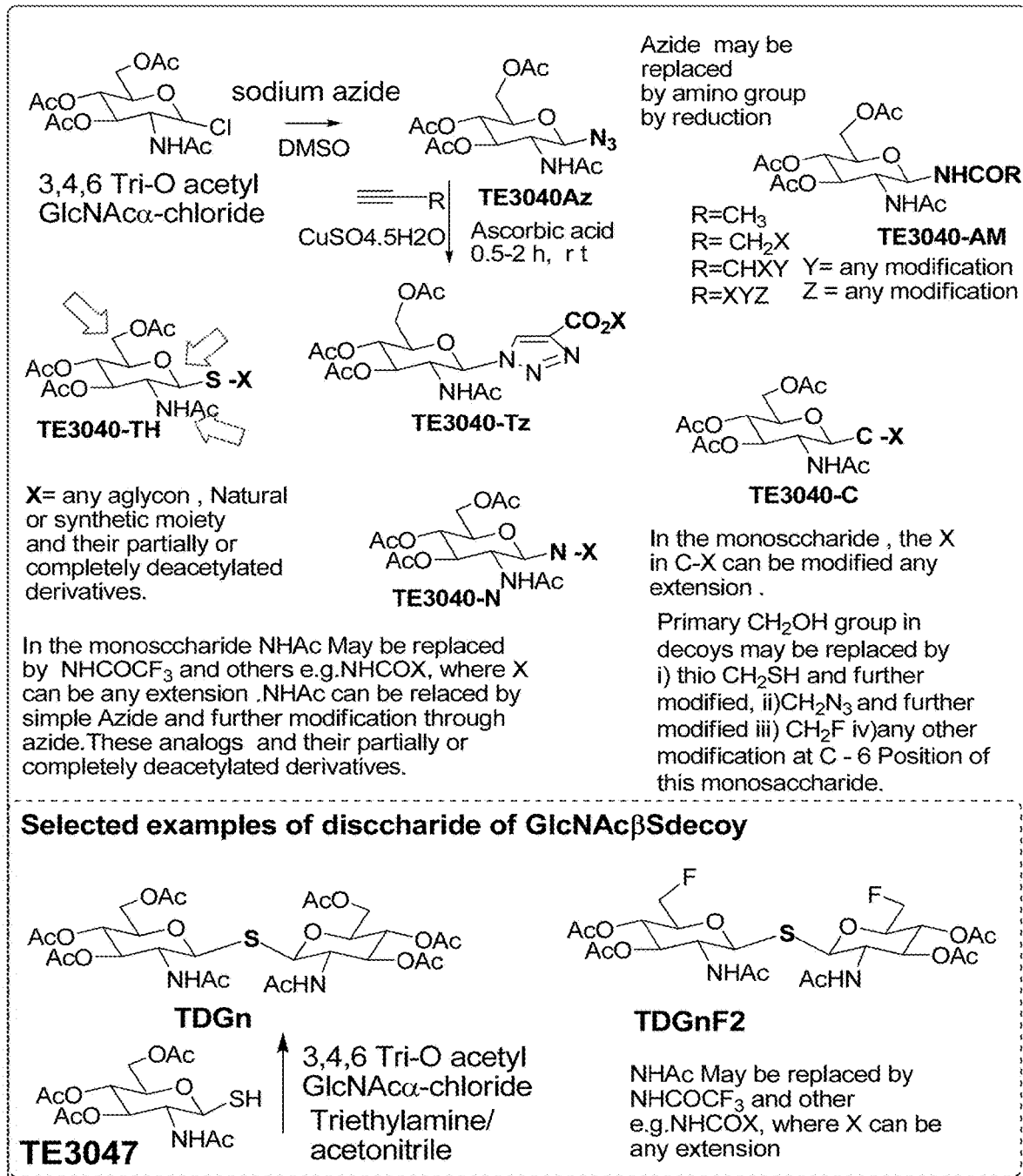
FIG. 10 is a diagram of selected examples of modification of decoys that can disrupt biosynthesis of ligand for E selectin, including ligand for galectin 1. The arrows in TE3040TH-Thio shows the sites of modification. The bottom part shows GlcNAcβS dimer TDGn.

A small set of analogs of monosaccharide GlcNAcβ linked compounds that may improve efficiency have been identified. FIG. 10 shows examples of these target structures with key features. Identification of a molecule for therapeutic studies enhances the interest of whether other modifications will be active.

The activity of GlcNAcβ-Perillyl prompted synthesis of thio analogs for hexasominidase resistance. As shown in FIG. 10, in compound TE3040-TH, the arrows indicate the sites for modification. Like thio-glycosides, analogs having azide, amino, anomeric C—C bonds, structure TE3040-C will also not be prone to degradation by hexasominidase. As indicated in FIG. 10, the primary group $CH_2OH$ in these decoys may be replaced by other functional groups, including $CH_2F$ substitution, e.g., Fluoro-6GlcNAcβSNAP and Fluoro-6GlcNAcβSGe. The NHAc can be replaced by $NHCOCF_3$. The bottom part of FIG. 10 shows additional structures. TDGn thio diGlcNAc is a [GlcNAcβ] 2-S dimer, which is divalent, may have increased activity. Decoy TDGnF2 contains two fluoro groups.

Synthetic Strategy: The outlines for synthesis of some of the analogs are given here. As shown and mentioned earlier, thio-GlcNAc TE3047, when reacted with geranyl bromide (GeBr) in presence of triethylamine in acetonitrile, gave a solid acetylated TE3048 derivative in 98% yield. As shown in the bottom part of FIG. 10, under these reaction conditions 2-acetamido-2 deoxy-3,4,6 tri-O-acetylαD-glucopyranosyl chloride (3,4,6 tri-O-acetyl GlcNAcα-chloride) with thio-GlcNAc TE3047 can be used for synthesis of Structure TDGn. GlcNAcα-chloride on reaction with sodium azide in DMSO125,126 was used for synthesis of TE3040Az (FIG. 10). We have synthesized GalβN3, GlcNAcβN3 and other sugar azides isolated as solid materials without chromatography. The azide function is important for synthesis of a variety of compounds, e.g., glycan arrays via click chemistry using alkynyl compounds. The synthesis of TE40Tz analogs can be prepared. The outcome of biochemical inhibition studies of these new analogs as decoys will be a guide for additional analogs. Replacement of NHAc in Structure TDGn and TDGnF2 will be performed. NMR and mass spectroscopic studies are routinely used in the characterization of synthetic compounds.

CITATIONS

1. Lame R. A calculation of all possible oligosaccharide isomers both branched and linear yields 1.05×1012 structures for a reducing hexasaccharide. Glycobiology 4:903-908, 1994
2. Vestweber, D. and Blanks, J. E.: Mechanisms that regulate the function of the selectins and the ligands. Physiological Reviews 79:181-213, 1999.
3. Varki, A.: Selectin ligands. Proc. Natl. Acad. Sci. USA 91:7390-7397.1994.
4. Tsuboi S, Fukuda M. Roles of O-linked oligosaccharides in immune responses. Bioessays; 23:46-53.2001
5. Bertozzi, C. R., and Kiessling, L. L. Chemical glycobiology. Science 291, 2357-2364,2001.
6. Ley, K. The role of selectins in inflammation and disease Trends Mol. Med. 9, 263-268,2001
7. Gout, S., P. L. Tremblay, and J. Huot. 2008. Selectins and selectin ligands in extravasation of cancer cells and organ selectivity of metastasis. Clin Exp Metastasis 25:335-344.
8. Witz, I. P. The selectin-selectin ligand axis in tumor progression Cancer and Metastasis Reviews 27:19-30 2008
9. Brockhausen I. Pathways of O-glycan biosynthesis in cancer cells. Biochim. Biophys. Acta. 1473:67-95, 1999
10. Brooks S A, Carter T M, et al. Altered Glycosylation of Proteins in Cancer: What Is the Potential for New Anti-Tumour Strategies. Anti-Cancer Agents in Medicinal Chemistry. 8:2-21, 2008.
11. Hang H C and Bertozzi C R. The chemistry and biology of mucin-type O-linked glycosylation. Bioorganic & Medicinal Chemistry 13: 5021-5034, 2005
12. Hollingsworth M A and Swanson B J. Mucins in cancer: protection and control of the cell surface. Nature Rev. Cancer 4:45-60, 2004.
13. Matta, K. L.: Synthetic Glycosyltransferase Acceptors and Inhibitors; Useful Tools in Glycobiology. In: Modern Methods in Carbohydrate Synthesis. Khan, S. H. and O'Neill, R. A. (eds.), Perkin Elmer, Harwood Academic Publishers, pp. 437-466 (1996).
14. Karlsson N G and McGuckin M A O-Linked glycome and proteome of high-molecular-mass proteins in human ovarian cancer ascites: Identification of sulfation, disialic acid and O-linked fucose Glycobiology 22:918-929, 2012
15. Pierre Redelinghuys P, Antonopoulos A et al Early Murine T-lymphocyte Activation Is Accompanied by a Switch from N-Glycolyl- to N-Acetyl-neuraminic Acid and Generation of Ligands for Siglec-E J. Biog. Chem. 286: 34522-34532, 2011
16. Crocker, P. R., Paulson, J. C., Varki, A. (2007) Siglecs and their roles in the immune system. Nat Rev Immunol 7, 255-66.
17. Varki, A., Angata, T. (2006) Siglecs—the major subfamily of I-type lectins. Glycobiology 16, 1R-27R.
18. Varki A, Chen X. Advances in the Biology and Chemistry of Sialic Acids ACS Chemical Biology 5:163-176, 2010.
19. Schauer R. Sialic acids as regulators of molecular and cellular interactions. Curr. Opin Struct. Biol 19:507-514, 2009
20. Berg E L, Robinson M K, Mansson O, Butcher E C and Magnani J L. A carbohydrate domain common to both sialyl Lea and sialyl Lex is recognized by the endothelial cell leukocyte adhesion molecule ELAM-1. J. Biol. Chem. 266:14869-14872, 1991
21. Kawamura, Y. I. Kawashima, R. et al Introduction of Sda Carbohydrate Antigen in Gastrointestinal Cancer Cells Eliminates Selectin Ligands and Inhibits Metastasis Cancer Res 2005; 65, 6220-6227 2005
22. Malgolini, N Santini, D et al Biosynthesis and expression of the Sda and sialyl Lewis x antigens in normal and cancer colon Glycobiology 17: 688-697,2007.
23. Melton S. D; Genta R. M. et al Biomarkers and Molecular diagnosis of gastrointestinal and pancreatic neoplasms Nature Reviews Gastroenterology and Hepatology 7, 620-628,2010.
24. Canny P A, Wilkinson P M et al CA19-9 as a marker for ovarian cancer: alone and in comparison with CA125. Br J Cancer. 52: 131-133, 1985
25. Chandrasekaran, E. J., Jain, R. K. and Matta, K. L.: The enzymatic sulfation of glycoprotein carbohydrate units: blood group T-hapten specific and two other distinct Gal: 3-O-sulfotransferases as evident from specificities and kinetics and the influence of sulfate and fucose residues occurring in the carbohydrate chain on C-3 sulfation of terminal Gal. Glycobiology 7:753-768 (1997).
26. Chandrasekaran, E. V., Lakhaman, S. S., Chawda, R., Piskorz, C. F., Neelamegham, S. and Matta, K. L. Identification of physiologically relevant substrates for cloned Gal:3-O-sulfotransferases (Gal3STs). J. Biol. Chem., 279: 10032-10041, 2004.
27. Allen, K. J., Ahmed, H. and Matta, K. L.: Binding of Synthetic Sulfated Ligands by Human Splenic Galectin 1, a □-galactoside-binding Lectin. Glycoconjugate J. 15:691-695 (1998).
28. Ideo H, Seko A, Ohkura T, Matta K L and Yamashita K. High affinity binding of recombinant human galectin-4 to SO3® 3Galβ® 1*3GalNAc pyranoside. Glycobiology 12:199-208, 2002.
29. Schachter H. Biosynthetic controls that determine the branching and microheterogeneity of protein-bound oligosaccharides. Biochem. Cell Biol. 64:163-181, 1986.
30. Takahashi M Kuroki Y et al Core fucose and bisecting GlcNAc, the direct modifiers of the N-glycan core their functions and target proteins. Carbohydrate Research 344: 1387-1390,2009
31. Czlapinski J L, and Bertozzi C R. Synthetic glycobiology: Exploits in the Golgi compartment. Curr. Opin. Chem. Biol. 10:645-651, 2006.
32. Lairson, l. L. Henrissat B, Henrissat G. J. and Withers S. G. Glycosyltransferases: Structures, Functions, and Mechanisms Annu. Rev. Biochem. 77:521-55,2008.
33. Gadhoum S Z, Sackstein R. CD15 expression in human myeloid cell differentiation is regulated by sialidase activity. Nat. Chem. Biol. 4:751-757, 2008.
34. Chandrasekaran E V, Xue J, Piskorz C, Locke R D, Neelamegham S, Slocum H, and Matta K L. Human gastric tumor-associated reciprocal changes in Gal:3-O-sulfotransferase. Journal of Cancer and Clinical Research 133:599-611, 2007
35. Gama C I and Hsieh-Wilson L C. Chemical approaches to deciphering the glycosaminoglycan code. Curr Opin Chem Biol, 9:609-619, 2005
36. Taylor K R and Gallo R L. Glycosaminoglycans and their proteoglycans: host-associated molecular patterns for initiation and modulation of inflammation. FASEB Journal 20: 9-22, 2006
37. Gandhi, Neha S, Mancera R L. The structure of glycosaminoglycans and their interactions with proteins. Chem Biol Drug Des 72: 455-482, 2008
38. Silbert J E, Sugumaran G. Biosynthesis of chondroitin/dermatan sulfate. IUBMB Life 54:177-186, 2002.
39. Raman K, Kuberan B. Chemical tumor biology of heparan sulfate proteoglycan. Curr Chem Biol 4:20-21, 2010.
40. Mythreye K., Blobe Gerard C. Proteoglycan signaling co-receptors: Roles in cell adhesion, migration and invasion. Cellular Signalling 21:1548-1558,2009.
41. Deepa, S. S., Umehara, Y., et al Specific molecular interactions of oversulfated chondroitin sulfate E with various heparin-binding growth factors. Implications as a physiological binding partner in the brain and other tissues. J Biol Chem 277, 43707-43716, 2002.
42. Kawashima H, Atarashi K et al Oversulfated chondroitin/dermatan sulfates containing GlcAb1/IdoAa1-3Gal-NAc (4,6-O-disulfate) interact with L- and P-selectin and chemokines. J Biol Chem 277:12921-12930, 2002.
43. Johnstone K D, Karoli T, et al. Synthesis and biological evaluation of polysulfated oligosaccharide glycosides as inhibitors of angiogenesis and tumor growth. J Med Chem 53:1686-1699, 2010.
44. Grose, R., Dickson, C. Fibroblast growth factor signaling in tumorigenesis. Cytokine Growth Factor Rev 16, 179-186, 2005
45. Sakko A J, Ricciardelli C, et al. Modulation of prostate cancer cell attachment to matrix by versican. Cancer Res 63: 4786-4791, 2003.
46. Sakko A J, Bultler M, et al. Immunohistochemical level of unsulfated chondroitin disacharides in the cancer stroma is an independent predictor of prostate cancer relapse. Cancer Epidermiol Biomarkers Prev 17(9):2488-2497, 2008.
47. Iid S, Suzuki A K, et al. Analysis of glycosaminoglycans in human prostate by high-performance liquid chromatography. Brit J Urol 79:763-769,
48. Ten Dam G B, Van De Westerlo E M A, et al. Antibody GD3G7 selected against embryonic glycosaminoglycans defines chondroitin sulfate-E domains highly up-regulated in ovarian cancer and involved in vascular endothelial growth factor binding. Am J Pathol 171:1324-1333, 2007.
49. Ito Y, Wantabe M, et al, The utility of formalin-fixed and paraffin-embedded tissue blocks for quantitative analysis of N-acetylgalactosamine 4-sulfate 6-O-sulfotransferase mRNA expressed by colorectal cancer cells. Acta Histochemica et Cytochemica 40: 53-59, 2007.
50. Basappa M S, Sugahara K N, et al. Involvement of chondroitin sulfate E in the liver tumor focal formation of murine osteosarcoma cells. Glycobiology 19:735-742, 2009.
51. Li F, Ten Dam G B, et al. Involvement of highly sulfated chondroitin sulfate in the metastasis of the Lewis lung carcinoma cells. J Biol Chem 283:34294-34304, 2008.
52. Monzavi-Karbassi Behjatolah Steven Stanley, et al. Chondroitin sulfate glycosaminoglycans as major P-selectin ligands on metastatic breast cancer cell lines. Int. J. Cancer 120: 1179-1191, 2007 Monzavi-Karbassi,
53. Brown, J. R., Crawford, B. E., Esko, J. D. Glycan antagonists and inhibitors: A fount for drug discovery. Crit Rev Biochem Mol Biol 42: 481-515, 2007.
54. Sarkar, A. K., Rostand, K. S., Jain, R. K., Matta, K. L., and Esko, J. D. Fucosylation of disaccharide precursors of sialyl Lewisx inhibit selectin-mediated cell adhesion. J Biol Chem 272: 25608-25616, 1997.
55. Woynarowska, B., Skrincosky, D. M., Haag, A., Sharma, M., Matta, K., and Bernacki, R. J. Inhibition of lectin-mediated ovarian tumor cell adhesion by sugar analogs. J Biol Chem 269: 22797-803, 1994.

56. Sackstein, R., Dimitroff, C. J., Bernacki, R. J., Sharma, M., Matta K. L., and Paul, B. Fluorinated glucosamine analogs useful for modulating post-translational glycosylations on cells, U.S. Pat. No. 7,098,195, 2006.
57. Dimitroff, C. J., Bernacki, R. J., Sackstein, R. Glycosylation-dependent inhibition of cutaneous lymphocyte-associated antigen expression: implications in modulating lymphocyte migration to skin. Blood 101: 602-610, 2003.
58. Marathe, D. J. Buffone, Jr a et al Fluorinated per-acetylated GalNAc metabolically alters glycan structures on leukocyte PSGL-1 and reduces cell binding to selectins Blood; 115: 1303-1312,2010.
59. Yarema, K. J., Goon, S., Bertozzi, C. R. Metabolic selection of glycosylation defects in human cells. Nat Biotechnol 19: 553-558, 2001.
60. Okamura, A., Yazawa, S., Nishimura, T., Tanaka, S., Takai, I., Kudo, S., Asao, T., Kuwano, H., Matta, K. L., Akamatsu, S. and Kochibe, N. A new method for assaying adhesion of cancer cells to the greater momentum and its application for evaluating anti-adhesion activities of chemically synthesized oligosaccharides. Clin Exp Metastasis 18:37-43, 2000.
61. Abrahamsson, C-O., Ellervik, U., et al. Xylosylated naphthoic acid—amino acid conjugates for investigation of glycosaminoglycan priming. Carbohydrate Research 343: 1473-1477, 2008.
62. Nigro, J., Wang, A., et al. Regulation of heparan sulfate and chondroitin sulfate glycosaminoglycan biosynthesis by 4-Fluoro-glucosamine in murine airway smooth muscle cells J Biol Chem 284: 16832-16839, 2009.
63. Allen, J. R., Harris, C. R. and Danishefsky, S. J. Pursuit of optimal carbohydrate-based anticancer vaccines: Preparation of a multiantigenic unimolecular glycopeptide containing the Tn, MBrl, and Lewisy antigens. J. Am. Chem. Soc., 123:1890-1897, 2001.
64. Slovin, S. F., Ragupathi, G., Adluri, S., Ungers, G., Terry, K., Kim, S., Spassova, et al. Carbohydrate vaccines in cancer: Immunogenicity of a fully synthetic globo H hexasaccharide conjugate in man. Proc Natl Acad Sci USA 96: 5710-5715, 1999.
65. Newman, D. J., Cragg, G. M., Snader, K. M. Natural products as sources of new drugs over the period 1981-2002 J Nat Prod 66, 1022-1037, 2003
66. Borman, S. (no title) Chem. Eng. News Jan. 14, 23-24, 2002.
67. Matta K L, Chandrasekaran E V, et al. Profiling glycosyltransferase activities in cancer cells using chemically-synthesized, well-defined acceptors. Meeting Abstract, Glycobiology Meeting, Los Angeles, CA, Nov. 15-19, 2006.
68. Matta K L, Xue J, Lau J T Y, Mohler J, et al. Glycobiology of prostate cancer cells. Prostate Cancer Research Program, IMPACT Meeting, Atlanta GA, 2007.
69. Peracaula, R., Tabares, G., et al. Altered glycosylation allows the distinction between prostate-specific antigen (PSA) from normal and tumor origins. Glycobiology 13:457-470, 2003.
70. Chandrasekaran E V, et al. The pattern of glycosyl- and sulfotransferase activities in cancer cell lines: a predictor of individual cancer-associated distinct carbohydrate structures for the structural identification of signature glycans. Carbohydr. Res. 341:983-994, 2006
71. Miller, S., Hanisch, F-G. Recombinant MUC1 probe authentically reflects cell-specific O-glycosylation profiles of endogenous breast cancer mucin. J Biol Chem 277: 26103-26112, 2002.
72. Marathe D D, Chandrasekaran E V, Lau, J T Y, Matta K L, Neelamegham S. Systematic evaluation of glycosyltransferase gene expression and enzyme activity that is associated with the selectin binding function of human leukocytes. FASEB J. 22:4154-4167, 2008.
73. Gang L, Marathe D D, et al. Systems-level modeling of cellular glycosylation reaction networks: O-linked glycan formation on natural selectin ligands. Bioinformatics, 24:2740-2747.2008
74. Nairn A V, York W S, et al. Regulation of Glycan Structures in Animal Tissues: Transcript profiling of glycans related Genes J. Biol. Chem. 283: 17298-1731, 2008.
75. Nairn A V, Kinpshita-Toyoda A et al. Glycomics of proteoglycan biosynthesis in murine embryonic stem cell differentiation. J. Proteome Research 6:4374-4387, 2007
76. Suga A, Yamanishi Y I, et al. An improved scoring scheme for predicting glycosyltransferases from gene expression data. Genome informatics, International Conference on Genome Informatics 18: 237-246, 2007.
77. Saravanan, C Cao Z et al Analysis of differential expression of glycosyltransferases in healing corneas by glycogene microarrays Glycobiology: 20 13-23, 2010.
78. Tateno H, Toyota M et al Glycome diagnosis of human induced pluripotent stem cells using lectin microarray J. Biol. Chem. 286:10345-10353,2011* discusses profiles of enzymes.
79. Wang P H, Lee W L, Juang C M, Yang Y H, Lo W H, Lai C R, Hsieh S L, Yuan C C: Altered mRNA expressions of sialyltransferases in ovarian cancers. Gynecol Oncol 2005, 99:631-639
80. Patil S. A. Chandrasekharan E V et al Scaling down the size and increasing the throughput of glycosyltransferase assays: Activity changes on stem cell differentiation. Analyt. Biochem 425, 15: 135-144,2012
81. Chandrasekaran E V, Xue J, Xia J, Chawda R, Piskorz C, Locke R D, Neelamegham S, Matta K L. Analysis of the specificity of sialyltransferases toward mucin core 2, globo, and related structures. Identification of the sialylation sequence and the effects of sulfate, fucose, methyl, and fluoro substituents of the carbohydrate chain in the biosynthesis of selectin and siglec ligands, and novel sialylation by cloned alpha2,3(O)sialyltransferase. Biochemistry. 44:15619-15635, 2005.
82. Jain, R. K., Piskorz, C. f., Chandrasekaran, E. V. and Matta, K. L.: Synthesis of Gal-1-(14)-GlcNAc-(16)-[Gal-(13)]-GalNAc-O-BN Oligosaccharides Bearing O-methyl or O-sulfo Groups at C-3 of the Gal Residue: Specific Acceptors for Gal: 3-O-sulfotransferases. Glyconj. J. 15:951-957, 1998.
83. Chandrasekaran, E. V., Jain, R. K. and Matta, K. L. Mucin biosynthesis revisited. The enzymatic transfer of Gal in β1,3 linkage to the GalNAc moiety of the core structure R1-GlcNAcβ1,6GalNAcα-0-R2. J. Biol. Chem., 267:19929-19937, 1992.
84. Chandrasekaran, E. V., Jain, R. K., Larsen, R. D., Wlasichuk, K., DiCioccio, R. A. and Matta, K. L.: Specificity Analysis of Three Clonal and Five Non-clonal □-L-Fucosyltransferases with Sulfated, Sialylated or Fucosylated Synthetic Carbohydrates as Acceptors in Relation to the Assembly of 3□-Sialyl, 6□-Sulfo Lewis X (the L Selectin Ligand) and Related Complex Structures. Biochemistry 35:8925-8933, 1996
85. Chandrasekaran, E. V., Jain, R. K., Larsen, R. D., Wlasichuk, K. and Matta, K. L.: Characterization of the specificities of human blood group H gene-specified □1,2-L-fucosyltransferase toward sulfated/sialylated/fucosylated acceptors: Evidence for an inverse relationship between ☐1,2-L-fucosylation of Gal and ☐1,6-L-fucosylation of asparagine-linked GlcNAc. Biochemistry 35:8914-8924 1996.
86. Yazawa, S., Abbas, S. A., Madiyalakan, R., Barlow, J. J. and Matta, K. L.: N-Acetyl-D-D-Glucosaminyltransferases Related to the Synthesis of Mucin-type Glycoproteins in Human Ovarian Tissue. Carbohydr. Res. 149:241-252,1986.
87. Madiyalakan, R., Piskorz, C. F., Piver, M. S. and Matta, K. L.: Serum ☐-(1☐4)-Galactosyltransferase Activity with Synthetic Low Molecular Weight Acceptor in Human Ovarian Cancer. Eur. J. Can. & Clin. Oncol. 23(7):901-906 (1987).
88. Chandrasekaran, E. V., Chawda, R., Piskorz, C., Locke, R. D., Ta, A., Sharad, G., Odunsi, K., Lele, S. and Matta, K. L. Human ovarian cancer, lymphoma spleen, and bovine milk GlcNAc:β1,4GalNAc transferases: two molecular species in ovarian tumor and induction of GalNAcβ1, 4Glc synthesis by α-lactalbumin. Carbohydr. Res., 334:105-118, 2001.
89. Chandrasekaran, E. V., Jain, R. K., Rhodes, J. M., Srnka, C. A. and Matta, K. L. Expression of Blood Group Lewis b Determinant from Lewis a: Association of this Novel a(1,2-L)-Fucosylating Activity with the Lewis Type a(1, 3/4)-L-Fucosyltransferases. Biochem., 34:4748-4756, 1995.
90. Madiyalakan, R., Yazawa, S. and Matta, K. L.: Characterization of Plasma ☐(1☐3)-L-Fucosyltransferase from an Ovarian Cancer Patient with the Aid of Synthetic Substrates. Indian J. Biochem. Biophys. 25:32-35,1988
91. Chandrasekaran, E. V., Jain, R. K., Abbas, S. A. and Matta, K. L.: 3☐-O-Sulfo N-acetyllactosamine, a unique substrate for ☐1,3-L-fucosyltransferase. Abstract presented at the 11th International Symposium on Glycoconjugates in Toronto, Ontario, Canada, July 1991; Glycoconjugate Journal 8 (No. 3) Supplement.
92. Chandrasekaran, E. V., Jain, R. K. and Matta, K. L.: Ovarian Cancer ☐1,3-L-Fucosyltransferase. Differentiation of Distinct Catalytic Species with The Unique Substrate, 3'-Sulfo-N-Acetyllactosamine in Conjunction with Other Synthetic Acceptors. J. Biol. Chem. 267:23806-23814 1992.
93. Matta, K. L., Jain, R. K. and Chandrasekaran, E. V.: U.S. patent Issued in April 1997, #5620864—Acceptor for Fucosyltransferase, application submitted in July 1992.
94. Yuen, C., Lawson, A. M., Chai, W., Larkin, M., Stoll, M. S., Stuart, A. C., Sullivan, F. X., Ahern, T. J. and Feizi, T.: Novel Sulfated Ligands for the Cell Adhesion Molecule E-Selectin Revealed by the Neoglycolipid Technology Among O-Linked Oligosaccharides on an Ovarian Cystadenoma Glycoprotein. Biochemistry 31:9126-9131, 1992.
95. Nicolaou, K. C., Bockovich, N. J. and Carcanague, D. R.: Total Synthesis of Sulfated Lex and Lea-Type Oligosaccharide Selectin Ligands. J. Am. Chem. Soc. 115: 8843-8844, 1993.
96. Chandrasekaran, E. V., Jain, R. K., Rhodes, J. M., Chawda, R., Piskorz, C. and Matta, K. L.: Characterization of distinct Gal:3-O-sulfotransferase activities in human tumor epithelial cell lines and of calf lymph node GlcNAc:6-O-sulfotransferase activity. Glycoconj. J. 16:523-536, 1999
97. Capon, C., Wieruszeski, J-M., Lemoine, J., Byrd, J. C., Leffler, H. and Kim, Y. S.: Sulfated Lewis X determinants as a major structural motif in glycans from LS174T-HM7 human colon carcinoma mucin. J. Biol. Chem. 272: 31957-31968, 1997.
98. Hiruma, T. and Togayachi, A. A novel human β1,3-N-Acetylgalactosaminyltransferase. J. Biol. Chem. 279: 14087-14095, 2004.
99. Sato, T., Goto, H. Molecular Cloning and Characterization of a Novel Human β1,4-N-Acetylgalactosaminyltransferase. J. Biol. Chem., 278: 47534-47544, 2003.
100. Fiete D, Beranek M and Baenziger J U Peptide-specific transfer of N-acetylgalactosamine to O-linked glycans by the glycosyltransferases β4GalNAc-T3 and β4GalNAc-T4 J. Biol. Chem Jun. 21, 2012
101. Fiete D, Beranek M and Baenziger J U Molecular Basis for protein-specific transfer of N-acetylgalactosamine to N-linked glycans by the glycosyltransferases β4GalNAc-T3 and β4GalNAc-T4J. J. Biol. Chem Jun. 21, 2012
102. Kawar, Ziad S.; Haslam, Stuart M.; Morris, Howard R.; Dell, Anne; and Cummings, Richard D. Novel Poly-GalNAcβ1-4GlcNAc (LacdiNAc) and Fucosylated Poly-LacdiNAc N-Glycans from mammalian cells expressing β1,4-N-Acetylgalactosaminyltransferase and α1,3-Fucosyltransferase; J. Biol. Chem 280: 12810-12819, 2005.
103. Garcia-Vallejo, Juan J.; Van Dijk, Willem; et. al. Activation of human endothelial cells by tumor necrosis factor-α results in profound changes in the expression of glycosylation-related genes. Journal of Cellular Physiology 206: 203-210, 2006.
104. Peracaula, R., Royle, L., Tabares, G., Mallorqui-Fernindez, G., Barrabes, S., Harvey, D. J., Dwek, R. A., Rudd, P. M. and deLlorens, R. Glycosylation of human pancreatic ribonuclease: differences between normal and tumor states. Glycobiol., 13:227-244, 2003.
105. Dell, Anne; Morris, Howard R.; et. al. Structural analysis of the oligosaccharides derived from glycodelin, a human glycoprotein with potent immunosuppressive and contraceptive activities. J. Biol. Chem. 270: 24116-24126, 1995.
106. Jeschke, Udo, Ioannis Mylonas et al "Expression of glycodelin protein and mRNA in human ductal breast cancer . . . Oncology Report 13 (2005): 413-419.
107. Ragupathi G. Koganty R R, et al. A novel and efficient method for synthetic carbohydrate conjugate vaccine conjugate using a 4-(4-N-maleimidomethyl) cyclohexane-1-carboxyl hydrazide preparation synthesis of sialyl Tn-KLH conjugate (MMCCH) linker arm. Glycoconj J 15:217-221, 1998.
108. Mathew G, Timm Jr E. A, Sotomeyer P, Godoy A, Montenocinos V, Smith G J, Huss W. Cell Cycle 8:1053 1061,2009
109. Song Y, Aglipay J A, Bernstein J. D, Goswami S, Stanley P The Bisecting GlcNAc on N-Glycans Inhibits Growth Factor Signaling and Retards Mammary Tumor Progression Cancer Res; 70: 3361-71,2010
110. Zhao Y, Sato Y, et al. Branched N-glycans regulate the biological functions of integrins and cadherins. FEBS J 275:1939-1948, 2008.
111. Guo H, Randolph M, Pierce, M. Inhibition of a specific n-glycosylation activity results in attenuation of breast carcinoma cell invasiveness-related phenotypes. J Biol Chem 282(30):22150-22151, 2007
112. Lau K, Partridge E, Grigorian A, et al. Complex N-glycan number and degree of branching cooperate to regulate cell proliferation and differentiation. Cell 129: 123-34, 2007
113. Toshie Iwai T, Kudo T et al Core 3 synthase is down-regulated in colon carcinoma and profoundly suppresses the metastatic potential of carcinoma cells PNAS 102: 4572-4577, 2005.

114. Lee S. H Hatakeyama S et al Core3 O-glycan synthase suppresses tumor formation and metastasis of prostate carcinoma PC3 and LNCaP cells through down-regulation of α201 integrin complex J. Biol. chem. 284: 17157 17169, 2009.
115. Patnaik. K and Stanley P. Mouse Large Can Modify Complex N- and Mucin O-Glycanson_-Dystroglycan to Induce Laminin Binding J. Biol. Chem. 280: 20851-20859, 2005
116. Bao X, Kobayashi M, et al Tumor suppressor function of laminin-binding a-dystroglycan requires a distinct B3-Nacetylglucosaminyltransferase. Proc Natl Acad Sci USA 106:12109-12114,2009
117. Shimojo H, Kobayashi, et al Reduced Glycosylation of a-Dystroglycans on Carcinoma Cells Contributes to Formation of Highly Infiltrative Histological Patterns in Prostate Cancer Prostate 71: 1151-1157, 2011.
118. Handa K, Hakomori S I. Carbohydrate to carbohydrate interaction in development process and cancer progression. Glycoconj J. May 2012
119. Hakomori S I. Structure and function of glycosphingolipids and sphingolipids: recollections and future trends. Biochim Biophys Acta. 1780:325-46,2008.
120. Harvey D. Matrix-Assisted Laser Desorption/Ionization Mass Spectrometry of Carbohydrates and glycoconjugates. Int. J. Mass Spectrom. 226:1-35, 2003.
121. Ohtake, Shiori, Kondo, Sachiko et al. Expression of sulfotransferases involved in the biosynthesis of chondroitin sulfate E in the bone marrow derived mast cells. Biochimica Et Biophysica Acta 1780: 687-695,2008
122. Kusche-Gullberg M, Kjellen L Sulfotransferases in glycosaminoglycan biosynthesis Current Opinion in Structural Biology 2003, 13:605-611,2003
123. Esko J D, Selleck S B. Order out of chaos: Assembly of ligand binding sites in heparan sulfate. Ann Rev Biochem 71:435-71, 2002.
124. Kitagawa H, Tsutsumi K, et al. Sulfation of the galactose residues in the glycosaminoglycan protein linkage region by recombinant human chondroitin 6-O-sulfotransferase-1. J Biol Chem 41:27438-27443, 2008
125. Shibata T. K. Matsmura F et al Identification Identification of Mono- and Disulfated N-Acetyl-lactosaminyl Oligosaccharide Structures as Epitopes Specifically Recognized by Humanized Monoclonal Antibody HMOCC-1 Raised against Ovarian Cancer J Biol Chem. 287: 6592-6602.2012
126. Sylvie M S Prorok, M Transgene Expression of α(1, 2)-Fucosyltransferase-α (FUT1) in Tumor Cells Selectively Inhibits Sialyl-Lewis x Expression and Binding to E-Selectin without Affecting Synthesis of Sialyl-Lewis a or Binding to P-Selectin Am J Pathol 164:371-383,2004.
127. Canis K, McKinnon T A, Nowak A, Panico M, Morris H R, et al. The plasma von Willebrand factor O-glycome comprises a surprising variety of structures including ABH antigens and disialosyl motifs. J Thromb Haemost 8: 137-145,2010
128. van Schooten C J, Denis C V, Lisman T, Eikenboom J C, Leebeek F W, et al. Variations in glycosylation of von Willebrand factor with O-linked sialylated T antigen are associated with its plasma levels. Blood 109: 2430-2437.2007
129. Nowak A, Canis, K et al O-linked glycosylation of von Willebrand factor modulates the interaction Blood—Apr. 19,2012
130. McGrath R, McKinnon T, Byrne B, et al. Expression of terminal alpha2-6-linked sialic acid on von Willebrand factor specifically enhances proteolysis by ADAMTS13. Blood. 115:2666-2673.2010.
131. Bast, R. C., Jr., Feeney, M., Lazarus, H., Nadler, L. M., Colvin, R. B., and Knapp, R. C. Reactivity of a monoclonal antibody with human ovarian carcinoma J. Clin. Invest. 68:1331-1337,1981
132. Karam A K, Karlan B Y. Ovarian cancer: The duplicity of CA125 measurement. Nat Rev Clin Oncol. 7 335-339, 2010
133. Wong, N. K., Easton, R. L., Panico, M., Sutton-Smith, M., Morrison, J. C., Lattanzio, F. A., Morris, H. R., Clark, G. F., Dell, A. and Patankar, M. S. Characterization of the oligosaccharides associated with the human ovarian tumor marker CA125. J. Biol. Chem., 278:28619-28634, 2003.
134. Yin, B. W. T., Dnistrian, A., and Lloyd, K. O. Ovarian cancer antigen CA125 is encoded by the MUC16 mucin gene. Int. J. Cancer 98: 737-740,2002.
135. Thomas A. Sellers T A, Huang Y Association of Single Nucleotide Polymorphisms in Glycosylation Genes with Risk of Epithelial Ovarian Cancer Cancer Epidemiol Biomarkers Prev. 17:397-404,200
136. Bjo"rkman Y A, Thomsson K A et al Large Scale Identification of Proteins, Mucins, and Their O-Glycosylation in the Endocervical Mucus during the Menstrual Cycle Molecular & Cellular Proteomics 6:708-716, 2007.
137. Saldova R, Wormald M R, Dwek R A, Rudd P M. 2008. Glycosylation changes on serum glycoproteins in ovarian cancer may contribute to disease pathogenesis. Dis Markers. 25(4-5):219-232.
138. Chauhan S C, Kumar D, Jaggi M. Mucins in ovarian cancer diagnosis and therapy. J Ovarian Res. 2:21,2009
139. Zouridis, H., Deng, N., Ivanova, T., Zhu, Y., Wong, B., Huang, D., Hui Wu, Y., Wu, Y., Tan, I. B., Liem, N., Gopalakrishnan, V., Luo, Q., Wu, J., Lee, M., Yong, W-P., Goh, L. K., The, B. T., Rozen, S. and P. Tan. 2012. Methylation subtypes and large-scale epigenetic alterations in gastric cancer. Sci. Transl. Med. 156(4): 140-156. DOI: 10.1126/scitranslmed.3004504

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A decoy inhibitor of N-glycan or O-glycan biosynthesis comprising an effective amount of 3,4,6-Tri-O-acetyl GlcNAc β-thio-geranyl having a structure as follows:

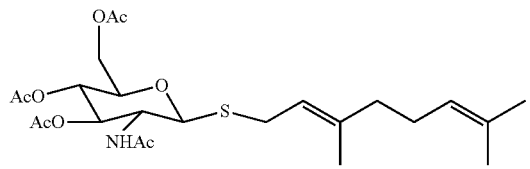 [SMILES: CC(=O)NC1C(SC/C=C(\C)CCC=C(C)C)OC(COC(C)=O)C(OC(C)=O)C1OC(C)=O]

* * * * *